US011809827B2

(12) United States Patent
Ferrucci et al.

(10) Patent No.: US 11,809,827 B2
(45) Date of Patent: Nov. 7, 2023

(54) INTERACTIVE RESEARCH ASSISTANT—LIFE SCIENCE

(71) Applicant: Elemental Cognition Inc., Wilton, NY (US)

(72) Inventors: David A. Ferrucci, Wilton, CT (US); Shirin Saleem, Lexington, MA (US); Aditya A. Kalyanpur, Fort Lee, NJ (US)

(73) Assignee: Elemental Cognition Inc., New York, NY (US)

( * ) Notice: Subject to any disclaimer, the term of this patent is extended or adjusted under 35 U.S.C. 154(b) by 99 days.

(21) Appl. No.: 17/580,654

(22) Filed: Jan. 21, 2022

(65) Prior Publication Data

US 2023/0237271 A1   Jul. 27, 2023

(51) Int. Cl.
| | |
|---|---|
| G06F 16/28 | (2019.01) |
| G06F 40/30 | (2020.01) |
| G06F 9/451 | (2018.01) |
| G16H 50/70 | (2018.01) |
| G06F 40/169 | (2020.01) |
| G06F 40/205 | (2020.01) |

(Continued)

(52) U.S. Cl.
CPC ............ G06F 40/30 (2020.01); G06F 3/0482 (2013.01); G06F 9/453 (2018.02); G06F 16/24578 (2019.01); G06F 16/287 (2019.01); G06F 40/169 (2020.01); G06F 40/205 (2020.01); G16H 50/70 (2018.01)

(58) Field of Classification Search
CPC .............. G06Q 20/4016; G06Q 20/389; G06F 18/2323
See application file for complete search history.

(56) References Cited

U.S. PATENT DOCUMENTS

| | | |
|---|---|---|
| 9,251,202 B1 | 2/2016 | Uszkoreit et al. |
| 2005/0220351 A1 | 10/2005 | Vanderwende et al. |
| 2009/0063472 A1 | 3/2009 | Pell et al. |

(Continued)

FOREIGN PATENT DOCUMENTS

WO    WO2014210387 A2    12/2014

OTHER PUBLICATIONS

Office Action for U.S. Appl. No. 17/580,650, dated Jan. 18, 2023, Feruccu, "Interactive Research Assistant—User Interface/ User Experience (UI/UX)", 20 Pages.

(Continued)

*Primary Examiner* — Truong V Vo
(74) *Attorney, Agent, or Firm* — Lee & Hayes, P.C.

(57) ABSTRACT

A research assistant system may include a research tool and components and a user interface to discover and evidence answers to complex research questions. The research tools may include components to iteratively perform steps in a research process, including searching, analyzing, connecting, aggregating, synthesizing, and chaining together evidence from a diverse set of knowledge sources. The system may receive an input query and perform a semantic search for key concepts in a text corpus. A semantic parser may interpret the search results. The system may aggregate and synthesize information from interpreted results. The system may rank and score the aggregated results data and present data on the user interface. The user interface may include prompts to iteratively guide user input to explore evidentiary chains and connect research concepts to produce research results annotated by evidence passages.

20 Claims, 29 Drawing Sheets

(51) Int. Cl.
    *G06F 3/0482* (2013.01)
    *G06F 16/2457* (2019.01)

(56) References Cited

U.S. PATENT DOCUMENTS

2010/0070448 A1    3/2010  Omoigui
2010/0077001 A1    3/2010  Vogel et al.
2010/0228693 A1    9/2010  Dawson et al.
2011/0208776 A1    8/2011  Lee et al.
2019/0243839 A1    8/2019  Tanne et al.

OTHER PUBLICATIONS

PCT Search Report and Written Opinion dated Oct. 7, 2022 for PCT application No. PCT/US2022/013210, 9 pages.

Document Summary [Edit]

Salivary Gland Epithelial Cells release IL-33 in the extracellular space upon pro-inflammatory stimuli and/or dysfunction of the epithelial barrier [1][2].

IL-33 binds with receptor ST-2 when released during cell injury on the surface of those cells [3] (4) to activate the IL-33/ST-2 signaling pathway [4].

IL-33/ST-2 pathway recruits the Myddosome complex comprised of MyD88 (myeloid differentiation primary response gene 88), IRAK (interleukin-1 receptor-associated kinase 1), and IRAK4 [5].

The Myddosome complex activates either the MAPK pathway [6] or NFkB pathway [6] which in turn induces IL-33 via cytokine gene expression [6].

IL-33 synergistically interacts with IL-12 and IL-23 on NK cells and NKT cells to increase the production of IFN-y [6].

IFN-Y acts on the Salivary Gland Epithelial Cells to release IL-33 [1].

IFN-y in turn further activates the IL-33/ST2 pathway, further contributing to inflammation and disease progression [1][6].

References

1. ExampleName, F. (2019). Pathophysiologic Role of Interleukin-33/ST2 in Syndrome A. *Autoimmune Rev.*, 2019 Jan 18. PMID:1234.
2. LastName1, A. LastName2, B. LastName3, C. (2013). Syndrome A and the Epithelial Target: A Review. *Journal of Autoimmunity*, 42. IC1016/j.jaut.2013.02.001.
3. LastName4, T. The IL-33/ST2 Pathway: Target and Novel Biomarker. *Nat Rev Drug Discov.*, doi:10.1038/nrd2660.
4. LastNameZ, et al. Structure of IL-33 and its interaction with the ST2 and IL-IRAcP receptors--insight into heterotrimeric IL-I signaling complexes. Structure.
5. LastName5, N. LastName6, R., IL-33, an Interleukin-1-like Cytokine that Signals via the IL-I Receptor-Related Protein ST-2, *Immunity*, Volume 123, Issue S, 2005, pages 479-490, ISSN 1074-7613.
6. ExampleAuthor, J. (2009). Keratoconjunctivitis sicca and buccoglossopharyngitis sicca with enlargement of parotid glands; report of two cases of Syndrome A, with study of lacrimal and parotid glands. *Arch Ophthal.*, 1946 doi: 10.1001.

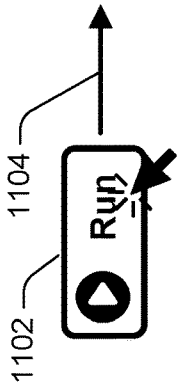

```
                                          ┌─ 2100
                                          ▼
┌─────────────────────────────────────────────────────────────────────┐
│  RECEIVE, VIA A GRAPHICAL USER INTERFACE (GUI) PRESENTED VIA A USER │
│  DEVICE, AN INPUT QUERY THAT IS ASSOCIATED WITH A RESEARCH TOPIC AND│
│        THAT INCLUDES A FIRST CONCEPT AND A SECOND CONCEPT           │
│                              2102                                    │
└─────────────────────────────────────────────────────────────────────┘
                                 │
                                 ▼
┌─────────────────────────────────────────────────────────────────────┐
│  IDENTIFY ONE OR MORE EVIDENCE PASSAGES THAT INCLUDE ONE OR MORE    │
│  SEMANTIC LINKS BETWEEN THE FIRST CONCEPT AND THE SECOND CONCEPT    │
│                              2104                                    │
└─────────────────────────────────────────────────────────────────────┘
                                 │
                                 ▼
┌─────────────────────────────────────────────────────────────────────┐
│ DETERMINE THAT THE ONE OR MORE SEMANTIC LINKS INCLUDE ONE OR MORE   │
│ RELATIONAL REPRESENTATIONS CONNECTING THE FIRST CONCEPT AND THE     │
│                         SECOND CONCEPT                              │
│                              2106                                    │
└─────────────────────────────────────────────────────────────────────┘
                                 │
                                 ▼
┌─────────────────────────────────────────────────────────────────────┐
│ DETERMINE ONE OR MORE RELATION CLUSTERS BY AGGREGATING THE ONE      │
│ OR MORE RELATIONAL REPRESENTATIONS BASED AT LEAST IN PART ON A      │
│ DEGREE OF SEMANTIC SIMILARITY BETWEEN THE ONE OR MORE RELATIONAL    │
│                         REPRESENTATIONS                             │
│                              2108                                    │
└─────────────────────────────────────────────────────────────────────┘
                                 │
                                 ▼
┌─────────────────────────────────────────────────────────────────────┐
│ DETERMINE AN AGGREGATION CONFIDENCE ASSOCIATED WITH A RELATION      │
│ CLUSTER OF THE ONE OR MORE RELATION CLUSTERS, WHEREIN THE           │
│ AGGREGATION CONFIDENCE IS BASED AT LEAST IN PART ON A RELIABILITY   │
│ SCORE OF A PORTION OF THE ONE OR MORE EVIDENCE PASSAGES             │
│                              2110                                    │
└─────────────────────────────────────────────────────────────────────┘
                                 │
                                 ▼
┌─────────────────────────────────────────────────────────────────────┐
│ DETERMINE THAT A QUERY RESULT INCLUDES THE RELATION CLUSTER BASED   │
│ AT LEAST IN PART ON RANKING OF THE ONE OR MORE RELATION CLUSTERS,   │
│ THE RELATION CLUSTER INCLUDING A RELATION EXPRESSION BETWEEN THE    │
│                 FIRST CONCEPT AND THE SECOND CONCEPT                │
│                              2112                                    │
└─────────────────────────────────────────────────────────────────────┘
```

```
RECEIVE A CONCEPT GRAPH INCLUDING ONE OR MORE EVIDENCE LINKS ASSOCIATED
WITH A RESEARCH TOPIC, WHEREIN THE ONE OR MORE EVIDENCE LINKS INCLUDE A
FIRST EVIDENCE LINK INDICATING A FIRST SEMANTIC LINK BETWEEN A FIRST
CONCEPT AND A SECOND CONCEPT, AND A SECOND EVIDENCE LINK INDICATING A
SECOND SEMANTIC LINK BETWEEN THE SECOND CONCEPT AND A THIRD CONCEPT,
AND WHEREIN THE ONE OR MORE EVIDENCE LINKS ARE ASSOCIATED WITH A
KNOWLEDGE REPRESENTATION ASSOCIATED WITH A KNOWLEDGE DOMAIN
2902
```

```
CAUSE DISPLAY OF A VISUAL REPRESENTATION OF THE CONCEPT GRAPH, WHEREIN
THE CONCEPT GRAPH VISUALLY INDICATES THE FIRST CONCEPT, THE SECOND
CONCEPT, AND THE THIRD CONCEPT AS CONCEPT NODES, AND THE FIRST SEMANTIC
LINK AND THE SECOND SEMANTIC LINK AS RELATIONSHIP LINKS, WHEREIN THE
CONCEPT NODES ARE SELECTABLE TO VIEW OF ASSOCIATED PORTIONS OF ONE OR
MORE EVIDENCE PASSAGES
2904
```

```
CAUSE DISPLAY OF ONE OR MORE PROMPTS TO GUIDE USER INPUT FOR THE
RESEARCH
2906
```

FIG. 29

INTERACTIVE RESEARCH ASSISTANT—LIFE SCIENCE

BACKGROUND

A complex research question is a question that may not have a single factual answer and instead multiple possible answers to be supported by chains of evidence across multiple documents rather than a single document. To find such answers, a researcher may perform the arduous task of repeatedly performing a series of steps to search, explore, define, analyze and refine research results until it leads to one of these answers. Before the search, a research process may begin with determining a research topic, including two or three keywords ("concepts") in which to initiate the search. Then, to start the search, the research process may include identifying documents (e.g., books, journals, articles, etc.) mentioning the concepts in relation to each other and/or other related concepts. Next, the research process may require reading through the documents to understand the information and to identify relevant documents. Then the research process may require a more careful reading of the relevant documents to identify bits of evidence that may support arguments or research hypotheses. The research process may require synthesizing information from the bits of evidence to determine if the bits of evidence fit together. Some bits may get discarded. The remaining bits are chained together, forming logical links that may lead to research findings. The research process may repeat until the research findings lead to research results that provide a satisfactory answer for the researcher. Finally, the research process concludes by summarizing the evidence chain in support of the answer. Traditionally, document search to support such a complex research topic may be computationally/resource intensive and time-consuming, often requiring days, weeks, or even months just to identify relevant quality, evidence for support. Such document search may include manually searching for the concepts, reading and re-reading through documents to find evidence that support (or refute) arguments/positions associated with the research topic, connecting the evidence to build a chain of evidence, and repeating the search.

Although modern search engines have made the research process less cumbersome than manually gathering physical documents, such as books, research articles, etc., most popular search engines will only produce a list of single documents for the searched keywords. The list of single documents from the search engines fails to consider that there is a chain of intermediate results that are to be linked together to support the answer, and the intermediate results may be contained in different documents. Moreover, modern search engines fail to discover complex relations between concepts identified in relevant information from the different documents.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

FIG. 11 illustrates an example user interface displaying an example output of summarized evidence generated by the research assistant system, as discussed herein.

FIG. 21 illustrates an example process for a research assistant tool to identify relationship links between concepts supported by evidence, as discussed herein.

FIG. 29 illustrates an example process for a research assistant tool to generate a medical hypothesis based on a search schema as supported by evidence, as discussed herein.

DETAILED DESCRIPTION

Figure 1:
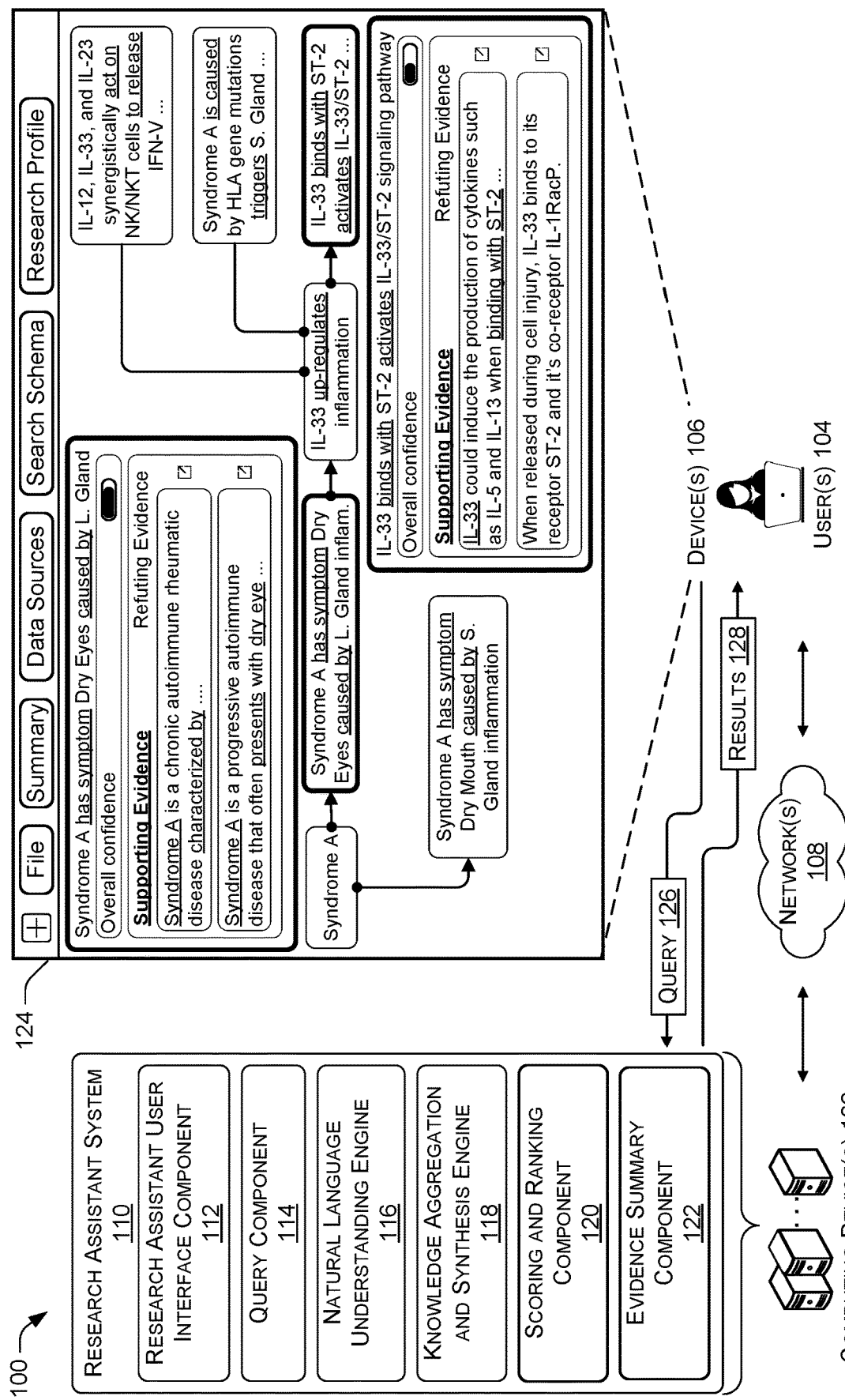
FIG. 1 illustrates an example system including research assistant tools configured with components and a graphical user interface to help conduct research queries.

This disclosure is directed, in part, to a research assistant system including a research assistant tool and associated components and a graphical user interface to guide user input to research, discover, and evidence answers for complex research questions. The research assistant system may include the graphical user interface ("GUI" or "user interface") for presentation on a user device associated with a user. The user interface may provide prompts and guidance for collaboration and exploration of research concepts iteratively. A concept may include a search term, entities, and/or propositions/statements.

The research assistant tool may include components to assist the user in exploring the research topic by modeling and automating portions of a research process. The research assistant tool may perform research steps including searching, analyzing, connecting, aggregating, synthesizing, inferring, and chaining together evidence gathered from a diverse set of knowledge sources. Non-limiting examples of the knowledge sources may include unstructured, semi-structured, and structured knowledge (e.g., medical ontologies, knowledge graphs, research papers, clinical studies, etc.).

The research assistant tool may construct individual evidence links and/or build a chain of evidence by connecting the evidence links. For instance, the research assistant tool may guide a user to discover a single evidence link by searching for related terms such as, "What does A relate to?" Or "Is A related to B?" in response, the research engine may determine that "A relates to B" based on three articles found that supports this answer. The user may select that answer, and confirm the articles support the answer, and the system may store "A relates to B" as an evidence link including links to the articles. In some examples, the evidence link may be stored in a structured database for queries that may require connecting evidence links. The research assistant tool may present prompts to guide user interaction to expand an evidence chain to the next concept of interest. For instance, the next suggested query may be, "What does B relate to?" To discover that, "B relates to C." In various examples, the new evidence link, "B relates to C," may also be stored in the structured database. In additional and/or alternative examples, an evidence link may also be referred herein as a "proposition," which may include a declarative statement with a truth value (e.g., true or false) and may define a connection between two concepts (e.g., "B induces C"). As will be described herein, complex propositions ("propositionals") may be generated by aggregating evidence links using a machine learning model and/or an inference engine. A proposition may include two or more concepts and/or propositions that are logically connected.

The research assistant tool may configure an inference engine to use the evidence links stored in the structured database to construct a chain of evidence. For instance, an input query may ask, "Is A related to D?" A traditional search engine may search for "A+D" and find nothing that mentions A and D together. However, the research assistant tool may find articles with "A relates to B" and "C relates to D" and may leverage evidence links stored in the structured database and apply the inference engine to create an evidence chain of "A relates to B," "B relates to C," and "C relates to D". In a non-limiting example, an example propositional may include if "A relates to B" and "B relates to C" and "C relates to D", then "A relates to D." In various examples, the research assistant tool may request user feedback (e.g., thumbs up or thumbs down) for the supporting/refuting evidence for a proposition and the user input can provide feedback on each instance of the link (e.g., first evidence link(s) for "A relates to B," second evidence link(s) for "B relates to C," etc.).

In some examples, the components may include but are not limited to a query component, a natural language understanding engine, and a knowledge aggregation and synthesis engine.

In some examples, the user interface may present prompts for receiving user input associated with a research query. The user interface may be configured to guide the user input to iteratively explore evidentiary chains to connect the concepts through a large body of knowledge comprising natural language text (e.g., journals, literature, documents, knowledge base, databases, etc.).

The research assistant tool may configure the query component to receive and process a research query. The research query ("input query") may be received as a structured query or an unstructured query (e.g., a natural language question).

The query component may include a semantic search engine to process the input query and search for concepts in a text corpus. The research assistant tool and/or the query component may generate a "research results graph" or any data structure to store gathered research data ("findings").

In some examples, the query component may receive an input query that includes a natural language question and use a semantic parser to convert the natural language question to a structured question. The semantic parser may parse the text of the natural language question and convert the text into machine language (e.g., structured representation), which is a machine-understandable representation of the meaning of the text. The system may apply any semantic parsing models and/or schema "PropBank") to organize the converted data. In some examples, the structured representation of the question may be included with the query graph.

The query component may serve as an exploration tool to explore concepts or relations based on the input query. In some examples, the input query may specify two primary concepts, including a starting point/concept and an ending point/concept. The exploration tool may explore different relation links found between two primary concepts. In additional and/or alternative examples, the question may include a primary concept and a relation for exploring; and the exploration tool may explore nodes having that relation link with the primary concept.

In some examples, the semantic search engine may include a knowledge representation of a domain ("domain theory") and associated text corpus for performing a search. The search may include keyword(s) (e.g., the input concept and/or relations) search in documentations and passages, web search, and embedded search for terms beyond explicit keywords. An embedded search may include inferred information extracted from documentations and passages. The query component may output query results with evidentiary passages for the natural language understanding engine to process the query results.

The natural language understanding (NW) engine may receive and translate the query results into machine-readable structured representations of the query results. To translate the query results, the NLU engine generates a multi-dimensional interpretation of the query results. The process of generating that multi-dimensional interpretation may include semantic parsing, semantic fit detection, and polarity detection. The NUJ engine may configure a semantic parser to "read and understand" the query results by semantically analyzing the evidentiary passages and constructing structured models ("semantic structures," "structure representations," or "knowledge representations") to represent the interpreted information into logical structures to convey the meaning. The semantic parser may parse the evidentiary passages to discover relations connecting concepts and generate knowledge representations to store the information.

Additionally, the system may configure the semantic parser to use semantic indicators to further qualify semantic relations. The semantic parser may use a relational qualification schema (RQS) to describe or qualify a set of conditions under which a relation may be true. In some examples, the system may configure one or more sets of semantic indicators with conditionals relevant to a specific knowledge domain ("domain"). In machine language, a relation is a named semantic link between concepts (may include individual search terms, entities, propositions and/or statements), and relations are verb-senses with multiple name roles. Natural human language has words with multiple inferred meanings, while machine language looks for a direct match; thus, knowledge representation allows for a machine to read the same word and correctly interpret the meaning. A word may have multiple meanings that is inferable by a human researcher, but not for a machine. Thus, the NUJ engine may model a relation link as a semantic link. A semantic link is a relational representation that connects two representations (e.g., concepts). The relational representation supports interpretation and reasoning with other links and facilitates predictive operations on representations. By representing the "relation" term as a semantic link, when the machine reads the semantic link, it may also determine that other semantically similar terms can be inferred as having similar meaning. The present system may use this process of "determining that other semantically similar terms can be inferred as having similar meaning" to aggregate the semantically similar terms into groups ("clusters"). This aggregation process may be referred to herein as clustering. The semantic parser may generate the interpreted query results by interpreting the query results in a semantic schema, which is the semantic representation with constructed semantic indicators. The semantic schema may map interpreted concepts to "concept type" and interpreted relations to "semantic type." Accordingly, the present system configures a semantic parser that may analyze the evidentiary passages and construct structured representations with semantic schema to store the information.

The semantic fit detection may check the interpreted query results against any explicit or unnamed type constraints set by the input query and may check that the semantic type in the input query matches that of the interpreted query results. The polarity detection may include refuting evidence. In some examples, the NLU engine may use a domain-independent interpretation schema for the interpretation process. The interpretation process for a machine is to build knowledge representation of the text and represent the key concepts and relations between the decision variables in some formal manner, typically within a framework such as semantic schema. The NLU engine may output interpreted query results. The interpreted query results may include interpreted relation results and/or interpreted concept results with evidence texts.

The research assistant tool may configure the knowledge aggregation and synthesis engine for processing the interpreted query results with evidence texts. The knowledge aggregation and synthesis engine may apply clustering and similarity algorithms to aggregate information in the interpreted query results. The clustering and similarity algorithms may determine to group text in the interpreted relation results and/or interpreted concept results based on a high degree of similarity. In some examples, the clustering and similarity algorithms may determine to cluster semantic relations and their associated arguments based on the similarity between relations and/or concepts. The similarity may be determined based on using a thesaurus and/or word embeddings. The clustering and similarity algorithms may determine a set of relation occurrences and combine the set to a single relational instance to generate a cluster. In some examples, the clustering and similarity algorithms may output aggregate confidence associated with evidence texts that support the cluster. The aggregate confidence may be based on the relevance score of the evidence texts. The aggregated query results may include clusters with annotated evidence texts.

The knowledge aggregation and synthesis engine may determine to perform analysis on the aggregated query results with processes including originality detection, saliency computation, and authorship analysis. The originality detection may determine a count for knowledge source, wherein a lower count value is associated with higher originality. The originality detection may determine that a piece of evidence has been duplicated and/or sourced from the same place as another evidence text. The saliency computation determines a prominence in corpus and may be based at least in part on as frequency of the source. The saliency computation may determine confidence in count and relevance and/or could be defined by the user. The authorship analysis may determine the credibility of the author. The knowledge aggregation and synthesis engine may output aggregated query results with annotated evidence passages.

In some examples, the research assistant system may include a scoring and ranking component to receive and rank the aggregated query results. The aggregated query, results may include at least one of: a concept cluster, a relation cluster, or a propositional cluster. As will be described in greater details herein, a proposition includes a statement defining one or more connections between concepts Wherein the concepts may include individual search terms, entities, propositions and/or statements. The scoring and ranking component may apply one or more ranking algorithms to rank the clusters by various features. The ranking algorithms may also include the scores from one or more features (originality score, saliency, authorship). For example, the ranking algorithm may include a top K elements pattern that returns a given number of the most frequent/largest/smallest elements in a given set.

In various examples, the research assistant system may include an evidence summary component for processing the ranked query results with evidence texts. The evidence summary component may process the ranked aggregate results with the evidence texts to generate results data, including results clusters annotated with the related portion of evidence texts. The results clusters include at least one concept cluster, a relation cluster, or a propositional cluster. Each cluster may include a link to summarized evidence passages. The results data may be presented to a user via the user interface to verify whether the cluster is correct or incorrect. The input query and results data are marked as true positives or false positives for training the different components of the system.

The present research assistant system provides a number of advantages over the traditional document search systems. Such advantages include providing a tool to address a research question rather than a document query and providing an evidentiary chain rather than a hit list that merely identifies potential documents or sources that could potentially be relevant to a search. For example, the research assistant system is able to search for complex answers for a complex research question, while the traditional document search system merely performs a simple document query. The research assistant system is a feature-rich tool that allows a user to build a case, argument, and/or evidentiary chain rather than simply search for a document. Additionally, the research assistant system may generate complex hypotheses about relationships between research concepts that may be true under different conditions. The research assistant system may deconstruct a natural language research question to construct and interactively execute an iterative guided search.

Additionally, the research assistant system provides the advantages of avoiding confirmation biases. Traditional document search is designed to find documents with given keywords and can lead to a strong confirmation bias. In contrast, for any given link in an evidentiary chain, the research assistant system looks for and discovers supporting and refuting evidence. Furthermore, both supporting evidence and refining evidence may be weighted to produce summary confidence that considers reliability, redundancy, and originality.

Moreover, the research assistant system provides the advantages of noise suppression and expert knowledge. In traditional document search, redundancy can falsely lead to increased confidence. Such traditional search hits may yield a similar result originating from a single, possibly unreliable source. The research assistant system generates an originality score that modulates the effect of redundancy from the same original source. Traditional search can only be affected by keywords in the query. In contrast, the research assistant system incorporates expert knowledge about the research domain through reusable causal chain schemas. A causal chain schema may include search parameters that defines search patterns to find "causal chains." The search patterns may refine the search to: (1) identify any relationships between concepts and/or (2) determine a cause and effect relationship between concepts. For instance, a causal chain schema may be found in the previous example, "Is A related to D?" In this examples, the causal chain may include, "A is related to D because A is related to B, and B is related to C, and C is related to D." The causal chain schema is a simple, reusable structure that instructs the research assistant system on the best ways to connect the dots in different domains. In some examples, an expert first researcher may define a causal chain schema that produces positive search results and may save the causal chain schema to pass along to a junior second researcher to further refine the research.

Furthermore, the research assistant system includes evidentiary chaining and multi-step search, which increases the efficiency of the research process. The traditional document search system merely provides a list of single documents and fails to provide evidentiary chains and multi-step search. In contrast, the research assistant system may guide a multi-step search by iteratively exploring evidentiary chains. Each search leads to another "link" in the evidentiary chain. These links are discovered as search results are parsed, qualified, and used to set up and execute a series of searches, guided by user input, to iteratively constructive evidentiary chains. This increases the efficiency of the research process, including researching, discovering, and evidencing answers to complex, high-impact questions in minutes versus the lengthy time (e.g., days/weeks/months) for manual literature review using traditional document search engines and finding evidentiary chains across documents. Thus, the present research assistant system provides improvement over traditional search systems by providing a faster, more efficient, and less costly method to conduct research. By decreasing the overall time spent to conduct research, the research assistant system reduces network bandwidth usage, reduces computational processing of computing systems that receive a search input and searches, analyzes and produces results for the search input, and further reduces network resources usage.

In addition to the technical improvements over the traditional document search engine, the research assistant system is a system that accumulates knowledge and improves from continued use and feedback on search results. For example, as described herein, the present research assistant system may search for documents and convert the text to machine language and store the knowledge representation of the evidence documents in a local database and/or as a temporary cache. Document searches for complex research questions often find the same documents repeatedly. By storing processed documents locally, the present system can reduce computations processing, increase network bandwidth, and reduce latency. In particular, the system will not have to re-download additional copies of the same article from the journal database and will not have to re-process the article. Additionally, as described herein, the present system may request user feedback (e.g., thumbs up or thumbs down) for supporting/refuting evidence for a proposition. The system can use this feedback to (1) dynamically re-rank the list of evidence passages and provide immediate visual feedback by removing the evidence passage with negative feedback and up-ranking the evidence passage with positive feedback; and (2) aggregate the feedback across multiple users and use the aggregated data as training data for the next iteration of model training. Accordingly, the research assistant system may improve upon itself from use and to continuously reduce network bandwidth usage, reduce computational processing of computing systems that receive a search input and searches, analyzes and produce results for the search input, and further reduce network resources usage. These and other improvements to the functioning of a computer and network are discussed herein.

Examples of a natural language understanding engine and associated components, including knowledge representation and reasoning engine, knowledge induction engine, knowledge accumulation engine, semantic parser, and other techniques, are discussed in U.S. Patent No. 10,606,952, filed Jun. 24, 2016. Examples of a natural language understanding engine and associated components, including knowledge acquisition engine, semantic parser, and other techniques, are discussed in U.S. patent application Ser. No. 17/021,999, filed Aug. 8, 2020. Examples of a natural language understanding engine and associated components, including reasoning engine, semantic parser, inference engine, and other techniques, are discussed in U.S. patent application Ser. No. 17/009,629, filed Aug. 1, 2020. Application Ser. Nos. 17/021,999 and 17/009,629 and U.S. Pat. No. 10,606,952 are herein incorporated by reference, in their entirety, and for all purposes.

It is to be appreciated that although the instant application includes many examples and illustrations of conducting research in the life science domain, the research assistant system is configured to be used with research across any domain. In particular, the use of the research assistant system within the life science domain is a non-limiting example of how the present system can be used to assist in conducting research.

The techniques and systems described herein may be implemented in a number of ways. Example implementations are provided below with reference to the following figures.

Illustrative Environment

FIG. 1 illustrates an example system 100, including a research assistant tool configured with components and a graphical user interface to help to conduct research queries. The system 100 may include user(s) 104 that utilizes device(s) 106, through one or more network(s) 108, to interact with the computing device(s) 102. In some examples, the network(s) 108 may be any type of network known in the art, such as the Internet. Moreover, the computing device(s) 102 and/or the device(s) 106 may be communicatively coupled to the networks) 108 in any manner, such as by a wired or wireless connection.

The research assistant system 110 may include any components that may be used to facilitate interaction between the computing device(s) 102 and the device(s) 106 to assist in a research process. For example, the research assistant system 110 may include a research assistant user interface (UI) component 112, a query component 114, a natural language understanding (NUJ) engine 116, a knowledge aggregation and synthesis engine 118, a scoring and ranking component 120, and an evidence summary component 122. As described herein, the research process may include a series of research steps, including, but not limited to: receiving a research topic as an input query, searching for documents/text related to the input query (i.e., "information"), parsing the evidence documents/text to understand the information, synthesizing the information to identify relevant evidence, linking the evidence together to find logical reasoning to support research results, and repeating the research process until the research results provide reasoning in support of possible answers and then summarizing the evidence to support the best answer. The research assistant system 110 and associated components may automate most of the research process and require only minimal user interactions to initiate a query then expand an evidence chain to the next concept of interest to continuously explore a research topic.

The research assistant UI component 112 may generate a graphical user interface to provide guidance and prompts to collaborate with the user(s) 104 to explore a research topic. In some instances, the research assistant UI component 112 can correspond to the research assistant UI component 208 of FIG. 2, where features may be described in greater detail. The process to generate the user interface, including present example user interface 124 and other example user interfaces, to provide guidance and will be described herein with more detail with respect to FIGS. 6-20. In some examples, the user interface may include a prompt for entering a search schema to explore the research topic. The search schema may define one or more search keywords and/or parameters including, but not limited, a starting concept ("specific concept," or "source concept"), a generic concept, an ending concept ("target concept"), a relation link between specified concepts, a relation for exploring relative to a specified concept, and a search constraint type. As described herein, a concept includes any individual search terms, generic concept type, entities, propositions, and/or statements related to the research topic. A relation is a named semantic link between concepts. The answer is evidenced by a chain of relationships between a starting concept and an ending concept, with connective interim concepts that are not part of the question but discovered during research. The research assistant UI component 112 may configure prompts for the user(s) 104 to iteratively explore evidence to discover relations in the causal path and connect concepts.

The research assistant UI component 112 may generate a user interface to guide user input to enter the query and explore the evidence chains. In some examples, the research assistant 7I component 112 may configure the user interface to guide the user input and repeat the research process by iteratively exploring evidentiary chains to connect the dots through a large body of knowledge ("data sources"), including natural language text (e.g., journals, literature, documents, knowledge base, market research documents, and/or structured databases).

In some examples, the research assistant UI component 112 may receive user input for specifying an input query and call the query component 114 to process the input query. In various examples, an input query can be as simple as a single word (e.g., "syndrome") for a concept to explore or may include a phrase (e.g., "What cytokines are induced by IL-33 in Sjogren's Syndrome?").

The query component 114 may receive an input query and perform a search based on the input query. In some instances, the query component 114 can correspond to the query component 210 of FIG. 2, where features may be described in greater detail. The input query may be received as a structured data format ("structured query"), unstructured data format ("unstructured query" or "natural language question"), and/or a search schema. The query component 114 may generate a query graph ("research results graph") to store search results ("findings") for an iterative exploration of the input query. The query graph may include a concept map ("research results map") that links a starting concept to other concepts (or concept to propositon, or proposition to proposition") and examines the relationships between concepts. The research assistant UI component 112 may generate a visual representation for the query graph and may indicate "concepts" and/or "propositions" as nodes and "relations" as links or edges that connect the concepts and/or propositions.

In some examples, query component 114 may determine the search engine and/or process based on the data format of the input query. In various examples, the input query includes an unstructured query with a natural language question, and the query component 114 may use a semantic parser to convert the natural language question to a structured representation for the input query. The structured representation of the input query may be associated with the query graph.

For example, a natural language question (unstructured query) may be entered as:

"What cytokines are induced by IL-33 in Sjogren's Syndrome?

While the structured query equivalent may be entered as:
C2=Sjogrens Syndromes
C3=IL-33
R=induced by
?C=What
Type constraint on ?C=cytokine In additional and/or alternative examples, the input query includes a structured query, and the query component 114 may search a structured database or knowledge graph to output query results.

In various examples, query component 114 may include a semantic search engine to search for concepts in a text corpus. The semantic search engine may search for evidentiary passages from document search engines or embedded searches.

In some examples, the query component 114 may receive an input query including a search schema. The search schema may specify search parameters for conducting the search. In a non-limiting example, the search parameters may include search terms, search filters, search conditions, search process, and the like. The search terms may include keywords used for a document search engine and may include "concepts," "relationships," and/or propositions. As described herein, the present research assistant tool may be integrated with different applications for users and/or researchers of varying levels of sophistication and search needs, and the search schema may include a variety of search parameters to meet these needs.

The query component 114 may receive different search parameters and may perform different search processes in response. For instance, the search schema may specify two "primary concepts," and the system may explore possible "multi-hop" links between the two primary concepts. A multi-hop link ("multilink") includes one or more intermediate concepts between the two primary concepts. Alternatively, and/or additional, the search schema may specify a causal schema to search for a causal pathway with a starting point ("source concept") and connected to an ending point ("target concept"). The causal pathway may be a multi-hop link with one or more intermediate concepts between the starting and ending points. The system may explore different possible causal pathways with different intermediate links and/or intermediate concepts starting from a source concept and ending at the target concept. This may be done by guiding a user to iteratively select the intermediate links and/or intermediate concepts or may be automatically generated by the system using an inference engine. After generating a causal pathway, the system may verify that there are complete connecting evidence links starting from the source concept and ending at the target concept.

In additional and/or alternative examples, the search schema may define a primary concept and a relation for exploring, and the query component 114 may explore new concepts that have the relation link to the primary concept. The query component 114 may configure exploration tools, including a concept exploration tool or a relationship exploration tool based on the input query. As described herein, an answer to a complex research question may be inferred by a sequence of connected statements, each occurring in different documents in the corpora where no one statement or one document contains the answer. The query component 114 may use the semantic search engine to search for and construct the sequence of connected statements beginning with the starting concept and terminating at the ending concept. The sequence of connected statements may include a sequence of relationships linking concepts.

In some examples, the semantic search engine may include a domain theory and associated text corpus for performing a search. The search may include a keyword (e.g., the input concept and/or relations) search in documentations and passages, web search, and embedded search for terms beyond explicit keywords. The query component 114 may output query results, including one or more evidentiary passages and/or knowledge graphs, and call the natural language understanding engine to interpret the query results.

The natural language understanding (NLU) engine 116 may receive and process the query results. In some instances, the NLU engine 116 can correspond to the NLU engine 216 of FIG. 2, where features may be described in greater detail. The NLU engine 116 may apply a multi-dimensional interpretation process with a domain-independent interpretation schema to analyze the query results. The multi-dimensional interpretation process may include semantic parsing, semantic fit detection, and polarity detection.

The NLU engine 116 may use a semantic parser to analyze the query results by semantically parsing the evidentiary passages and generating interpreted query results. The semantic parser may parse the evidentiary passages to discover relations connecting concepts and construct a set of semantic indicators that qualify the occurrences of the relations. The semantic parser may use a relational qualification schema (RQS) to describe or qualify a set of conditions under which a relation may be true. The semantic parser may generate the interpreted query results by interpreting the query results in a semantic schema, including the constructed set of semantic indicators. The semantic schema may map interpreted concepts to "concept type" and interpreted relations to "semantic type."

The NLU engine 116 may use the semantic fit detection to check the interpreted query results against any explicit or unnamed type constraints set by the input query and check that the semantic type in the input query matches that of the interpreted query results. The polarity detection may identify refuting evidentiary passages with semantic context. In some examples, the NIX engine 116 may use a domain-independent interpretation schema for the interpretation process. The NLU engine 116 may output interpreted query results. The interpreted query results may include interpreted relation results and/or interpreted concept results with evidence texts.

The knowledge aggregation and synthesis engine 118 may receive and process the interpreted query results with evidence texts. In some instances, the knowledge aggregation and synthesis engine 118 can correspond to the knowledge aggregation and synthesis engine 224 of FIG. 2, where features may be described in greater detail. The knowledge aggregation and synthesis engine 118 may apply clustering and similarity algorithms to aggregate information in the interpreted query results. The clustering and similarity algorithms may determine to group text in the interpreted relation results and/or interpreted concept results based on a high degree of similarity. In some examples, the clustering and similarity algorithms may determine to cluster semantic relations and their associated arguments based on the similarity between relations and/or concepts. The similarity may be determined based on using a thesaurus and/or word embeddings. The clustering and similarity algorithms may determine a set of relation occurrences and combine the set to a single relational instance to generate a cluster. In some examples, the clustering and similarity algorithms may output aggregate confidence associated with evidence texts that support the cluster. The aggregate confidence may be based on the relevance score of the evidence texts. The aggregated query results may include clusters with annotated evidence texts.

The knowledge aggregation and synthesis engine 118 may determine to perform analysis on the aggregated query results with processes including originality detection, saliency computation, and authorship analysis. The originality detection may determine a count for knowledge source, wherein a lower count value is associated with higher originality. The originality detection may determine that a piece of evidence has been duplicated and/or sourced from the same place (e.g., source, location, reference, etc.) as another evidence text. The saliency computation determines a prominence in corpus and may be based at least in part on as frequency of the source. The saliency computation may determine confidence in count and relevance and/or could be defined by the user. The authorship analysis may determine the credibility of the author of the source/document. The knowledge aggregation and synthesis engine 118 may output aggregated query results with annotated evidence passages.

The scoring and ranking component 120 may receive and rank the aggregated query results. The aggregated query results may include at least one of: a concept cluster, a relation cluster, or a propositional cluster. The scoring and ranking component 120 may apply one or more ranking algorithm to rank the clusters by various features. For example, the ranking algorithm may include a top K elements pattern that returns a given number of the most frequent/largest/smallest elements in a given set. The scoring and ranking component 120 may output the ranked aggregate results with the evidence texts.

The evidence summary component 122 may process the ranked aggregate results with the evidence texts. The evidence summary component 122 may process the ranked aggregate results with the evidence texts to generate results data, including one or more result clusters annotated with the related portion of evidence texts. The one or more result clusters include at least one concept cluster, a relation cluster, and a propositional cluster, Each cluster of the one or more result clusters annotated with the related portion of evidence texts includes a link to a summarized evidence passage. The results data may be presented to a user(s) 104 via a user interface (e.g., example user interface 124) to verify whether at least one cluster is correct or incorrect. The input query and results data are marked as true positives or false positives and saved, by the research assistant system 110, as training data for training the different components of the system.

The user(s) 104, via the device(s) 106, may interact with the computing device(s) 102. The users) 104 may include any entity, individuals, researchers, writers, analysts, students, professors, and the like. In various examples, the user(s) 104 may include formal collaborators and/or researchers who conduct research on behalf of an entity. The user(s) 104 may be prompted by the system to generate training data, including marking generated results as correct or incorrect (e.g., thumbs up or thumbs down). The generated results may include any system generated results including, but not limited to, evidence passages found in response to input queries, causal links inferred by the system, propositions and/or hypothesis generated by the system, and the like. This user feedback and other user interactions may be used by the research assistant system 110 to continuously learn and improve generated results. In additional examples, the user(s) 104 may be part of an organized crowdsourcing network, such as the Mechanical Turk™ crowdsourcing platform.

The user(s) 104 may operate the corresponding device(s) 106 to perform various functions associated with the device(s) 106, which may include at least some of the operations and/or components discussed above with respect to the computing device(s) 102. The users may operate the device(s) 106 using any input/output devices, including but not limited to mouse, monitors, displays, augmented glasses, keyboard, cameras, microphones, speakers, and headsets. In various examples, the computing device(s) 102 and/or the device(s) 106 may include a text-to-speech component that may allow the computing device(s) 102 to conduct a dialog session with the user(s) 104 by verbal dialog.

The device(s) 106 may receive content from the computing device(s) 102, including user interfaces to interact with the user(s) 104. In some examples, the user(s) 104 may include any number of human collaborators who are engaged by the devices) 106 to interact with the computing device(s) 102 and verify the functions of one or more components of the computing device(s) 102. For instance, a human collaborator of the device(s) 106 may interact with the research assistant system 110, and the device(s) 106 may receive a list of evidence passages that the system may present as supporting/refuting evidence for a proposition and/or an input query. In the present example; the user(s) 104 may be presented the list of evidence passages, via a user interface, and may be asked to provide a positive or negative feedback (e.g., thumbs up or thumbs down) about whether the content of the evidence passages provides the indicated "supporting evidence" or "refuting evidence." In some examples, in response to an input query with a causal search schema, the research assistant system 110 may automatically identify and present one or more potential causal pathway(s) (e.g., with one or more different interim concepts) to the query with a list of causal links, and the user(s) 104 may be asked to verify whether the each causal link was correct or incorrect based on the evidence passages cited for the causal link. The feedback and associated query data, generated results, and/or evidence passages may be stored to help train the system. Additionally, as described herein, the system can use the feedback to (1) dynamically re-rank the list of evidence passages and provide immediate visual feedback by removing the evidence passage with negative feedback and/or up-ranking the evidence passage with positive feedback; and (2) aggregate the feedback across multiple users and use the aggregated data as training data for the next iteration of model training.

In a non-limiting example, a research assistant system 110 may include a research assistant UI component 112 to generate an example user interface (UI) 124 to interact with a device(s) 106 associated with the user(s) 104. The research assistant system 110 may receive example input query 126 from the device(s) 106 and, in response, transmit example query results 128.

As described herein, the research process is a repetitive process of searching, receiving information, and synthesizing information, and the research assistant system 110 may assist by repeating the process of receiving the example input query 126 and transmitting the example query results 128.

In a non-limiting example, the research assistant UI component 112 may generate the example user interface (UI) 124 to prompt the user(s) 104 to provide an example input query 126 to begin the research process. As depicted, the input query 126 may initially-include a search schema defining a specific concept of "Syndrome A" and relation of "has symptom."

The query component 114 receives the input query 126 and may conduct a search for the explicit search term "Syndrome A" and search for any articles expressing some symptom of "Syndrome A." As a non-limiting example, the query component 114 may find 100 articles about the different symptoms of "Syndrome A." These 100 articles are the "evidentiary passages" of the different symptoms. The evidentiary passages are the "query results," and the query component 114 may output the query results to a natural language understanding (NLU) engine 116 for processing.

The NLU engine 116 may receive the query results and process the information received as natural language into machine understandable language. As described herein, the present NLU engine 116 may configure a semantic parser to analyze the evidentiary passages and construct structured semantic representations with a semantic schema to store the information. In the present non-limiting example, the NUJ engine 116 may receive the 100 articles and use the semantic parser to analyze and interpret the content of the articles into structured semantic representations. The structured query results may be the interpreted query results. The NLU engine 116 may output the interpreted query results for the knowledge aggregation and synthesis engine 118.

The knowledge aggregation and synthesis engine 118 may receive the interpreted query results and aggregate the interpreted evidence. As described herein, the knowledge aggregation and synthesis engine 118 may rank the knowledge based on aggregating the information and may score the evidence-based on features metrics. The natural language understanding (NW) engine 116 and the knowledge aggregation and synthesis engine 118 may determine scores for features, including but not limited to aggregation confidence, saliency, relevance, originality, author credibility, and the like. In the present non-limiting example, the knowledge aggregation and synthesis engine 118 may receive the interpreted query results for the 100 articles and apply a clustering and similarity algorithm to cluster the information. For instance, the 100 articles may only express five different symptoms of "Syndrome A," and the clustering and similarity algorithm may group the similar concepts, which are the five similar symptoms, together to generate "concept clusters" and thus, forming five symptom clusters. Each cluster would include links to their respective articles. The concept clusters are the search results from searching for "Syndrome A," with the relation "has symptom."

In some examples, the knowledge aggregation and synthesis engine 118 may rank the concept clusters and present them in ranked order, Assuming the 100 articles describe five different symptoms, they may have "dry eyes" and "dry mouth" as the top two concept clusters. The clustering and similarity algorithm may use one or more features to score each cluster. The clustering and similarity algorithm may count the number of articles combined into a cluster. For example, "dry eyes" may be expressed in 75 articles, while "dry mouth" was mentioned in 50 articles. A concept cluster for the concept "dry eyes" may include links to the 75 articles and may include a score based on the count of occurrence 75 or a ratio of 75 occurrences within 100 articles. Alternatively, and/or additionally, the clustering and similarity algorithm may output an aggregation confidence score with each cluster based on a confidence that every member of the cluster is similar or equivalent. This is a machine classification score. For instance, if one of the 50 articles in the cluster with "dry mouth" actually said "cotton mouth," the clustering and similarity algorithm may determine that it has a 95% confidence that the classification of "dry mouth" is correct. This 95% confidence may be factored in with the other 49 members of the cluster. The knowledge aggregation and synthesis engine 118 may configure additional models to score the relevance of evidence for each cluster based on a number of features. The knowledge aggregation and synthesis engine 118 may output aggregated query results ("results clusters") to the scoring and ranking component 120.

The scoring and ranking component 120 may receive the aggregated query results and determine an overall ranking for the results clusters. As described herein, each cluster may be scored based on a member count, aggregation confidence, and evidence features, the scoring and ranking component 120 may apply a weight to the different scores and generate a ranking for the clusters and output ranked query results. The evidence and summary component 122 may receive the ranked query results and annotate each cluster with a summary of the linked evidence passages. The example query results 128 may transmit the example query results 128 with annotated evidentiary passages.

The remaining content illustrated in the example UI 124 will be described herein in more detail with respect to FIG. 10.

In the present example, the research assistant system 110 may interact with the device(s) 106 to receive additional example input query 126 to repeat/continue the research process. The query component 114 may receive and process the example input query 126.

The knowledge aggregation and synthesis engine 118 may continue to receive the interpreted query results and aggregate the interpreted evidence. In some examples, the knowledge aggregation and synthesis engine 118 may rank the knowledge based on aggregating the information and may score the evidence-based on features metrics. The natural language understanding (NLU) engine 116 and the knowledge aggregation and synthesis engine 118 may determine scores for features, including but not limited to aggregation confidence, saliency, relevance, originality, author credibility, and the like. The knowledge aggregation and synthesis engine 118 may output aggregated query results.

The scoring and ranking component 120 may continue to receive the aggregated query results and determine an overall ranking for the results clusters. The evidence and summary component 122 may output the ranked query results with summarized evidence passages. The example query results 128 may include results data with summarized evidentiary passages.

In the present example, the user(s) 104 has been interacting with the research assistant system 110 and exploring the relations of "has symptom" and is viewing first supporting evidence for "Syndrome A has symptom Dry Eyes caused by L. Gland." Additionally, the user(s) 104 has is viewing a second supporting evidence for "IL-33 binds with ST-2 activates IL-33/ST-2 signaling pathway." As depicted in the example UI 124, the research assistant system 110 has higher overall confidence in the first supporting evidence.

In the present non-limiting example, when the user(s) 104 is done with her research and wishes to generate a document summary of her research, the user(s) 104 may request the final document from the research assistant system 110. The process to generate the document summary will be described herein in more detail with respect to FIG. 11.

The research assistant system 110 may present the document summary in the example UI 124 to the user(s) 104. The research assistant system 110 may prompt the user(s) 104 to provide negative or positive feedback for evidence listed in the example query results 128. Based on the feedback received from the user(s) 104, the system may store the example input query 126 with the example query results 128 and associated feedback to improve the NUJ engine 116, the knowledge aggregation and synthesis engine 118, the scoring and ranking component 120, the research assistant system 110 and/or other associated components.

Figure 2:
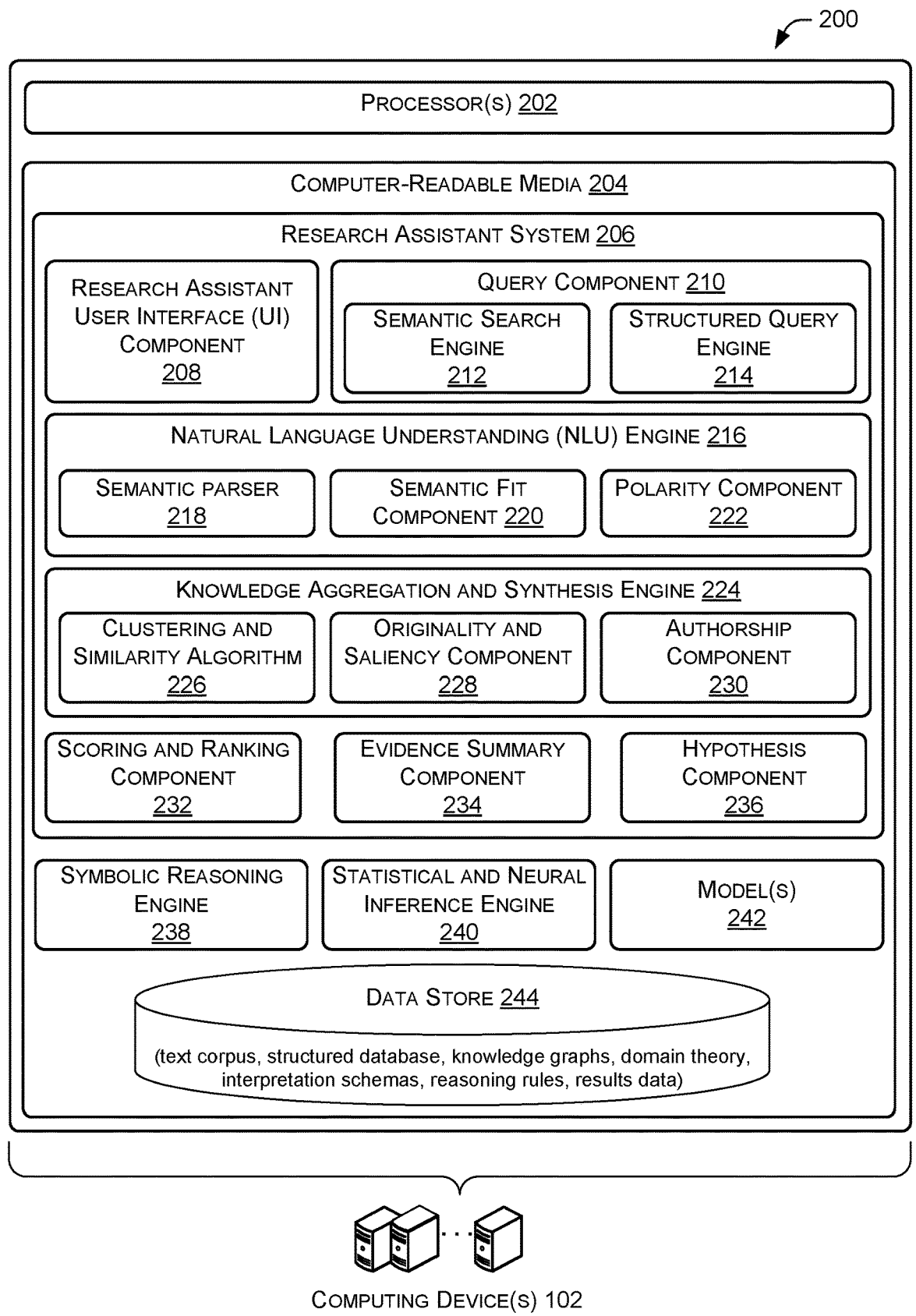
FIG. 2 is a block diagram of an illustrative computing architecture of a research assistant system.

FIG. 2 is a block diagram of an illustrative computing architecture 200 of the computing device(s) 102 of FIG. 1. The computing architecture 200 may be implemented in a distributed or non-distributed computing environment.

The computing architecture 200 may include one or more processors 202 and one or more computer-readable media 204 that stores various modules, data structures, applications, programs, or other data. The computer-readable media 204 may include instructions that, when executed by one or more processors 202, cause the processors to perform the operations described herein for the system 100.

The computer-readable media 204 may include non-transitory computer-readable storage media, which may include hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of storage media appropriate for storing electronic instructions. In addition, in some embodiments, the computer-readable media 204 may include a transitory computer-readable signal (in compressed or uncompressed form). Examples of computer-readable signals, whether modulated using a carrier or not, include, but are not limited to, signals that a computer system hosting or running a computer program may be configured to access, including signals downloaded through the Internet or other networks. The order in which the operations are described is not intended to be construed as a limitation, and any number of the described operations may be combined in any order and/or in parallel to implement the process. Furthermore, the operations described below may be implemented on a single device or multiple devices.

In some embodiments, the computer-readable media 204 may store a research assistant system 206 and associated components, a symbolic reasoning engine 238, a statistical and neural inference engine 240, model(s) 242, and data store 244, which are described in turn. The components may be stored together or in a distributed arrangement.

The research assistant system 206 may include a research assistant user interface (UI) component 208, a query component 210 and associated components, a natural language understanding (NLU) engine 216 and associated components, a knowledge aggregation and synthesis engine 224 and associated components, a scoring and ranking component 232, an evidence summary component 234, and a hypothesis component 236. The research assistant system 206 and associated components may automate most of the research process and require only minimal user interactions to initiate a query, then expand an evidence chain to the next concept of interest to continuously explore a research topic, as described herein. The research assistant system 206 may leverage its components, the model(s) 242, and the data store 244 to build and evolve the knowledge base of static and inference rules and a database of structured knowledge graphs. The research assistant system 206 may collect natural language data, Relational Qualification Schema (RQS), retrieve generated query graphs, save structured query results with evidence data, and inferred chains as needed by the components. In various examples, the research assistant system 206 and/or one or more associated components may be part of a standalone application that may be installed and stored on the device(s) 102 and 106.

The research assistant UI component 208 may generate different graphical user interfaces to guide and receive user input. In some instances, the research assistant UI component 208 can correspond to the research assistant UI component 112 of FIG. 1. As described herein with respect to the research assistant UI component 112, the research assistant UI component 208 may generate a user interface to provide guidance and prompts to collaborate with the user(s) 104 to explore a research topic. The process to generate the user interface to provide guidance and prompts will be described herein in more detail with respect to FIGS. 6-20.

In some examples, the research assistant user interface (UI) component 208 may include a prompt for entering an input query and/or search schema to start a search for a research topic. The search schema may define one or more search keywords and/or parameters including, but not limited to, a search context, a source concept, specific concept, a generic concept, a target concept, a relation, a relation link between specified concepts, and a search constraint type. A search context may be any word or phrase that is associated with the research topic, and the "search context" is used by the query component 210 as "bias" when the search engine is conducting a search for some result, wherein the results are search with the "context." As described herein, a concept may be any search term or phrase to explore ideas related to the research topic. A "specific" concept is an explicit search word(s). A "generic" concept is an implicit search word(s) and may include a generic category for search results (e.g., generic concept: "city," specific concept: "Portland"). A relation is a named semantic link between concepts. The answer is evidenced by a chain of relationships between a starting concept and an ending concept, with connective interim concepts that are not part of the question but discovered during research. The research assistant UI component 208 may configure prompts for the users) 104 to iteratively explore evidence to discover relations in the causal path and connect concepts.

The research assistant UI component 208 may generate a user interface to guide user input to enter an input query and explore the evidence chains. As described herein, the research assistant system 206 or associated components may generate a query graph or a data structure to store research data ("findings").

In some examples, the research assistant UI component 208 may generate different views of the query graph. The different views may include different formats of presenting the evidence text to allow a more text-friendly view of the different search results. For instance, the research assistant UI component 208 may focus on text view and hide graphs. The different views may include different visual representations of the research data of the query graph.

The research assistant UI component 208 may generate a visual representation for the query graph. In some examples, the visual representation of the query graph may include a concept map of the research data. The concept map may visually represent "concepts" as nodes and "relationships" as links or edges that connect the concepts. A concept map may start with a first specific concept as the "main concept," and subsequent "discovered concepts" may branch from the main concept, with the branches indicating relation links between concepts. As described herein, the system guides user input to build evidence links. An evidence link is a relation connecting two concepts supported by evidence passages. The research assistant UI component 208 may generate interactable discovered concept nodes that are annotated with the evidence link information. For example, a concept map may indicate a main "concept_A" has a relation link to "concept_B," the node for "concept_B" may be interactable to view the evidence link information between "concept_A" and "concept_B."

In some examples, the research assistant UI component 208 may configure the user interface to guide the user input repeat the research process by iteratively exploring evidentiary chains to connect the dots through a large body of knowledge ("data sources"), including natural language text (e.g., journals, literature, documents, knowledge base, market research documents, and/or structured databases). The knowledge sources may include any print media or electronic sources and any unstructured, semi-structured, and structured knowledge. Non-limiting examples of knowledge sources may include manuscripts, letters, interviews, records, textbooks, magazine articles, book reviews, commentaries, encyclopedias, almanacs, books, brochures, journals, magazines, newspapers, medical ontologies, research articles, clinical reports, case studies, dissertations, peer-reviewed articles, knowledge graphs, research papers, clinical studies, music, video, photos, and the like.

In some examples, the research assistant UI component 208 may receive user input for specifying an input query and send the input query to the query component 210 for processing and searching.

The query component 210 may include a semantic search engine 212 and a structured query engine 214. In some instances, the query component 210 can correspond to the query component 114 of FIG. 1. As described herein with respect to the query component 114, the query component 210 may receive an input query and perform a search based on the input query. The query component 210 may receive an input query and perform a search based on the input query. The input query may be received as structured data format ("structured query"), unstructured data format ("unstructured query" or "natural language question"), and/or may include a search schema and/or a causal schema.

In various examples, the query component 210 and the research assistant UI component 208 may generate a user interface to present a prompt for input query based on different research needs. For instance, the user interface may present different search prompts for the sophistication level of an expected end-user and may be based on the research application. In a first non-limiting example, the research assistant UI component 208 may include a prompt for receiving input query as a natural language question. In a second non-limiting example, the research assistant UI component 208 may include prompts for receiving input query as search parameters, wherein the input query received includes a first concept and a second concept. In a third non-limiting example, the research assistant UI component 208 may include prompts for receiving input query as search parameters, wherein the input query received includes a first concept and a relation. In a fourth non-limiting example, the research assistant UI component 208 may include a prompt for receiving input query as a search schema. In a fifth non-limiting example, the research assistant UI component 208 may include prompts for receiving input query as a causal schema. In a sixth non-limiting example, the research assistant UI component 208 may receive an input query as generated by the system to explore additional concepts or relations.

The query component 210 may generate a query graph to store the search data or any related finding for an iterative exploration of the input query. In some examples, the query graph may include a concept map that starts with a primary concept that branches out to other concepts with the branches indicating relation links between concepts, and the other concepts may be individually explored to form additional branches. As described herein, the research assistant UI component 208 may generate a visual representation for the query graph and may indicate "concepts" as nodes and "relationships" as links or edges that connect the concepts. As described herein, a concept may include any individual search term(s), generic concept, type, entities, propositions, and/or statements.

In various examples, the query component 210 may receive input query including a search schema or a causal schema. The search schema and/or the causal schema may specify search instructions and/or parameters for how the research assistant system 206 should perform the search. In some examples, the search schema or the causal schema may specify instructions for the research assistant system 206 to automatically repeat the research steps and automatically generate evidentiary links between a starting concept and an ending concept.

The query component 210 may receive different search parameters and may perform different search process in response. For instance, the search schema may specify, two "primary concepts," and the system may explore possible "multi-hop" links between the two primary concepts. Alternatively, and/or additional, the search schema may specify a causal schema to search for a causal pathway with a starting point ("source concept") and connected to ending point ("target concept"). The causal pathway may be a multi-hop link with one or more intermediate concepts between the starting and ending points. The present system may explore different possible causal pathways with different intermediate links and/or intermediate concepts starting from a source concept and ending at the target concept. This may be done by guiding user input to iteratively select the intermediate links and/or intermediate concepts or may be automatically generated by the system using an inference engine. After generating a causal pathway, the system may verify that there are complete connecting evidence links starting from the source concept and ending at the target concept.

In additional and/or alternative examples, the search schema may define a primary concept and a relation for exploring, and the query component 210 may explore new concepts that have the relation link to the primary concept. The query component 210 may configure exploration tools, including a concept exploration tool or a relationship exploration tool based on the input query. As described herein, an answer to a complex research question may be inferred by a sequence of connected statements, each occurring in different documents in the corpora where no one statement or one document contains the answer. The query component 210 may use the semantic search engine to search for and construct the sequence of connected statements beginning with the starting concept and terminating at the ending concept. The sequence of connected statements may include a sequence of relationships linking concepts.

In some examples, query component 210 may determine the search engine and/or process based on the data format of the input query. The search engine may include the semantic search engine 212 and the structured query engine 214. In various examples, the input query includes an unstructured query with a natural language question, and the query component 210 may use a semantic parser to convert the natural language question to a structured representation for the input query. The structured representation of the input query may be associated with the query graph. In additional and/or alternative examples, the input query includes a structured query, and the query component 210 may search a structured database or knowledge graph to output query results.

In various examples, the query component 210 may include a semantic search engine 212 to search for concepts in a text corpus. The semantic search engine 212 may search for evidentiary passages from document search engines or embedded searches.

The query component 210 may configure exploration tools, including a concept exploration tool or a relationship exploration tool based on the input query. In some examples, the input query may define two primary concepts, including a starting point/concept and an ending point/concept. The query component 210 may explore relationship links and causal pathways between the two primary concepts. In additional and/or alternative examples, the input query may define a primary concept and a relation for exploring, and the query component 210 may explore new concepts that have the relation link to the primary concept. As described herein, an answer to a complex research question may be inferred by a sequence of connected statements, each occurring in different documents in the corpora where no one statement or one document contains the answer. The query component 210 may use the semantic search engine 212 to search for and construct the sequence of connected statements beginning with the starting concept and terminating at the ending concept. The sequence of connected statements may include a sequence of relationships linking concepts.

The semantic search engine 212 may include a domain theory and associated text corpus for performing a search. A domain theory includes knowledge representation of a domain that indicates a specific subject area, topic, industry, discipline, and/or field in which a current application is intended to apply. In a non-limiting example, a domain may include life science, computer science, engineering, biology, chemistry, medical, business, finance, and the like. The search may include a keyword (e.g., the input concept and/or relations) search in documentations and passages, web search, and embedded search for terms beyond explicit keywords. The query component 114 may output query results including one or more evidentiary passages and/or knowledge graphs, and call the natural language understanding engine to interpret the query results.

The structured query, engine 214 may include a database of knowledge graphs for performing a search. The search may search with a structured query may return false or true with a constructed knowledge graph. The structured query engine 214 may output query results, including the knowledge graph, and call the natural language understanding engine 216 to interpret the query results.

The natural language understanding (NLU) engine 216 may include a semantic parser 218, a semantic fit component 220, and structured query engine 214. In some instances, the NLU engine 216 can correspond to the natural language understanding (NLU) engine 116 of FIG. 1. As described herein with respect to the NLU engine 116, the NLU engine 216 may receive and process the query results. The NLU engine 216 may apply a multi-dimensional interpretation process with a domain-independent interpretation schema to analyze the query results. The multi-dimensional interpretation process may include semantic parsing, semantic fit detection, and polarity detection. In some examples, the NLU engine 216 may use a reasoning engine and/or an inference engine to help interpret the query data.

In various examples, the NLU engine 216 can configure a semantic textualizer to produce an unstructured natural language representation of a structured, logical form. The semantic textualizer may serve as an inverse function of the semantic parser 218. The semantic textualizer may receive structured graphs from a reasoning engine or database of knowledge graphs (e.g., the structured query engine 214) and may produce natural language explanations from the structured data.

The semantic parser 218 may analyze the query results by semantically parsing the evidentiary passages and generating interpreted query results. The semantic parser 218 may parse the evidentiary passages to discover relations connecting concepts and construct a set of semantic indicators that qualify the occurrences of the relations.

In some examples, the semantic parser 218 may use a relational qualification schema (RQS) to describe or qualify a set of conditions under which a relation may be true. As described herein, in machine language, a relation is a named semantic link between concepts, and relations are verb-senses with multiple name roles. Natural human language has words with multiple interred meanings, while machine language looks for a direct match; thus, knowledge representation allows for a machine to read the same word and may correctly interpret the meaning. A relation word may include multiple meanings to a human researcher, but not for a machine; thus, the system replaces the relation link with a semantic link to allow the system to search for "relation" words and may accept semantically similar words. A semantic link is a relational representation that connects two representations (e.g., concepts), supports interpretation and reasoning with other links, and facilitates predictive operations on representations. The semantic parser 218 may generate the interpreted query results by interpreting the query results in a semantic schema, including the constructed set of semantic indicators. The semantic schema may map interpreted concepts to "concept type" and interpreted relations to "semantic type." The RQS may include a set of named semantic indicators that are modifiable and extensible. Some example semantic indicators include:

temporal (semantic indicator for when, or a time at which, the relation may occur);
spatial (where or in what location does it occur);
manner/instrument (what instrument or tool is used to induce the relation to occur);
cause/effect (what concept causes it to occur);
purpose/goal (for what purpose does it occur);
extent (for how long or over what period does it occur); and
modal (with what definiteness does it occur—with certainty or conditional or other factors).

In various examples, the semantic parser 218 may define the semantic indicators including one or more conditions for the occurrence of the relation, the one or more conditions may include a temporal indicator, a spatial indicator, an instrument indicator, a cause indicator, a purpose indicator, an extent indicator, or a modal indicator. In particular the one or more conditions may include a temporal indicator of a time at which the relation is to occur, a spatial indicator of a geographical location or location type (e.g., at a restaurant, at the stadium, etc.) at which the relation is to occur, an instrument indicator of a tool used to induce the relation to occur, a cause indicator of an identity of a concept that causes relation to occur, a purpose indicator of a purpose for the relationship to occur, an extent indicator for a time period for the relationship to occur, and/or a modal indicator of certainty for the relationship to occur.

In various examples, the semantic parser 218 may perform parsing to convert textual representations to structured knowledge. The structured knowledge may use the core theory of a symbolic reasoning engine for processing. For example, suppose a core theory uses a frame-slot structure (e.g., FrameNet, Fillmore, et al., 2001) for representing concepts/relations.

As a non-limiting example, the semantic parser 218 may receive an input query and determine the answer that requires connecting evidence. For example, the question may be, "Is A related to L) (and if so, how)?"

A is related to B (evidence <here. . . >)
B is related to C (evidence <here. . . .> and
C is related to D (evidence <here. . . .>

In the present examples, the semantic parser 218 may parse the query results and construct a relational qualification schema to store the query graph.

| Primary | Relation | Semantic Indicators | Confidence | Evidence |
|---|---|---|---|---|
| A is related to B by R1 | | "when" Temporal, Spatial, Modal, Intent . . . | confidence X | (evidence <here . . . >) |
| B is related to C by R2 | | | confidence Y | (evidence <here . . . >) |
| C is related to D by R3 | | | confidence Z | (evidence <here . . . >) |

In some examples, the semantic parser 218 may convert any results data, including the input query and associated query results with evidence text, as received in text form, to structured results data for other components in the system to use. For instance, the research assistant system 206 may store structured results data with positive feedback from a user as a verified knowledge graph in a knowledge database for future queries.

The semantic fit component 220 performs semantic fit detection to verify the interpreted query results against any explicit or unnamed type constraints set by the input query. The semantic fit component 220 may also check that the semantic type in the input query matches that of the interpreted query results. As described herein, the present system may automatically construct multi-hop relation chains by linking concepts of specified interest. To help guide the system, the input query may specify a search constraint and/or search parameters, and the semantic fit component 220 may verify the search results against the search constraint and/or search parameters. The semantic fit component 220 provides more precise search results by filtering out unwanted information. For instance, an example search schema may specify search parameters including specific concept, "apples" and relation, "is a good ingredient for," and search results constraint by concept type, "savory dish," This example search schema would filter out many of the sweet dessert recipes that a user is trying to avoid.

The polarity component 222 may perform polarity detection to identify refuting evidentiary passages with semantic context. The NUJ engine 216 may output interpreted query results. The interpreted query results may include interpreted relation results and/or interpreted concept results with evidence texts, and the evidence texts may include both supporting and refuting evidentiary passages. By providing both supporting and refuting evidence for the same evidence link that the system is trying to build, the polarity component 222 allows the user to compare the evidence for unbiased search results. For instance, a user may attempt to prove "walking is better than running," but the search results indicate five articles supporting and 50 articles refuting. The user may wish to reconsider his argument or conclusion, such as adding "for people with bad knees."

The knowledge aggregation and synthesis engine 224 may include a clustering and similarity algorithm 226, an originality and saliency component 228, and an authorship component 230. In some instances, the knowledge aggregation and synthesis engine 224 can correspond to the knowledge aggregation and synthesis engine 118 of FIG. 1, As described herein with respect to the knowledge aggregation and synthesis engine 118, the knowledge aggregation and synthesis engine 224 may receive and process the interpreted query results with evidence texts. In some examples, the knowledge aggregation and synthesis engine 224 and components may include functions to cluster and synthesize the interpreted query results to output results data with aggregated clusters and associated aggregate confidence. In various examples, the aggregate confidence may be based on the score of the evidence passages supporting the aggregated clusters.

The clustering and similarity algorithm 226 may aggregate information in the interpreted query results. The clustering and similarity algorithm 226 may determine to grouped text in the interpreted relation results and/or interpreted concept results based on a high degree of similarity. The grouped text for the interpreted relation results forms a relationship cluster. The grouped text for the interpreted concept results forms a concept cluster. The clustering and similarity algorithm 226 may also determine to group text based on "occurrence" in the text. For instance, a relationship occurrence may include a specific relation expression in some text, and multiple relation occurrences that vary in their form may be clustered to receive a higher confidence score over a singular relation instance.

In some examples, the clustering and similarity algorithm 226 may determine to cluster semantic relations and their associated arguments based on the similarity between relations and/or concepts. The grouped text based on the semantic relations and their associated arguments forms a propositional cluster. The similarity may be determined based on using a thesaurus and/or word embeddings. The clustering and similarity algorithm 226 may generate result clusters, including concept clusters, relation clusters, and propositional clusters. Each cluster may be annotated with the related portion of evidence texts, including a link to a summarized evidence passage.

In some examples, the clustering and similarity algorithm 226 may determine a set of relation occurrences and combine the set to a single relational instance to generate a cluster. In some examples, the clustering and similarity algorithm 226 may output aggregate confidence associated with evidence texts that support the cluster. The aggregate confidence may be based on the relevance score of the evidence texts. The aggregated query results may include clusters with annotated evidence texts.

The originality and saliency component 228 may determine to perform analysis on the aggregated query results with processes including originality detection and saliency computation. The originality detection may determine a count for knowledge source, wherein a lower count value is associated with higher originality. The originality detection may determine that a piece of evidence has been duplicated and/or sourced from the same place as another evidence text. The saliency computation determines a prominence in corpus and may be based at least in part on as frequency of the source. The saliency computation may determine confidence in count and relevance and/or could be defined by the user.

The authorship component 230 may search the evidence source and identify the author to determine the credibility of the author. In some examples, the authorship component 230 may maintain a one or more databases of credible sources and authors based on the domain knowledge. A credible source is one that is written by someone who is an expert in their discipline and is free of errors and bias. However, different domain knowledge may include different tolerance for "credible source" as well as different experts, thus the authorship component 230 may use and/or maintain different databases of credible source. In some examples, the authorship component 230 may include options for a user to add credible source and/or may allow a user to set "credibility weight" for specific source (i.e., a named author or a named journal) or for general category of source (i.e., any peer reviewed articles)

The knowledge aggregation and synthesis engine 224 may output aggregated query results with scored evidence passages.

The scoring and ranking component 232 may receive and rank the aggregated query results. The aggregated query results may include one of a concept cluster, a relation cluster, or a propositional cluster. In some instances, the scoring and ranking component 232 can correspond to the scoring and ranking component 120 of FIG. 1. As described herein with respect to the scoring and ranking component 120, the scoring and ranking component 232 may apply one or more ranking algorithm to rank the clusters by various features. For example, the ranking algorithm may include a top K elements pattern that returns a given number of the most frequent/largest/smallest elements in a given set. The scoring and ranking component 232 may output the ranked aggregate results with the evidence texts.

The evidence summary component 234 may process the ranked aggregate results with the evidence texts. In some instances, the evidence summary component 234 can correspond to the scoring and ranking component 120 of FIG. 1. As described herein with respect to the scoring and ranking component 120, the evidence summary component 234 may process the ranked aggregate results with the evidence texts to generate results data, including one or more result clusters annotated with the related portion of evidence texts. In some examples, the present system may use the semantic parser 218 to translate natural language evidence texts into corresponding semantic interpretations of the texts. The semantic interpretations of the texts are machine-readable knowledge representations that may be stored in a knowledge base. The evidence summary component 234 may continuously generate and store semantic interpretations of the search texts into a structured knowledge base to increase the speed for future queries. In various examples, the evidence summary component 234 may annotate the portion of the one or more evidence passages with corresponding semantic interpretations of the portion of the one or more evidence passages.

The evidence summary component 234 may generate evidence summaries for the ranked aggregate results. The evidence summary component 234 may determine the portion of the evidence passages that are related to the ranked aggregate results and may call the NLU engine 216 to use a semantic textualizer to reverse-translate the semantic interpretations into natural language. The evidence summary component 234 may annotate the clusters with the summarized evidence text.

The one or more result clusters include at least one concept cluster, a relation cluster, and a propositional cluster. Each cluster of the one or more result clusters annotated with the related portion of evidence texts includes a link to a summarized evidence passage. The results data may be presented, via the user interface, to verify whether at least one cluster is correct or incorrect. The input query and results data are marked as true positives or false positives and saved, by the research assistant system 206, as training data for training the different components of the system.

In some examples, the evidence summary component 234 may receive a request to process the research results with the evidence texts and generate a document with the research results report and summarized text. The evidence summary component 234 may provide citations and links to the evidence texts.

The hypothesis component 236 may process the research data and infer new information. In some examples, the hypothesis component 236 may add new information to the existing query graph. In additional and/or alternate examples, the hypothesis component 236 may generate a new query based on the new information or generate a new search schema to initiate a new search.

The symbolic reasoning engine 238 may receive an input query with context and may determine the answer to the query. The context may include a set of facts (e.g., statements extracted from evidence texts by the semantic parser 218) against which to evaluate the query. As described herein, the symbolic reasoning engine 238 may include a formal logic-based reasoner that operates on structured queries and rules. The symbolic reasoning engine 238 may determine the answer to the query by identifying explanations (also referred to as "proofs"). The symbolic reasoning engine 238 may return the explanations and/or logically valid answers, A logically valid answer may include a proof dependency graph that explains the answer with context. The symbolic reasoning engine 238 may generate the proof dependency graph while iteratively interacting with the query component 210 determines the relevant rules (e.g., search schema) for the proof dependency, graph.

In some examples, the symbolic reasoning engine 238 may determine a reasoning algorithm to use for answering queries. The reasoning algorithm may include at least one of a backward chaining, forward chaining, Selective Linear Definite clause resolution ("SLD resolution"); and first-order logic ("FOL") algorithm. For instance, the symbolic reasoning engine 238 may be based on SLD resolution via backward chaining.

In a non-limiting example implementation, the symbolic reasoning engine 238 may use a backward chaining algorithm. The backward chaining algorithm may start by retrieving rules leading to an original query. The backward chainer may include a rule retriever and may call a dynamic rule generator. The dynamic rule generator may use a statistical model trained on structured rule applications in different contexts. The statistical model may generate new rules each leading to the original query, and may associate each rule with a certain precision/confidence. The symbolic reasoning engine 238 may determine which rules to backchain on next based on one or more heuristics, including, but not limited to, aggregate confidence of the current proof path, a relevance of next rule given context/current proof path, a likelihood for success given prior successful explanations, and the like.

In various examples, the symbolic reasoning engine 238 may explore multiple rule paths in parallel. For instance, the antecedents of the back-chained rules now become new sub-goals (secondary goals) that the reasoner needs to prove, and so it calls the query component 210 again with these new sub-goals in the next iteration. This process may continue until the symbolic reasoning engine 238 may match rule conditions with facts in the context (in which case, it has found a valid proof), or if the symbolic reasoning engine 238 fails to find complete proofs within practical resource limits (e.g., no more rules found above a predetermined confidence threshold). A complete proof/explanation is a set of inference rules and facts that logically entail the query.

In various examples, the symbolic reasoning engine 238 may use any portion of the static rules, inference rules, and/or general rule templates stored in the data store 244 as input to train one or more reasoning model(s).

Figure 4:
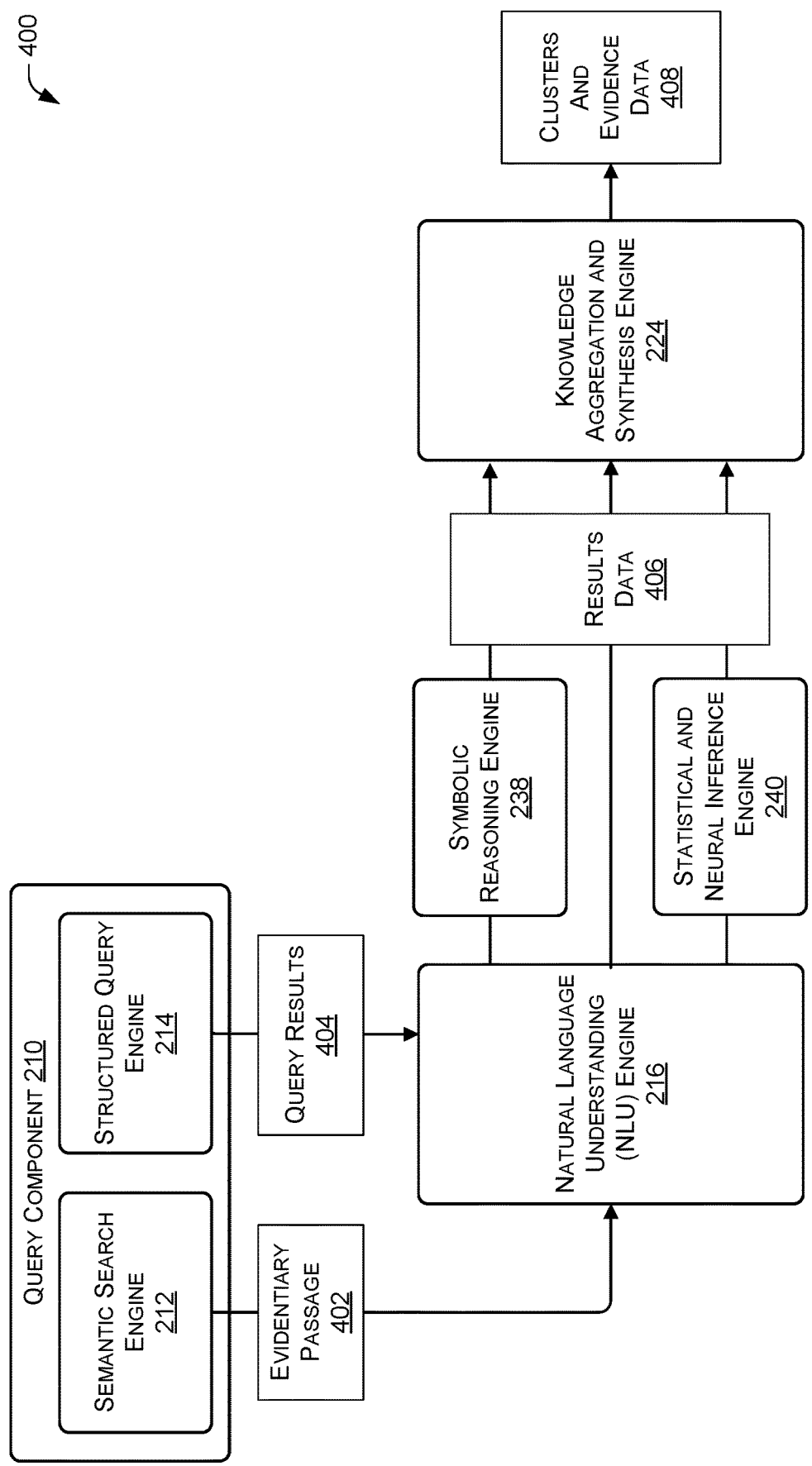
FIG. 4 is a block diagram of an example implementation of a research assistant tool configured with a symbolic reasoning engine and/or a statistical neural inference engine to infer relations from gathered data.

In some instances, the symbolic reasoning engine 238 can correspond to the symbolic reasoning engine 238 of FIG. 4.

The structured query engine 214 may maintain a static rule knowledge base; including a knowledge base of a fixed collection of rules. In various examples, the rules from the collection of rules may individually be associated with confidences.

In some examples, the structured query engine 214 may query the static rule knowledge base with a query graph with the context and may receive a list of rules based on the reasoning algorithm implemented. For instance, the symbolic reasoning engine 238 may implement a backward direction algorithm, the static rule knowledge base may return a list of rules whose consequent unifies (matches) the goal, and the rules have "relevance-similarity," which is determined using a similarity function, to the context greater than predetermined threshold confidence. In an alternative and/or additional example, the symbolic reasoning engine 238 may implement a forward direction algorithm, the static rule knowledge base may return a list of rules with antecedents that unifies with the goal, wherein the goal may be a conjunction of logical formulae.

The dynamic rule generator may receive a target proposition (e.g., input goal) and may output a scored list of hypothesized rules that could be used to prove the target proposition. In some examples, the dynamic rule generator may receive a knowledge base (KB) as input and may determine one or more general rule templates to use. The dynamic rule generator may use the input KB to help connect the dots when the knowledge required for inference is missing from a static KB (e.g., cannot be found by the static rule knowledge base). The general rule templates may include rules with variables to be replaced with constants.

In various examples, the dynamic rule generator may implement a latent generative model that does not explicitly encode all the rules and may use a statistical model approach to implicitly capture the rule knowledge and generate explicit rules on demand. The dynamic rule generator may use a statistical model trained on structured rule applications in different contexts. The statistical model may generate new rules each leading to the target proposition (e.g., input goal), and associate each rule with a certain precision/confidence. The dynamic rule generator can generate unstructured or structured probabilistic rules given a specific context.

In some examples, the dynamic rule generator and other components of the research assistant system 206 may improve from feedback received from the user(s) 104. For instance, as described herein with respect to FIG 1, when the example research assistant interface 124 is presented to the user(s) 104 in the user interface, the research assistant system 206 may receive feedback on which inference rules in context are correct or incorrect. As described here, this feedback is useful to the static rule knowledge base (e.g., to increase its coverage), the dynamic rule generator (e.g., as new training data to improve the statistical model), and the symbolic reasoning engine 238 (e.g., the knowledge in a reinforcement learning strategy that guides the proof exploration process).

The statistical and neural inference engine 240 may include a knowledge base of inference rules for the associated domain. In some examples, the rules may include a textual (unstructured) form or structured form. The rule applications can be positive (correct rule application in this context) or negative (incorrect rule application in the context).

In some examples, the statistical and neural inference engine 240 may include rules that are fully bound and/or partially bound. The fully bound rules include rule templates with variables that are replaced with constants. The partially bound rules include rule templates containing variables only. The rules can be crowdsourced via a standalone knowledge acquisition task, extracted from large corpora, or acquired via query results from the user(s) 104 using the research assistant system 206, as described herein.

In various examples, the statistical and neural inference engine 240 may build a chain of evidence by connecting the evidence links. As described herein, the present system may construct individual evidence links and/or guide user input to build chains of evidence by connecting the evidence links. For instance, the research assistant system 206 may guide a user to discover a single evidence link by searching for related terms such as, "What does A relate to?" Or "Is A related to B?" In response, the system may determine that "A relates to B" based on three articles found that supports this answer. The user may select that answer, and confirm the articles support the answer, and the system may store "A relates to B" as an evidence link including links to the articles. The evidence link may be stored in a structured database for queries that may require connecting evidence links. The system may present prompts to guide user interaction to expand an evidence chain to the next concept of interest. For instance, the next suggest query may be, "What does B relate to?" To discover that, "B relates to C." The new evidence link, "B relates to C," may also be stored in the structured database. The statistical and neural inference engine 240 may use the evidence links stored in the structured database to construct a chain of evidence. For instance, an input query may ask, "Is A related to D?" The statistical and neural inference engine 240 and the query component 210 may find articles with "A relates to B" and "C relates to D" and may leverage evidence links stored in the structured database and apply the inference engine to create an evidence chain of "A relates to B," "B relates to C," and "C relates to D.

In various examples, the system may train one or more ML model(s) 242 using labeled data as training data. Machine learning generally involves processing a set of examples (called "training data") to train one or more ML model(s) 242. The model(s) 242, once trained, is a learned mechanism that can receive new data as input and estimate or predict a result as output. Additionally, model(s) 242 may output a confidence score associated with the predicted result. The confidence score may be determined using probabilistic classification and/or weighted classification. For example, a trained ML model(s) 242 can comprise a classifier that is tasked with classifying unknown input as one of the multiple class labels. In additional examples, the model (s) 242 can be retrained with additional and/or new training data labeled with one or more new types (e.g., rules) to teach the model(s) 242 to classify unknown input by types that may now include the one or more new types.

In additional and/or alternative examples, the ML model(s) 242 may include a generative model, which is a statistical model that can generate new data instances. Generative modeling generally involves performing statistical modeling on a set of data instances X and a set of labels Y in order to determine the joint probability p(X, Y) or the joint probability distribution on X×Y. In various examples, the statistical model may use neural network models to learn an algorithm to approximate the model distribution. In some examples, the generative model may be trained to receive input conditions as context and may output a full or partial rule. In an additional example, the generative model may include a confidence calibrator that may output the confidence associated with the rule generated by the generative model. As described herein, the dynamic rule generator may use a generative model that generates unstructured probabilistic rules and/or structured probabilistic rules based on the input context.

In the context of the present disclosure, the input may include data that is to be handled according to its context, and the trained ML model(s) 242 may be tasked with receiving an input goal and outputting a rule that connects the input goal with the context. For instance, as described herein, the system may use a generative model that receives an input goal, "Person motivated to buy X," and an input context which includes facts such as, "Person likes X," and the generative model can connect the context to the goal via a rule such as "Person likes X motivates Person to buy X" and return the generated rule.

In some examples, the trained ML model(s) 242 may classify an input query with context as relevant to one of the inference rules and determine an associated confidence score. In various examples, if the trained ML model(s) 242 has low confidence (e.g., a confidence score is at or below a low threshold) in its proof for an explanation to an input query, this low confidence may return no rules found. An extremely high confidence score (e.g., a confidence score is at or exceeds a high threshold) may indicate the rule is proof for an input query. After the inference rule has been applied to an explanation, the data with the inference rules may be labeled as correct or incorrect by a user, and the data may be used as additional training data to retrain the model(s) 242. Thus, the system may retrain the ML model(s) 242 with the additional training data to generate the new ML model(s) 242. The new ML model(s) 242 may be applied to new inference rules as a continuous retraining cycle to improve the rules generator.

The ML model(s) 242 may represent a single model or an ensemble of base-level ML models and may be implemented as any type of model(s) 242. For example, suitable ML model(s) 242 for use with the techniques and systems described herein include, without limitation, tree-based models, k-Nearest Neighbors (kNN), support vector machines (SVMs), kernel methods, neural networks, random forests, splines (e.g., multivariate adaptive regression splines), hidden Markov model (HMMs), Kalman filters (or enhanced Kalman filters), Bayesian networks (or Bayesian belief networks), expectation-maximization, genetic algorithms, linear regression algorithms, nonlinear regression algorithms, logistic regression-based classification models, linear discriminant analysis (LDA), generative models, discriminative models, or an ensemble thereof. An "ensemble" can comprise a collection of the model(s) 242 whose outputs are combined, such as by using weighted averaging or voting. The individual ML models of an ensemble can differ in their expertise, and the ensemble can operate as a committee of individual ML models that are collectively "smarter" than any individual machine learning model of the ensemble.

The data store 244 may store at least some data including, but not limited to, data collected from the research assistant system 206, the symbolic reasoning engine 238, the statistical and neural inference engine 240, and the model(s) 242, including data associated with rules data, knowledge base data, core theory data, natural language data, general rule templates data and training data. In some examples, the data may be automatically added via a computing device (e.g., the computing device(s) 102, the device(s) 106). The rules data may include static rules data and generated inference rules data and may correspond to one or more contexts. In various examples, the static rules data may include a fixed collection of rules, and the individual rules may be associated with a confidence level. As described herein, the symbolic reasoning engine 238 may operate over a specific core theory of logical forms (e.g., logical predicates, functions, formulae) which can be interpreted by the reasoner, and the core theory data may include vocabulary data and any data to produce rules that conform to the core-theory. For instance, if the core theory uses a frame-slot structure (e.g., FrameNet) for representing concepts/relations, then the core theory data may include frame structure data, concept and relationship data, ontology data, and the like. Training data may include any portion of the data in the data store 244 that is selected to be used to train one or more ML models. In additional and/or alternative examples, at least some of the data may be stored in a storage system or other data repository.

Figure 3:
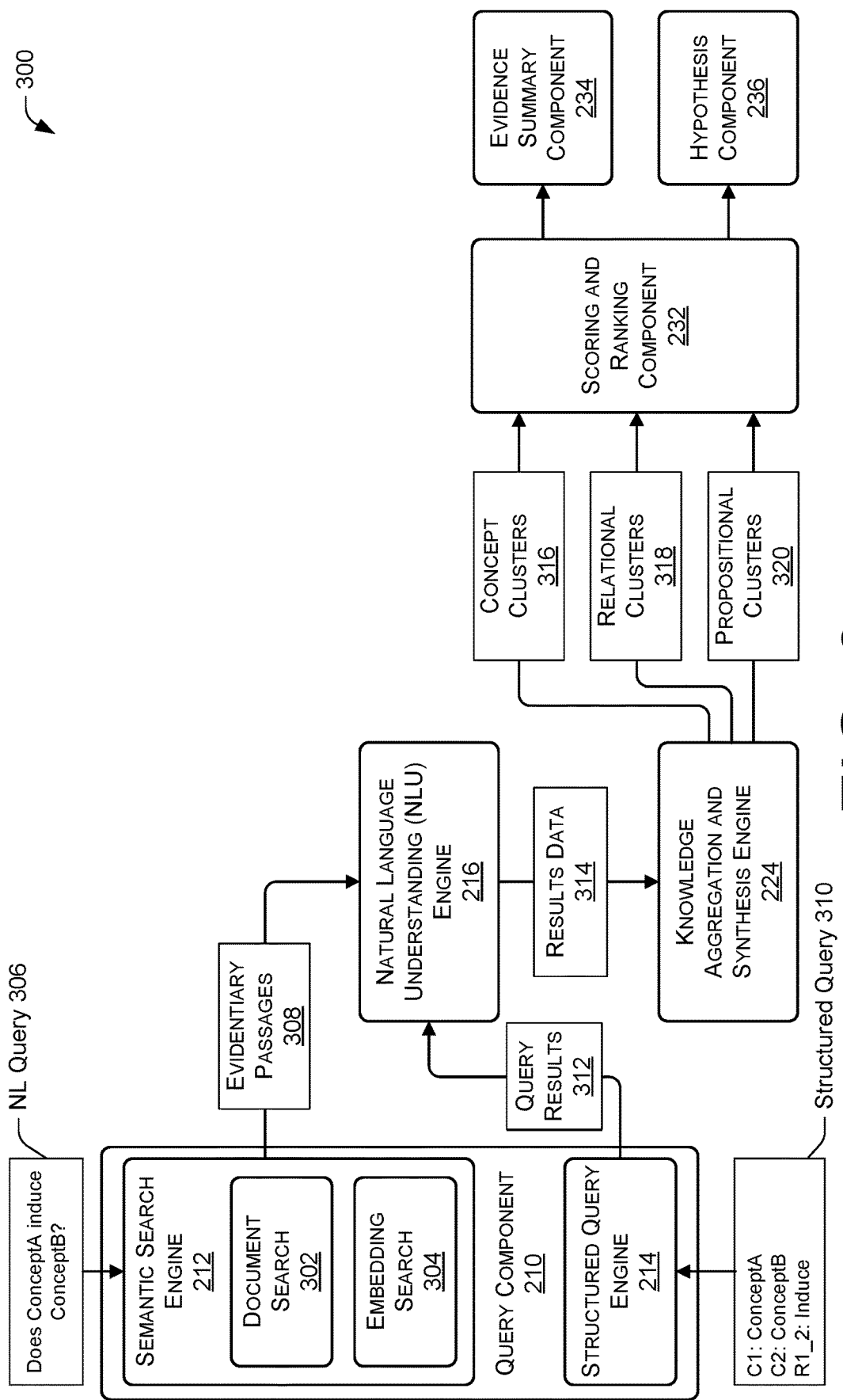
FIG. 3 is a block diagram of an example implementation of select research components, including a semantic search engine and a structured query engine that may be used to perform document search based on the input query.

FIG. 3 illustrates an example implementation 300 of select components, including a semantic search engine 212 and a structured query engine 214 that may be configured to perform a search based on a data structure of input query. The select components may include the semantic search engine 212, the structured query engine 214, a natural language understanding (NLU) engine 216, a knowledge aggregation and synthesis engine 224, a scoring and ranking component 232, an evidence summary component 234, and a hypothesis component 236. The semantic search engine 212 may include document search 302 and embedding search 304.

As described herein, the format that an input query is entered may influence the database(s) searched. The query component may receive an example input query (e.g., example NL query 306 or example structured query 310) and determine the search engine to perform the search based on the data structure of the input query.

In a non-limiting first example, the input query may be example NL query 306 and is entered as "Does ConceptA induce ConceptB?" The query engine may receive the example NL query 306 and determine to use the semantic search engine 212 to process the input query and search for the concepts over a text corpus by performing the document search 302 and the embedding search 304. The semantic search engine 212 may output query data with evidentiary passages 308.

In an additional example, the system may receive the example structured query 310 and determine to use the structured query engine 214 to process the input query and query a structured database for a query graph. The structured query engine 214 may receive a knowledge graph and output a query results 312 with a knowledge graph.

The NLU engine 216 may receive the query data with evidentiary passages 308 and/or the query results 312 and may generate example results data 314. The knowledge aggregation and synthesis engine 224 may aggregate the information in the example results data 314 and output clustered results including at least one of example concept clusters 316, example relational clusters 318, or example propositional clusters 320.

In some examples, the scoring and ranking component 232 may receive the clustered results and determine a ranking for the clustered results. The evidence summary component 234 may present the ranked clustered results data. The hypothesis component 236 may determine an additional query to explore based on the results data.

FIG. 4 illustrates an example implementation 400 of a research assistant tool configured with a symbolic reasoning engine 238 and/or a statistical neural inference engine 240 to process query data. The research assistant tool may include select components, including a semantic search engine 212, a structured query engine 214, a natural language understanding (NLU) engine 216, the symbolic reasoning engine 238, the statistical neural inference engine 240, and a knowledge aggregation and synthesis engine 224.

As a non-limiting example, the present research assistant system may receive example input queries. The semantic search engine 212 may perform a search for an input query and output example evidentiary passages 402. The structured query engine 214 may perform a search for an input query and output example query results 404.

In some examples, the NLU engine 216 may receive the search results data, perform semantic parsing on the evidence text, and interpret the results to generate example query results 404.

In additional and/or alternative examples, the NLU engine 216 may use the symbolic reasoning engine 238 and/or the statistical neural inference engine 240 to further help refine the semantic parse and identify relation links to generate example query results 404. The symbolic reasoning engine 238 may receive the query data with context and may determine the answer to the query. The context may include a set of facts (e.g., statements extracted from evidence texts by the NLU engine 216) against which to evaluate the query. As described herein, the symbolic reasoning engine 238 may include a formal logic-based reasoner that operates on structured queries and rules. The symbolic reasoning engine 238 may determine the answer to the query by identifying explanations (also referred to as "proofs"). The symbolic reasoning engine 238 may return the explanations and/or logically valid answers. A logically valid answer may include a proof dependency graph that explains the answer with context. The symbolic reasoning engine 238 may output the example results data 406 with a full or partial causal chain exploration. The statistical neural inference engine 240 may infer additional relations for the example results data 406.

The knowledge aggregation and synthesis engine 224 may process the example results data 406 to output example clusters and evidence data 408.

Figure 5:
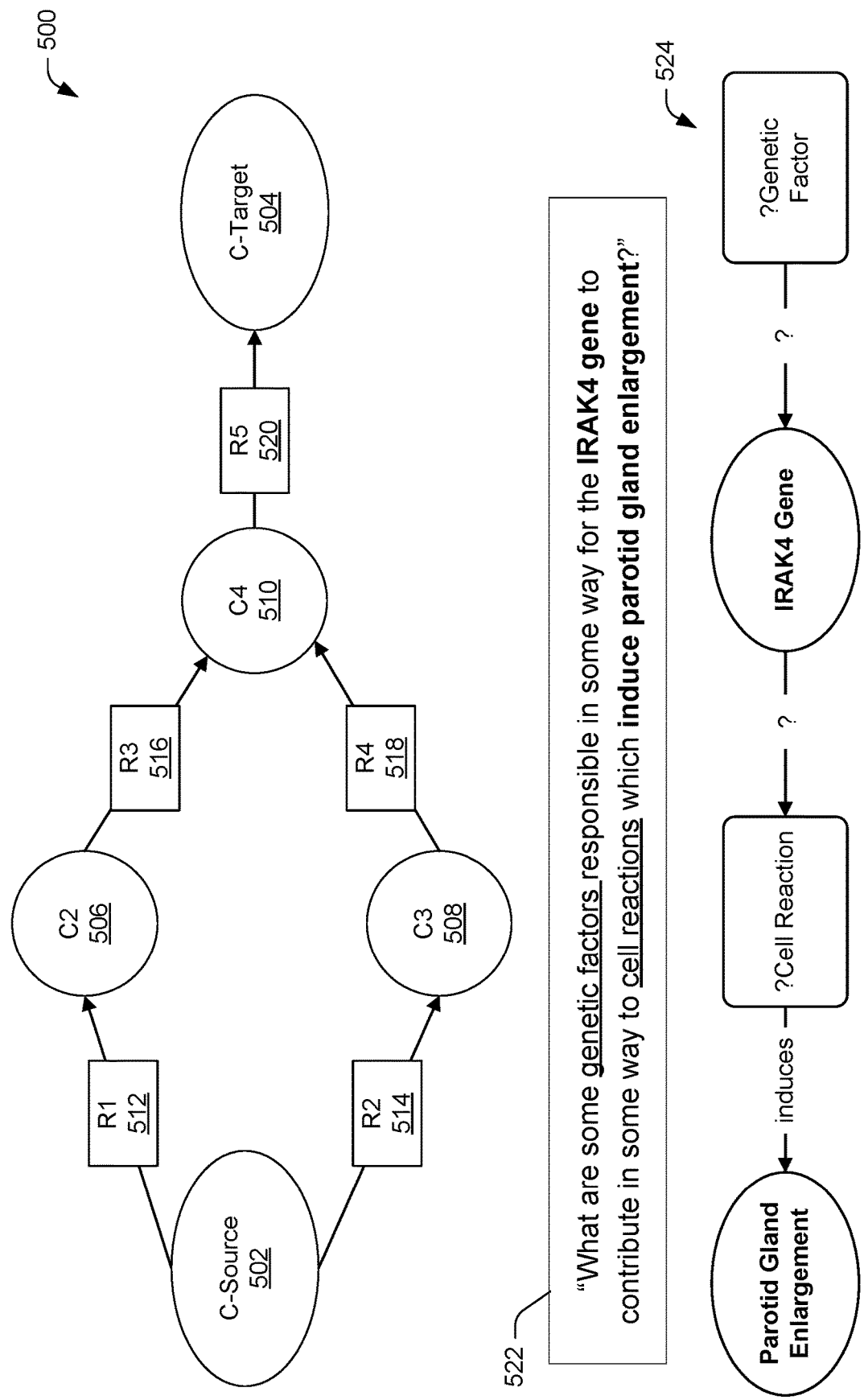
FIG. 5 illustrates an example flow of causal chain schema using the research assistant system, as discussed herein.

FIG. 5 illustrates an example flow 500 for a multilink causal schema using the research assistant system, as discussed herein. The illustrations, for an example causal schema may include example concepts 502, 504, 506, 508, and 510 as example nodes and example relations 512, 514, 516, 518, and 520 as examples links; and an example natural language question 522 and an example causal schema 524 representing the example natural language question 522.

As a non-limiting example, the present system may receive an input query that specifies a causal schema for search. The query component 210 may receive user input for the causal schema that specifies the example source concept 502 and example target concept 504. In the present examples, the intermediate concepts and/or relations are left unspecified.

As described herein, the query component 210 may receive different search parameters and may perform different search processes in response. The input query and/or the search schema may specify a causal schema to search for a causal pathway with a starting point ("source concept") and connected to the ending point ("target concept"). The causal pathway may be a multi-hop link with one or more intermediate concepts between the starting and ending points. The present system may explore different possible causal pathways with different intermediate links and/or intermediate concepts starting from a source concept and ending at the target concept. The present system may guide user input to iteratively select the intermediate links and/or intermediate concepts or may automatically generate by the system using an inference engine.

In some examples, the research assistant system 206 may generate a user interface to present an interactive query graph and to guide user input to perform single-link relation discovery. The interactive query graph may guide user input to select the top-K results for each link and construct the path via an iterative automated research process. In the present example, as depicted, a causal schema may specify 3 hops; thus the system may generate an incomplete causal pathway with interactable nodes to explore the concepts and relationships starting from example source concept 502.

In additional and/or alternate examples, the research assistant system 206 may generate a user interface to present search parameters for the causal schema, including specifying beam-size with confidence thresholds for limiting search space. The system may perform automatic causal pathway construction using any pathfinding algorithms. (e.g., beam search from source to target, bi-directional beam search, or join-order optimized search). The system may return two possible causal pathways for selection. A first possible causal pathway may include example concepts 502, 506, 510, and 504 linked by example relations 512, 516, and 520. A second possible causal pathway may include example concepts 502, 508, 510, and 504 linked by example relations 514, 518, and 520.

In a non-limiting example, the research assistant system 206 may determine to generate a causal pathway schema in response to receiving the example natural language question 522, "What are some genetic factors responsible in some way for the IRAK4 gene to contribute in some way to cell reactions which induce parotid gland enlargement?"

The research assistant system 206 may represent the example natural language question 522 as the example causal schema 524. The example causal schema 524 indicates that the two endpoints of the path are specified, and the intermediate nodes and/or intermediate edges can be either unspecified (?), specified using a type variable ('cell relation), or specified directly (IRAK4, induces).

As indicated:

The circular nodes are specific instances: "Parotid Gland Enlargement" and "IRAK4 gene."

The rectangular nodes are some concept-typed variables: "?Cell Reaction"=something that is a type of cell reaction; "?Genetic Factor"=something that is a kind of genetic factor.

The edges are relations, as depicted, in one edge, the relation is specified with "induces." In the other two cases, the relation is unspecified ("?").

Details of the research assistant system 206 providing user interface elements to explore causal schema with a visual representation of the result causal pathway will be described herein in more detail with respect to FIG. 8.

After generating a causal pathway, the system may verify that there are complete connecting evidence links starting from the source concept and ending at the target concept.

Figure 6:
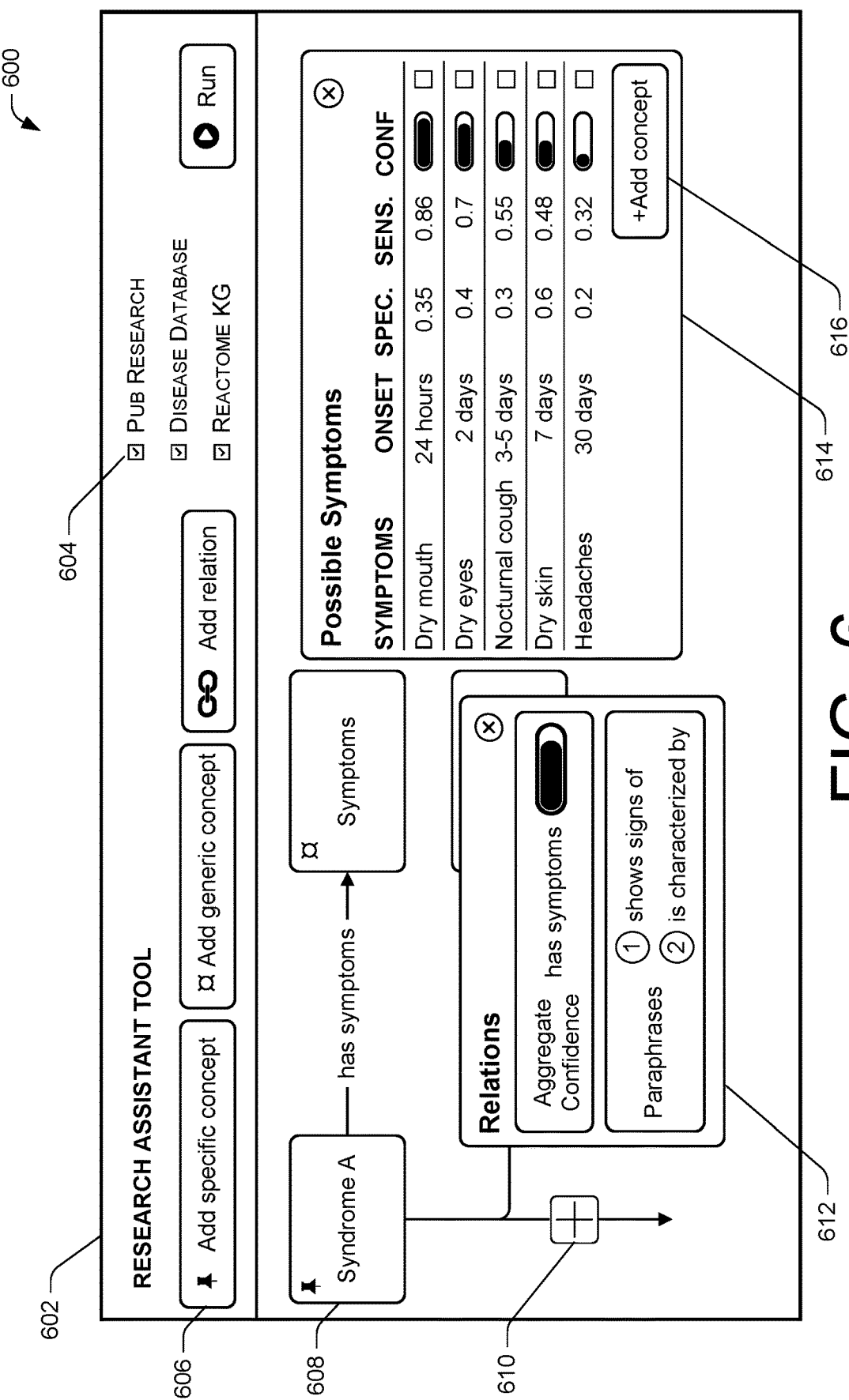
FIG. 6 illustrates an example user interface for initiating research using the research assistant system, as discussed herein.

FIG. 6 illustrates an example user interface 600 for initiating research using the research assistant system, as discussed herein. In some instances, the example user interface 600 may present an example user interface (UI) 602, including example user interface elements 604, 606, 608, 610, 612, 614, and 616.

The research assistant UI component 208 may generate the example UT 602 to guide user input to enter the query and explore the evidence chains, as described herein. The research assistant UI component 208 may generate the example UI 602 to initiate research by guiding user input to enter the query and explore the evidence chains by providing an interactive selection element. The example UI 602 presents the example user interface element 604 allows user input to select the knowledge source to perform research in. For instance, as depicted, "Pub Research," "Disease Database," and "Reactome KG" are all currently selected, thus the system will search through all three knowledge sources when conducting the search.

The example user interface element 606 allows user input to "Add specific concept" for the research. As depicted, the example user interface 602 is already exploring the "Syndrome A." The example user interface element 608 is highlighting the specific concept. The example user interface element 610 allows user input to explore additional relation links.

As described herein, the present system allows a user to explore a research topic (e.g., Syndrome A) by concepts or relations.

In a first non-limiting example, the example user interface element 612 presents information for an example relation cluster for "has symptoms." The example user interface element 612 indicates synonyms for "has symptoms" and an example aggregate confidence. As depicted, the system has high confidence in the aggregating expressions of "Syndrome A has symptoms."

In a second non-limiting example, the example user interface element 614 presents information for the example concept clusters for "has symptoms." The research assistant 7I component 208 may generate the example user interface (UI) 602 to prompt user input for input query to begin the research process. As depicted, the input query may initially define a specific concept of "Syndrome A" and relation of "has symptom."

The query component 210 receives the input query and may conduct a search for the explicit search term "Syndrome A" and search for any articles expressing "Syndrome A" showing symptoms. In the present examples, the query component 210 may find 100 articles about the different symptoms of "Syndrome A." These 100 articles are the "evidentiary passages" of the different symptoms. The evidentiary passages are the "query results," and the query component 210 may output the query results to a natural language understanding (NUJ) engine 216 for processing.

The NLU engine 216 may receive the query results and process the information received as natural language into machine understandable language. The NW engine 216 may output the interpreted query results for the knowledge aggregation and synthesis engine 224. The knowledge aggregation and synthesis engine 224 may receive the interpreted query results and aggregate the interpreted evidence. As described herein, the knowledge aggregation and synthesis engine 224 may rank the knowledge based on aggregating the information and may score the evidence-based on features metrics. The natural language understanding (NLU) engine 216 and the knowledge aggregation and synthesis engine 224 may determine scores for features, including but not limited to aggregation confidence, saliency, relevance, originality, author credibility, and the like. In the present non-limiting example, the knowledge aggregation and synthesis engine 224 may receive the interpreted query results for the 100 articles and apply a clustering and similarity algorithm to cluster the information. As depicted in the example user interface element 614, the 100 articles may only express five different symptoms of "Syndrome A," and the clustering and similarity algorithm may group the similar concepts, which are the five similar symptoms, together to generate "concept clusters" and thus, forming five symptom clusters. Each cluster would include links to their respective articles. The concept clusters are the search results from searching for "Syndrome A," with the relation "has symptom."

In some examples, the knowledge aggregation and synthesis engine 224 may rank the concept clusters and present them in ranked order. Assuming the 100 articles describe five different symptoms, they may have "dry mouth," "dry eyes," "nocturnal cough," "dry skin," and "headaches." In various examples, the knowledge aggregation and synthesis engine 224 may determine there are additional symptoms but determine to not present them based on the confidence being less than threshold confidence or may determine to present a predetermined maximum number of cluster options. The knowledge aggregation and synthesis engine 224 may configure additional models to score the relevance of evidence for each cluster based on a number of features. The knowledge aggregation and synthesis engine 224 may output aggregated query results ("results clusters") to the scoring and ranking component 232.

The scoring and ranking component 232 may receive the aggregated query results and determine an overall ranking for the results clusters. As described herein, each cluster may be scored based on a member count, aggregation confidence, and evidence features, the scoring and ranking component 232 may apply a weight to the different scores and generate a ranking for the "Symptoms" clusters and output ranked query results with the scores.

The example user interface element 614 present a concept cluster that allows user input to explore evidence for concepts. The example user interface element 616 allows user input to add additional concepts for further exploration.

Figure 7:
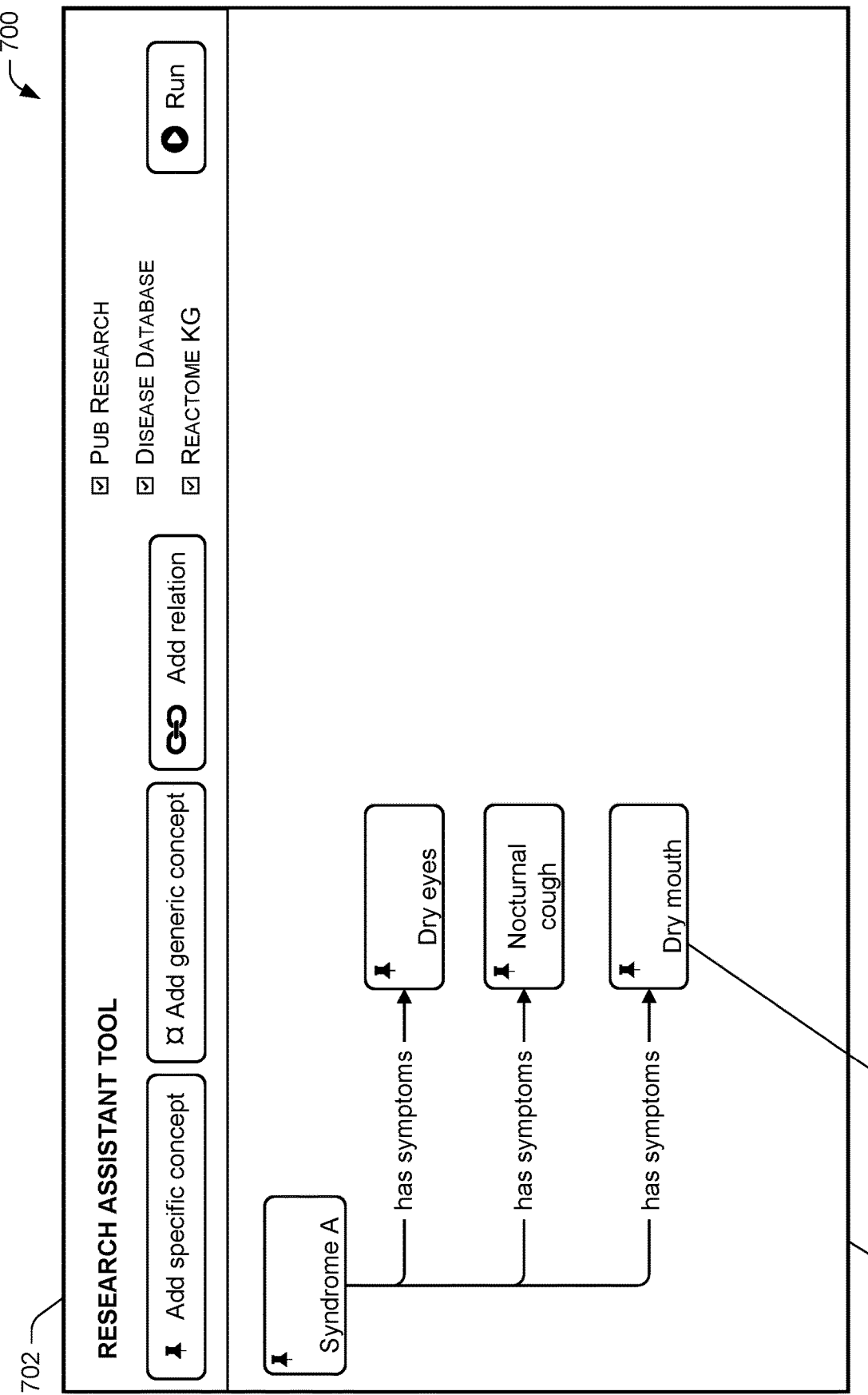
FIG. 7 illustrates an example user interface for performing research using the research assistant system, as discussed herein.

FIG. 7 illustrates an example user interface 700 for performing research using the research assistant system, as discussed herein. In some instances, the example user interface 700 may present example user interface 702, including example user interface elements 704 and 706.

The research assistant UI component 208 may generate a user interface to guide user input to enter the query and explore the evidence chains, as described herein. The research assistant UI component 208 may generate the example user interface 702 to guide research. The example user interface 702 presents the example user interface element 704, which includes an exploration window to allow user input to explore relations or concepts relative to the specific concept "Syndrome A."

As depicted, the example user interface 702 is already exploring relation links of "has symptoms" relative to "Syndrome A" as and the example user interface element 706 is highlighting one of the three example linked concepts. As depicted, based on user input, "Syndrome A" has the relation link "has symptoms" relative to the concepts: "Dry eyes," "Nocturnal cough," and "thy mouth." The user has selected those three concepts for further exploration.

Figure 8:
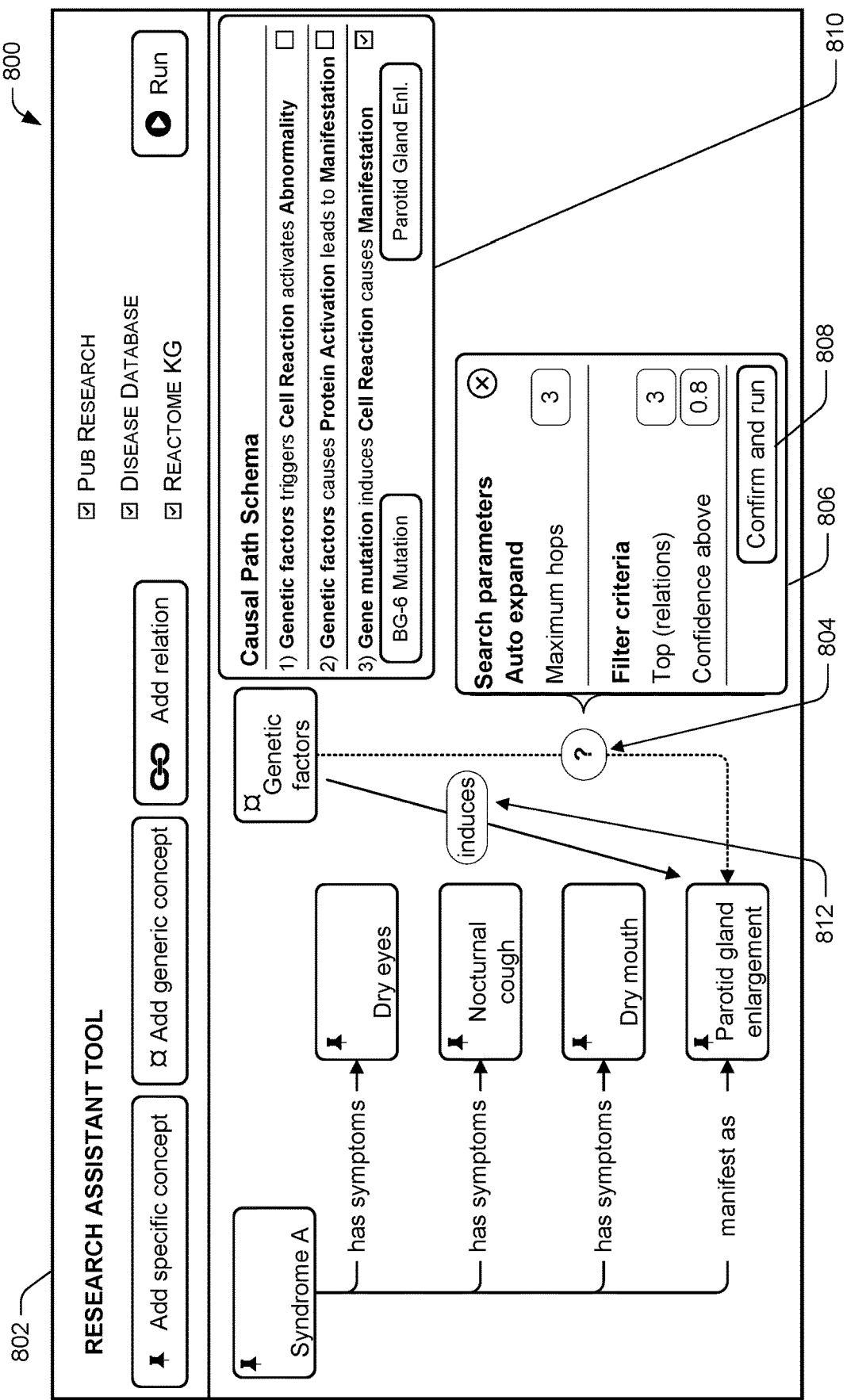
FIG. 8 illustrates an example user interface for performing research with multilink using the research assistant system, as discussed herein.

FIG. 8 illustrates an example user interface 800 for performing research with multilink using the research assistant system, as discussed herein. In some instances, the example user interface 800 may present example user interface 802, including example user interface elements 804, 806, 808, 810, and 812.

The research assistant UI component 208 may generate the example user interface 802 to continue guiding user input to enter the query following the examples illustrated in FIG. 7. As depicted, following the example in FIG. 7, the user has added an additional relation "manifest as" and an additional concept "parotid gland enlargement."

The example user interface element 804 may include prompts to perform research with multilink using the research assistant system 206. The research assistant UI component 208 may generate a user interface element 806 to prompt enter parameters for conducting research by a causal schema. As described herein, the research assistant system 206 may automatically construct multi-hop relation chains linking concepts of specified interest based on a collection of research parameters specified by user input.

In response to receiving user input on the example user interface element 806, the research assistant system 206 may perform automatic causal pathway construction using the specified parameters. As described herein, an input query may include a search schema that specifies a causal schema. The causal schema may trigger automatic repeat searches for a causal pathway from a starting point ("source concept") and connected to an ending point ("target concept"). The system may explore different pathfinding options starting from the source concept, with connecting links ("intermediate links") that connectively lead to the target concept. A causal pathway may include a multi-hop link ("multilink") with one or trim intermediate concepts between the starting and ending points. The system may need to verify that there is a complete connecting link starting from a source concept and ending at the target concept. The search schema may include parameters for how many hops the search engine should automatically search for. For instance, as depicted, the system may attempt to perform a pathfinding algorithm with up to "3" maximum hops.

In some examples, the research assistant UI component 208 may generate the example user interface elements 810 to show the results of performing a causal path schema search using the parameters. As depicted, the example user interface elements 810 presents three causal path options found, and the third option is selected for exploration. The example user interface element 810 presents the example user interface element 812, which indicates the relation link "induces" between two concepts.

Figure 9:
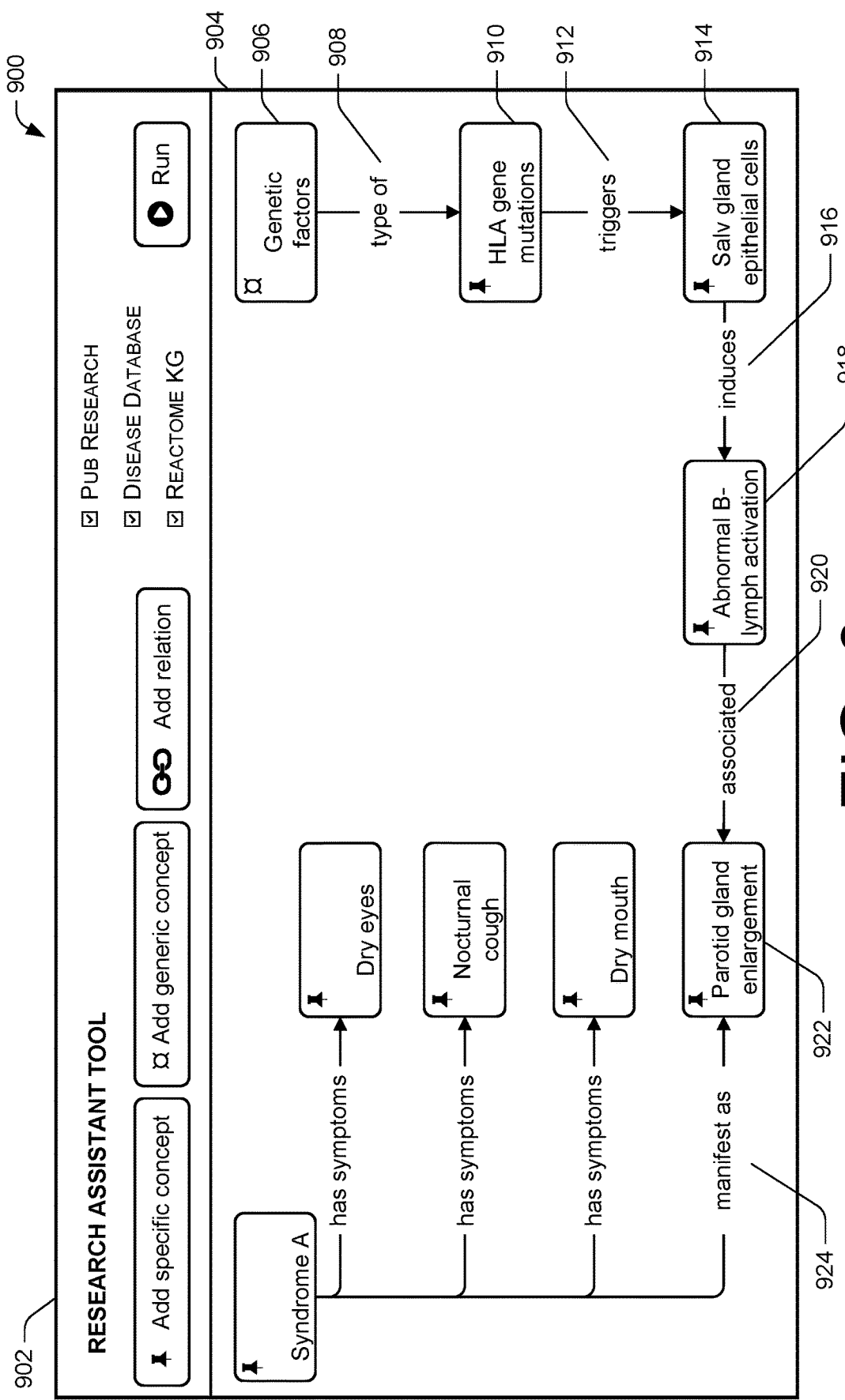
FIG. 9 illustrates an example user interface for displaying multilink results using the research assistant system, as discussed herein.

FIG. 9 illustrates an example user interface 900 for displaying multilink results using the research assistant system, as discussed herein. In some instances, the example user interface 900 may present example user interface 902, including example user interface elements 904, 906, 908, 910, 912, 914, 916, 918, 920, 922, and 924.

The research assistant UI component 208 may generate the example user interface 902 to show the results for performing research with multilink using the research assistant system, as described herein with respect to FIG. 8. The research assistant UI component 208 may generate the example user interface 902 to display and explore the evidence chains by providing an interactive selection element. The example user interface 902 presents the example user interface element 904, which includes an exploration window to allow user input to explore relations or concepts relative to the specific concept "Syndrome A."

The example user interface element 906 highlights a "generic concept" for the research. As depicted, the example user interface 902 is already exploring the "Syndrome A," and the example user interface elements 910, 914, 918, and 922 highlight the interim-specific concepts. The example user interface elements 908, 912, 916, 920, and 924 are relation links between concepts. As described herein with respect to FIG. 8, the user has a selected "Gene mutation induces Cell Reaction causes Manifestation" as a causal schema result for source concept "genetic factors" leading up to target concept "parotid gland enlargement." The resulting causal pathway, as depicted, shows "genetic factor" is a type of "HLA gene mutations" which triggers "sale gland epithelial cells" which induces "abnormal B-lymph activation" and is associated with "parotid gland enlargement."

Figure 10:
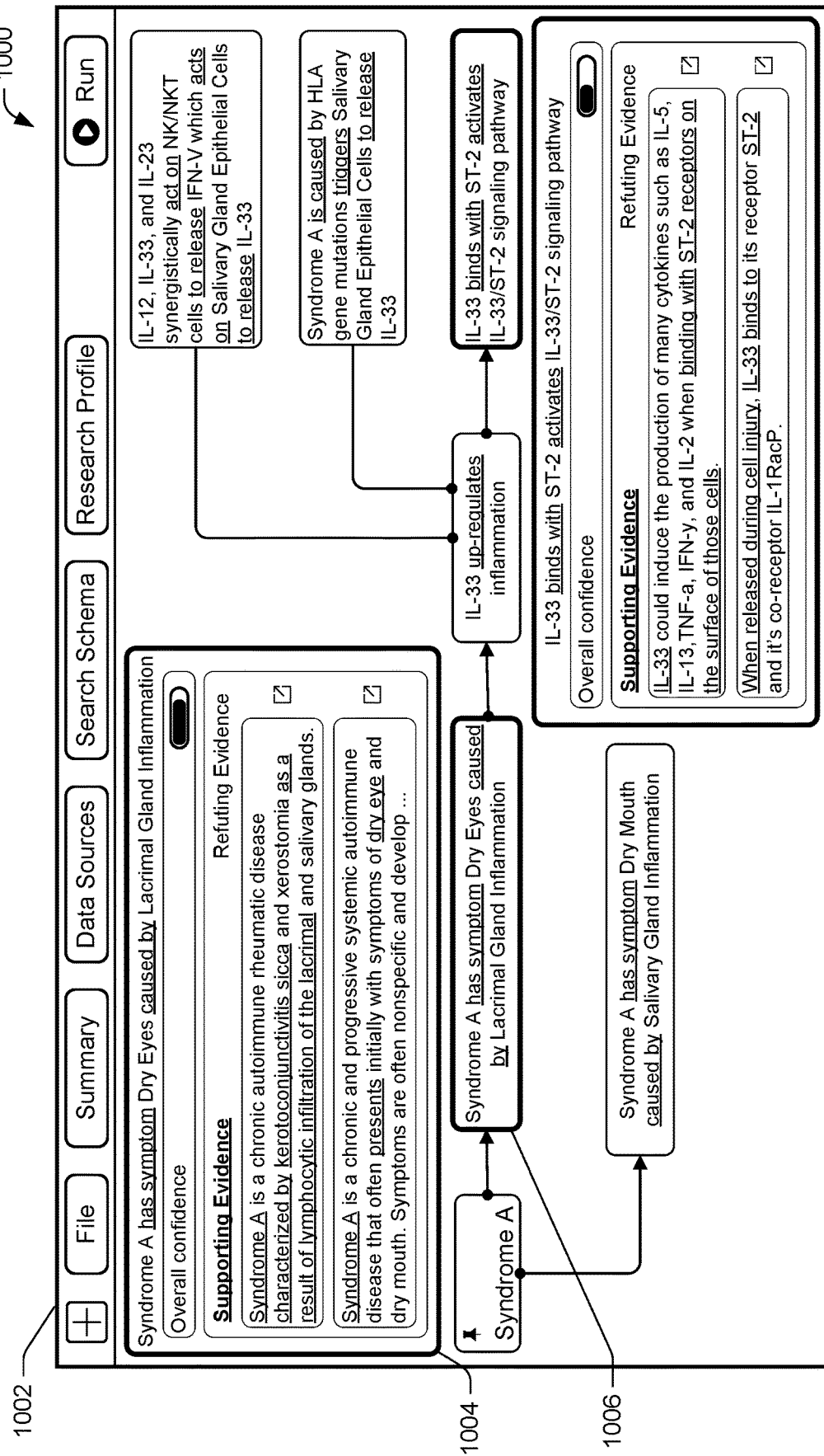
FIG. 10 illustrates an example user interface for performing research with search schema using the research assistant system, as discussed herein.

FIG. 10 illustrates an example user interface 1000 for performing research with search schema using the research assistant system, as discussed herein. In some instances, the example user interface 1000 may present example user interface 1002, including the example user interface elements 1004 and 1006.

The research assistant UI component 208 may generate different user interfaces to guide user input with different levels of complexity, as described herein. The research assistant UI component 208 may generate the example user interface 1002 to initiate research by guiding user input to enter the input query as a "search schema."

The example user interface 1002 may include a visual presentation of query graph that is generated in response to a research, and the nodes of the graph include propositions constructed from combined evidence links from previous research (e.g., from research process illustrated in FIG. 9) with selectable nodes to explore the supporting evidence associated with the node.

In response to selecting the example user interface element 1006, the research assistant UI component 208 may generate the example user interface element 1004.

The example user interface element 1004 allows user input to view supporting evidence or refuting evidence for the research. As depicted, the example user interface 1002 is has been researching concepts related to "Syndrome A." The example user interface element 1006 is highlighting one of the proposition nodes. The example user interface element 1004 allows user input to explore support evidence for the evidence links used to generate the proposition "Syndrome A has symptom dry eyes caused by lacrimal gland inflammation."

In a non-limiting example, the example user interface element 1004 presents evidence for the example user interface element 1006. The example user interface element 1004 illustrates example summaries of evidence passages and an example aggregate confidence. As depicted, the system has high confidence in the proposition cluster for "Syndrome A has symptom dry eyes caused by lacrimal gland inflammation."

As described herein, the query component 210 receives the input query and may conduct a search for the explicit search term "Syndrome A" and search for any articles expressing "Syndrome A" showing symptoms. In the present examples, the query component 210 may find 50 articles about "Syndrome A has symptom dry eyes caused by lacrimal gland inflammation." These 50 articles are the "evidentiary passages" of the proposition node. The evidentiary passages are the "query results," and the query component 210 may output the query results to a natural language understanding (NUJ) engine 216 for processing.

The NLU engine 216 may receive the query results and process the information received as natural language into machine understandable language. The polarity component 222 may perform polarity detection to identify refuting evidentiary passages with semantic context. The NLU engine 216 may output interpreted query results. The interpreted query results may include interpreted relation results and/or interpreted concept results with evidence texts, and the evidence texts may include both supporting and refining evidentiary passages. By providing both supporting and refuting evidence for the same evidence link that the system is trying to build, the polarity component 222 allows the user to compare the evidence for unbiased search results.

The NLU engine 216 may output the interpreted query results for the knowledge aggregation and synthesis engine 224. The knowledge aggregation and synthesis engine 224 may receive the interpreted query results and aggregate the interpreted evidence. As described herein, the knowledge aggregation and synthesis engine 224 may rank the knowledge based on aggregating the information and may score the evidence-based on features metrics. The knowledge aggregation and synthesis engine 224 may output aggregated query results with scored evidence passages. The scoring and ranking component 232 may receive and rank the aggregated query results. The evidence summary component 234 may process the ranked aggregate results with the evidence texts and generate an evidence summary for the ranked aggregate results. The evidence summary component 234 may determine the portion of the evidence passages that are related to the ranked aggregate results and may call the NLU engine 216 to use a semantic textualizer to reverse-translate the semantic interpretations into natural language. The evidence summary component 234 may annotate the clusters with the summarized evidence text.

As depicted in the example user interface element 1004, the system may present the summarized evidence text generated by the evidence summary component 234 and may include a link to the source article.

FIG. 11 illustrates an example user interface 1100 displaying example results with evidence as generated by the research assistant system, as discussed herein. In some instances, the example user interface 1100 may present an example user interface element 1102 and an example user interface 1106.

The research assistant UI component 208 may receive user input on the example user interface element 1102 and trigger example data process 1104. The evidence summary component 234 may run the example data process 1104 and generate the example user interface 1106 to present the research summary.

As depicted, the example user interface 1106 includes a document summary with citations and references. The document summary includes summarized portions of the relevant evidence passages.

Figure 12:
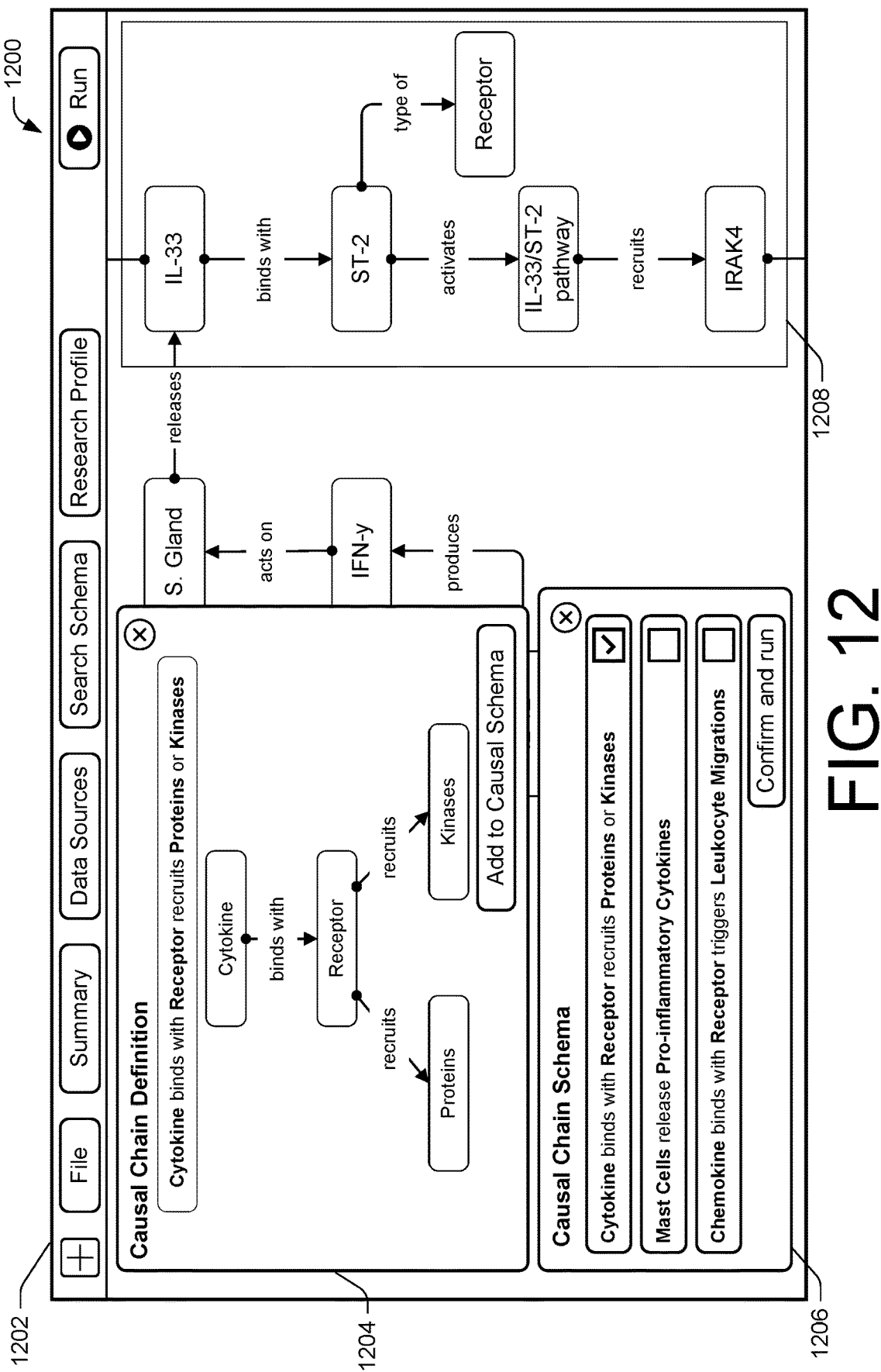
FIG. 12 illustrates an example user interface for performing research with causal chain schema using the research assistant system, as discussed herein

FIG. 12 illustrates an example user interface 1200 for performing research with causal chain schema using the research assistant system, as discussed herein. In some instances, the example user interface 1200 may present example user interface 1202, including example user interface elements 1204, 1206, and 1208.

The research assistant UI component 208 may generate the example user interface 1202 to display and explore causal chain schemas by providing a selection of interactive elements. The research assistant UI component 208 may generate the example user interface element 1204 to include prompts to allow user input to explore causal chain definition. The research assistant UI component 208 provides a prompt for a user to save the current schema with "Add to Causal Schema." By storing the causal schema, the reusable search patterns may be shared with colleagues and teammates and may improve research speed by capturing subject matter expertise as reusable templates.

In a non-limiting example, the research assistant U component 208 may generate the example user interface element 1206 to display a list of causal chain schemas with options to select a schema to conduct a search for.

In response to receiving user input to run the first causal chain schema depicted in the example user interface element 1206, the research assistant system 206 may perform a multilink search and generate the example user interface element 1208 to display the result of the search. As depicted, the example user interface 1202 may present the results as a query graph for further exploration.

Figure 13:
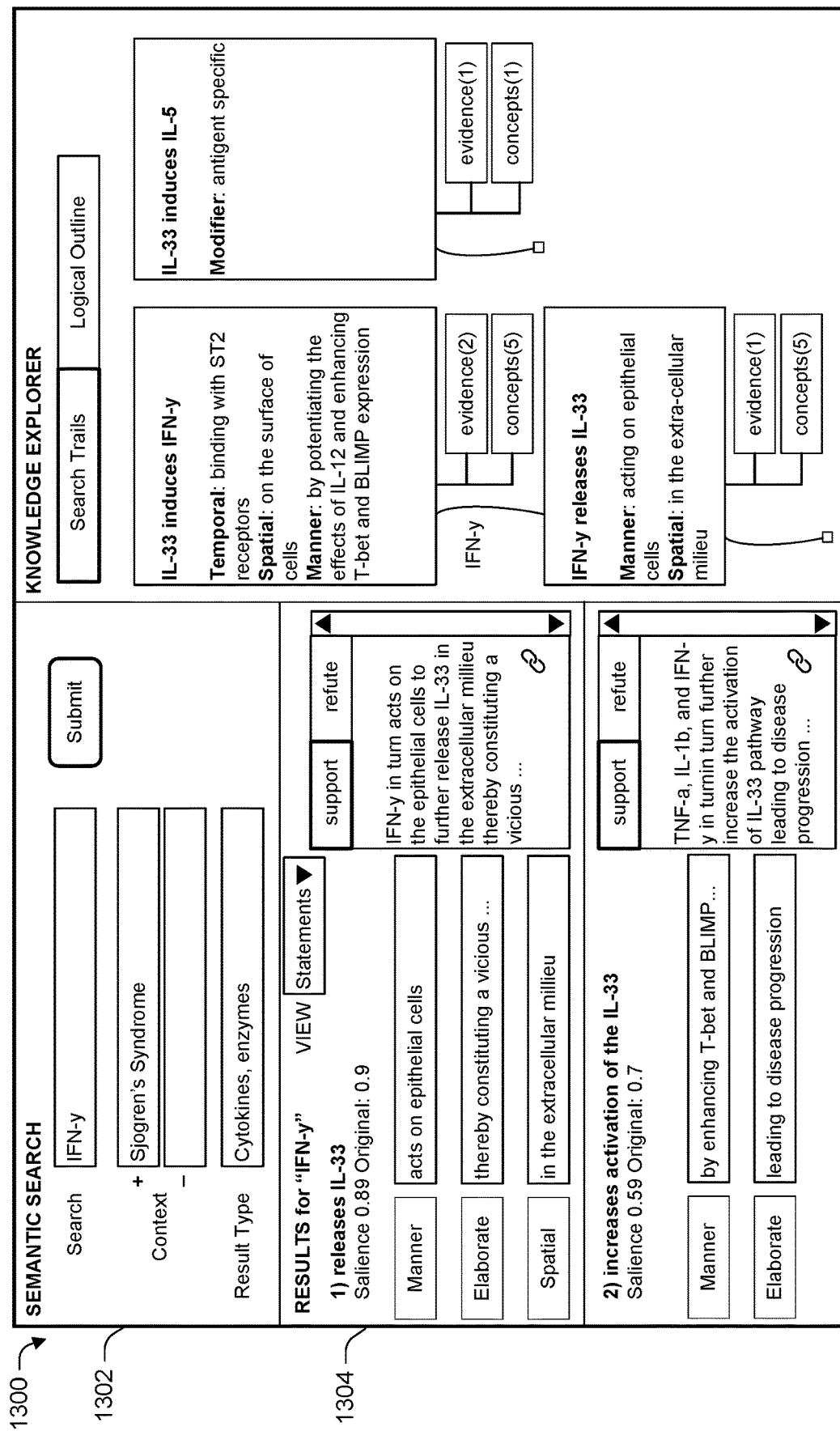
FIG. 13 illustrates an example user interface including a search tool, a results exploration tool, and a knowledge explorer tool for the research assistant system, as discussed herein.

FIG. 13 illustrates an example user interface 1300, including a semantic search tool, a results exploration tool, and a knowledge exploration tool, as discussed herein. In some instances, the example user interface 1300 may present example user interface elements 1302, 1304, and 1306.

The example user interface 1300 provides a general overview of the example user interface elements 1302, 1304, and 1306. The individual elements of the semantic search tool, the results exploration tool, and the knowledge exploration tool will be discussed in greater detail herein with respect to FIGS. 14, 15, and 16.

The research assistant UI component 208 may generate a user interface to guide user input to enter the search query and explore the results and evidence chains, as described herein.

In a non-limiting example, the research assistant UI component 208 may generate the example user interface element 1302 to initiate a semantic search by guiding user input to enter the query. As depicted, a specific concept is "IFN-y," a search context is "Sjogren's Syndrome," and the search condition is constraint by the result type "cytokines" or "enzymes." The search engine will receive the search context and use it as "biased data" to influence the search. For instance, the query component 210 will search for articles with the explicit search term "IFN-y," which results in some type of "cytokines" or "enzymes" with a bias for results with the context of "Sjogren's Syndrome."

The research assistant UI component 208 may generate a user interface with the results exploration tool, including the example user interface elements 1304 to explore the results and view the evidence text.

The research assistant UI component 208 may generate a user interface with the knowledge exploration tool, including the example user interface elements 1306 to explore the evidence chains.

Figure 14:
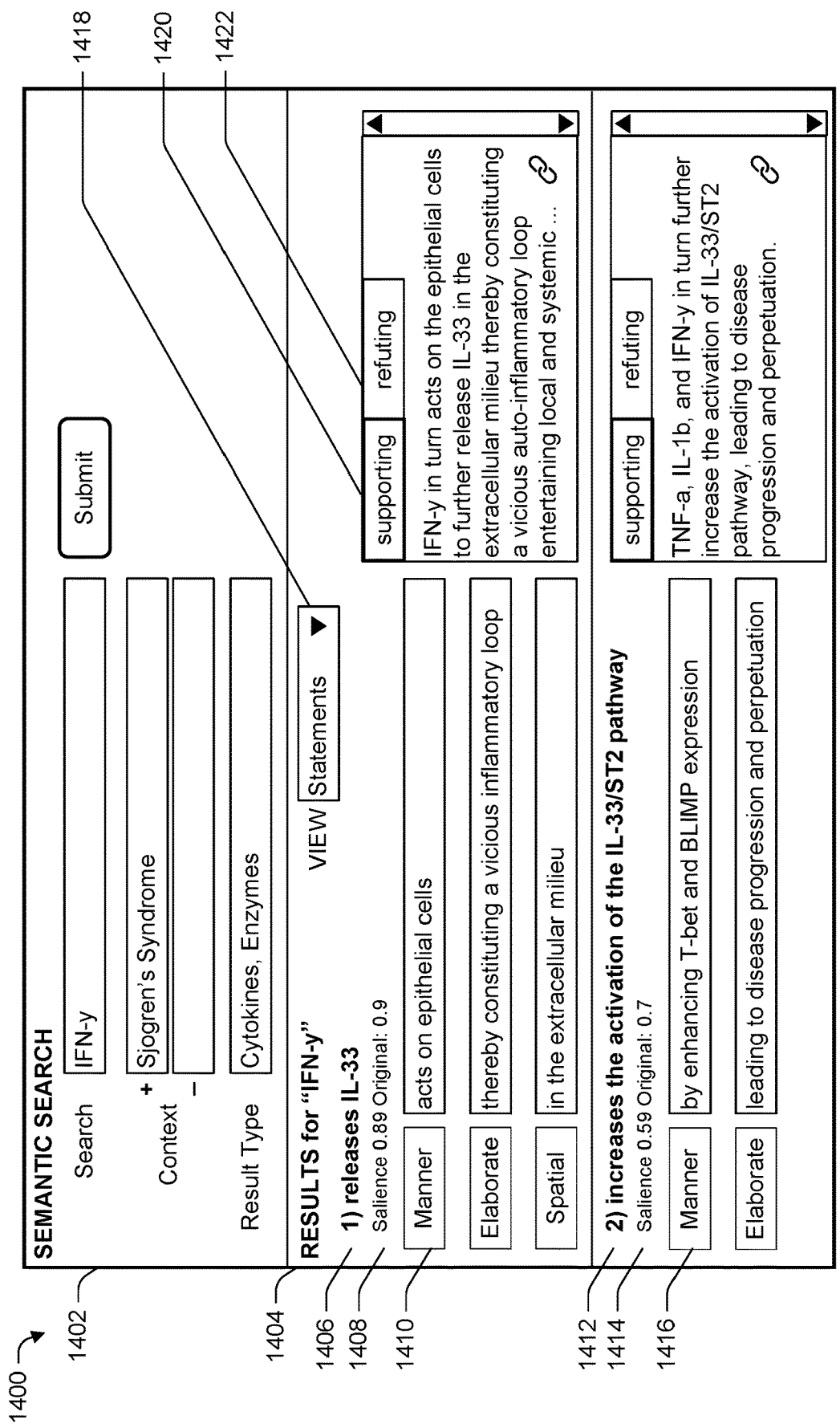
FIG. 14 illustrates an example user interface including a search tool and a results exploration tool for the research assistant system, as discussed herein.

FIG. 14 illustrates an example user interface 1400, including a semantic search tool and results exploration tool, as discussed herein. In some instances, the example user interface 1400 may present example user interface elements 1402, 1404, 1406, 1408, 1410, 1412, 1414, 1416, 1418, 1420, and 1422.

The research assistant UI component 208 may generate a user interface 1400 to guide user input to enter the search query and explore the results and evidence chains, as described herein, as described herein with respect to FIG. 13.

The research assistant UI component 208 may generate the example user interface element 1402 to initiate a search by guiding user input to enter search parameters. As depicted in the present example, the query input includes searching for a concept "IFN-y" with the context of "Sjogren's Syndrome." The query component 210 may use the context and indicators for increasing ("+") or decreasing ("−") a search engine bias when performing the search. The result type is a constraint parameter used to limit the search results by the search constraint type. As described herein, the NLU engine 216 may use the semantic parser 218 to process query results and interpret the results as interpreted query results, and the semantic fit component 220 may check that the semantic type in the input query matches that of the interpreted query results.

The research assistant UI component 208 may generate the example user interface element 1404 to present a results exploration tool.

In a non-limiting example, the example user interface element 1406 may present a first result cluster "releases IL-33" for exploration. The originality and saliency component 228 may score evidence passages associated with the first result cluster and generate saliency score and originality score as indicated by the example user interface element 1408.

The semantic parser 218 may interpret the relevant portion of evidence text for the first cluster "releases IL-33" and generate semantic indicators for the text indicated by the example user interface element 1410. The example user interface elements 1410 present the information associated with the semantic schema to indicate how the NW engine 216 is deconstructing the evidence and interpreting conditional information.

As described herein, the present system configures the semantic parser 218 to use a relational qualification schema (RQS) to describe or qualify a set of conditions under which a relation may be true. In machine language, a relation is a named semantic link between concepts, and relations are verb-senses with multiple name roles. Natural human language has words with multiple inferred meanings, while machine language looks for a direct match; thus, knowledge representation allows for a machine to read the same word and may correctly interpret the meaning. A relation word may include multiple meanings to a human researcher, but not for a machine; thus, the system replaces the relation link with a semantic link to allow the system to look for "relation" words and may accept semantically similar words. A semantic link is a relational representation that connects two representations (e.g., concepts), supports interpretation and reasoning with other links, and facilitates predictive operations on representations. The semantic parser 218 may generate the interpreted query results by interpreting the query results in a semantic schema; including the constructed set of semantic indicators. The semantic schema may map interpreted concepts to "concept type" and interpreted relations to "semantic type."

In various examples, the semantic parser 218 may define the semantic indicators including one or more conditions for the occurrence of the relation, the one or more conditions may include a temporal indicator, a spatial indicator, an instrument indicator, a cause indicator, a purpose indicator, an extent indicator, or a modal indicator. A temporal indicator of a time at which the relation is to occur. A spatial indicator of a location at which the relation is to occur. An instrument indicator of tool used to induce the relation to occur. A cause indicator of an identity of a concept that causes relation to occur. A purpose indicator of a purpose for the relationship to occur, an extent indicator for a time period for the relationship to occur. A modal indicator of certainty for the relationship to occur.

As depicted in the example user interface elements 1410, the NLU engine 216 has constructed semantic indicators that include manner, "acts on epithelial cells," and spatial, "in the extracellular milieu."

The example user interface element 1412 may present a second result cluster for exploration. The originality and saliency component 228 may score evidence passages associated with the second result cluster and generate saliency score and originality score as indicated by the example user interface element 1414.

The semantic parser 218 may interpret the relevant portion of evidence text for the first cluster and generate semantic indicators for the text indicated by the example user interface element 1416. As depicted in the example user interface elements 1416, the NLU engine 216 has constructed semantic indicator that includes manner, "by enhancing T-bet and BLIMP expression."

In some examples, the research assistant UI component 208 may generate the example user interface element 1418 to receive user input to select evidence to view. As depicted, the example user interface element 1418 indicates view setting for statements found in the evidence text. The research assistant UI component 208 may generate options to view supporting evidence via the example user interface element 1420, or refuting evidence, via the example user interface element 1422.

Figure 15:
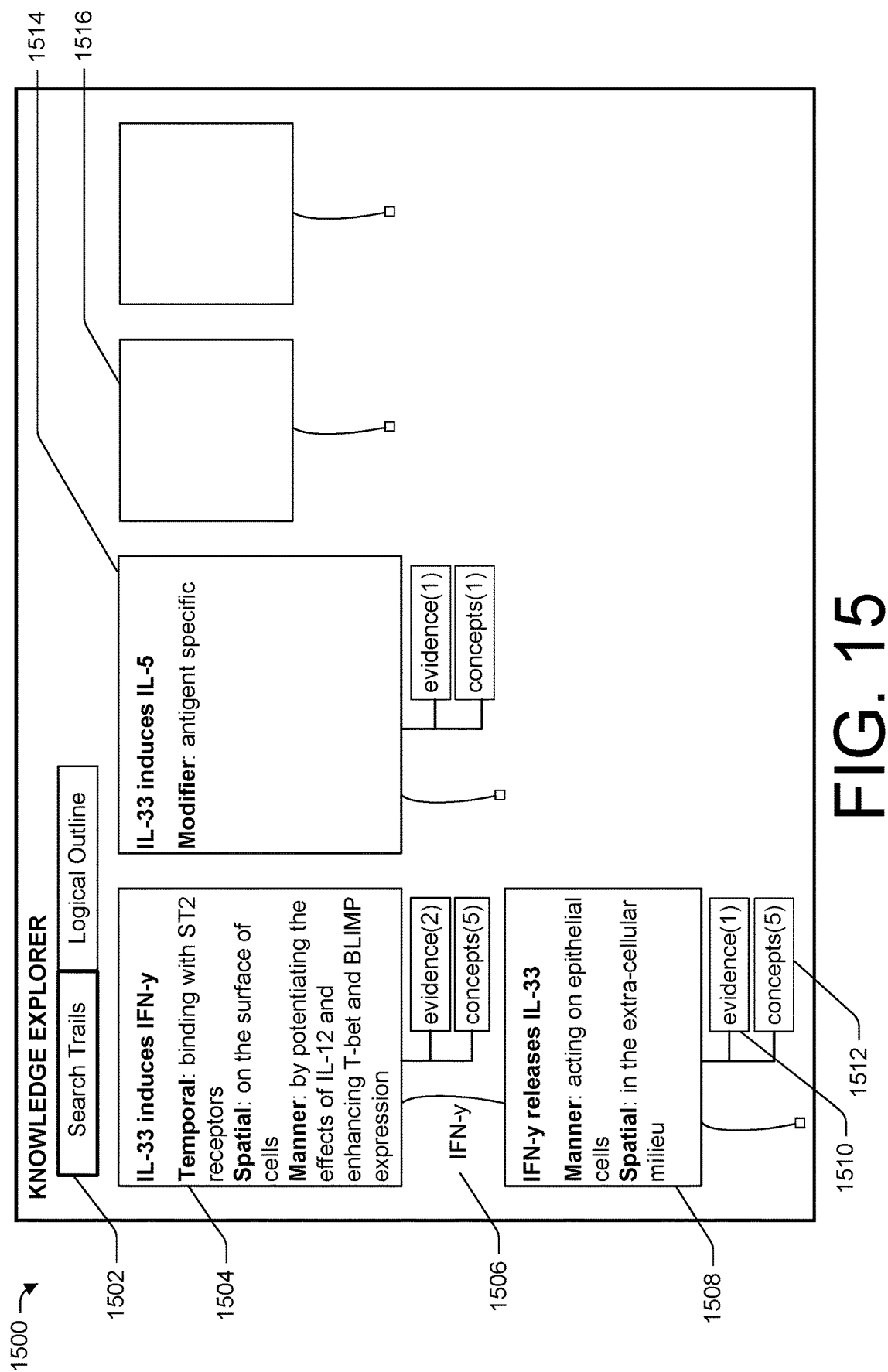
FIG. 15 illustrates an example user interface of a knowledge exploration tool illustrating a search trails view for the research assistant system, as discussed herein.

FIG. 15 illustrates an example user interface 1500 of a knowledge exploration tool including search trails of research, as discussed herein. In some instances, the example user interface 1500 may present example user interface elements 1502, 1504, 1506, 1508, 1510, 1512, 1514, and 1516.

The research assistant UI component 208 may generate the example user interface 1500 with a knowledge explorer to guide user input to explore the research results and evidence chains, as described herein with respect to FIGS. 13 and 14.

As previously described herein with respect to FIG. 14, the research assistant UI component 208 may generate the example user interface element 1402 to initiate a search by guiding user input to enter search parameters. As depicted in the present example, the query input includes searching for a concept "IFN-y" with the context of "Sjogren's Syndrome."

In a non-limiting example, the example user interface element 1406 may present a first result cluster "releases IL-33" for exploration. The originality and saliency component 228 may score evidence passages associated with the first result cluster and generate saliency score and originality score as indicated by the example user interface element 1408. The semantic parser 218 may interpret the relevant portion of evidence text for the first cluster "releases IL-33" and generate semantic indicators for the text indicated by the example user interface element 1410. The example user interface elements 1410 present the information associated with the semantic schema to indicate how the NLU engine 216 is deconstructing the evidence and interpreting conditional information.

As described herein, the present system configures the semantic parser 218 to use a relational qualification schema (RQS) to describe or qualify a set of conditions under which a relation may be true. In machine language, a relation is a named semantic link between concepts, and relations are verb-senses with multiple name roles. Natural human language has words with multiple inferred meanings, while machine language looks for a direct match; thus, knowledge representation allows for a machine to read the same word and may correctly interpret the meaning. A relation word may include multiple meanings to a human researcher, but not for a machine; thus, the system replaces the relation link with a semantic link to allow the system to look for "relation" words and may accept semantically similar words. A semantic link is a relational representation that connects two representations (e.g., concepts), supports interpretation and reasoning with other links, and facilitates predictive operations on representations. The semantic parser 218 may generate the interpreted query results by interpreting the query results in a semantic schema, including the constructed set of semantic indicators. The semantic schema may map interpreted concepts to "concept type" and interpreted relations to "semantic type."

The research assistant UI component 208 may generate the example user interface element 1502 to present a knowledge exploration tool.

In a non-limiting example, the research assistant UI component 208 may generate the example user interface element 1502 to guide user input for viewing the evidence as "Search Trails" or "Logical Outline." As depicted in the present example, an example evidence chain includes two evidence documents as nodes: the example user interface element 1504, and the example user interface element 1508.

As depicted in the example user interface element 1504, the NLU engine 216 has constructed semantic indicators that include manner, "acts on epithelial cells," and spatial, "in the extracellular milieu."

As depicted in the example user interface elements 1508, the NLU engine 216 has constructed semantic indicator that includes manner, "by enhancing T-bet and BLIMP expression."

The example user interface element 1506 indicate the connecting concept "IFN-y" between the two evidence documents. The originality and saliency component 228 may score evidence passages and display a count of evidence documents aggregated via the example user interface element 1510 and a count of concept appearance via the example user interface element 1512.

In some examples, the research assistant LI component 208 may present the example user interface element 1514 to explore another evidence document citing "IL-33 induces IL-5." In various examples, the research assistant UI component 208 may present the example user interface element 1516 with a blank search trail to prompt user input for adding another search.

Figure 16:
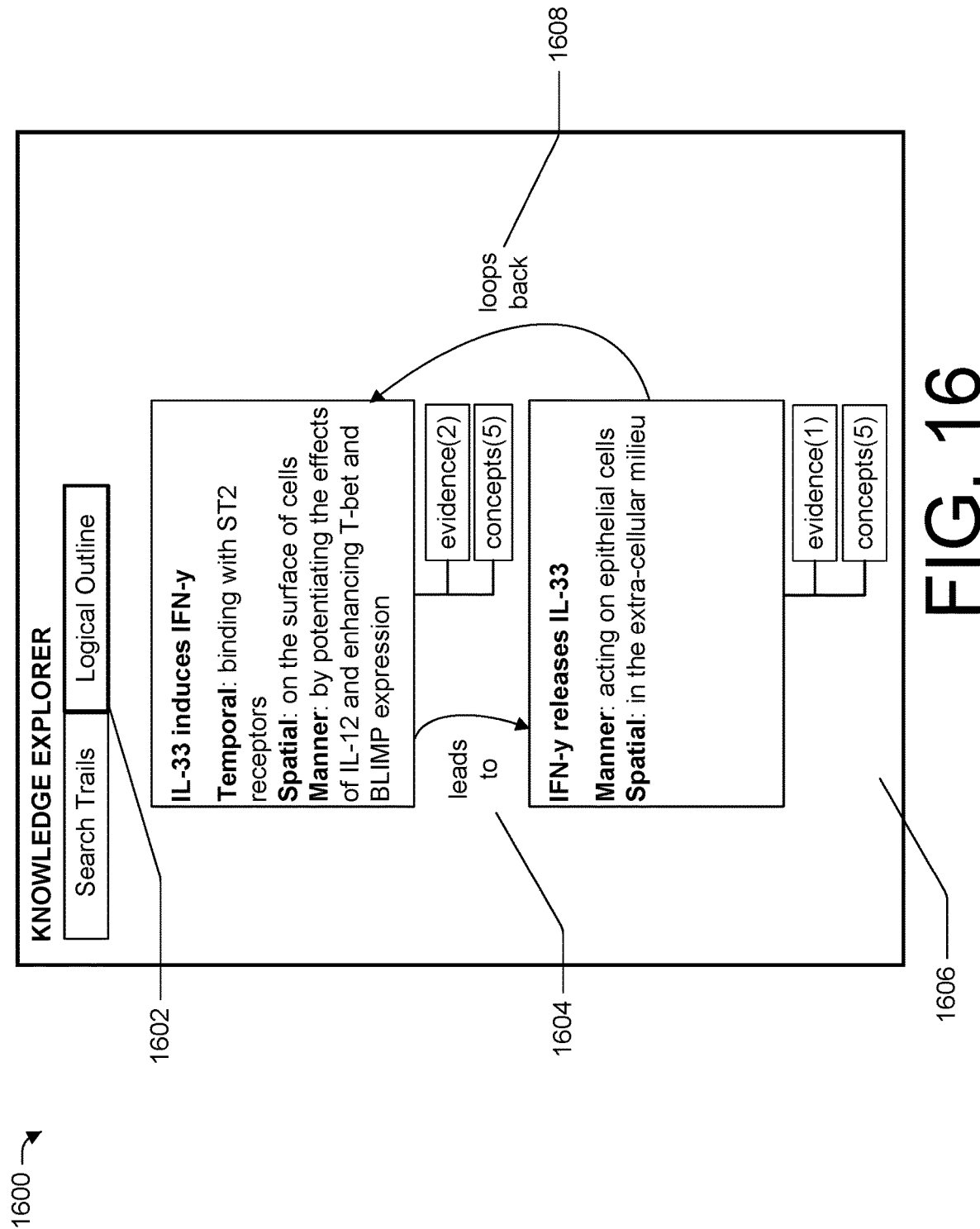
FIG. 16 illustrates an example user interface of a knowledge exploration tool illustrating a logical outline view for the research assistant system, as discussed herein.

FIG. 16 illustrates an example user interface 1600 of a knowledge exploration tool, including a logical outline of research, as discussed herein. In some instances, the example user interface 1600 may present example user interface elements 1602, 1604, 1606, and 1608.

The research assistant UI component 208 may generate a user interface to guide user input to explore the research results and evidence chains, as described herein.

In a non-limiting example, the research assistant UI component 208 may generate the example user interface element 1602 to guide user input for viewing the evidence as "Logical Outline." As depicted, the present example evidence chain provides a logical outline graph representation of the two example search trails, as described herein with respect to and depicted in FIG. 15. The knowledge aggregation and synthesis engine 224 may aggregate and synthesize the information from the two example search trails to generate the example query graph illustrated as example user interface element 1606.

As described herein, the statistical and neural inference engine 240 and the query component 210 may find articles with "A relates to B" and "C relates to D" and may leverage evidence links stored in the structured database and apply the inference engine to create an evidence chain of "A relates to B," "B relates to C," and "C relates to D. In the present example, the statistical and neural inference engine 240 may use the current links found and determine that a first evidence link connects back to a second evidence link. For instance, as described herein with respect to FIG. 15, the first evidence link "IL-33 induces IFN-y" leads to the second evidence link "IFN-y releases IL-33" with a third evidence link "IL-33 induces IL-5." The statistical and neural inference engine 240 may determine that by combining the third evidence link, there is logical evidence for "A relates to B in a first manner" and "B relates to A in a second manner." The example query graph includes the example user interface element 1604 and 1608, indicating the relation links between the two evidence passages.

Figure 17:
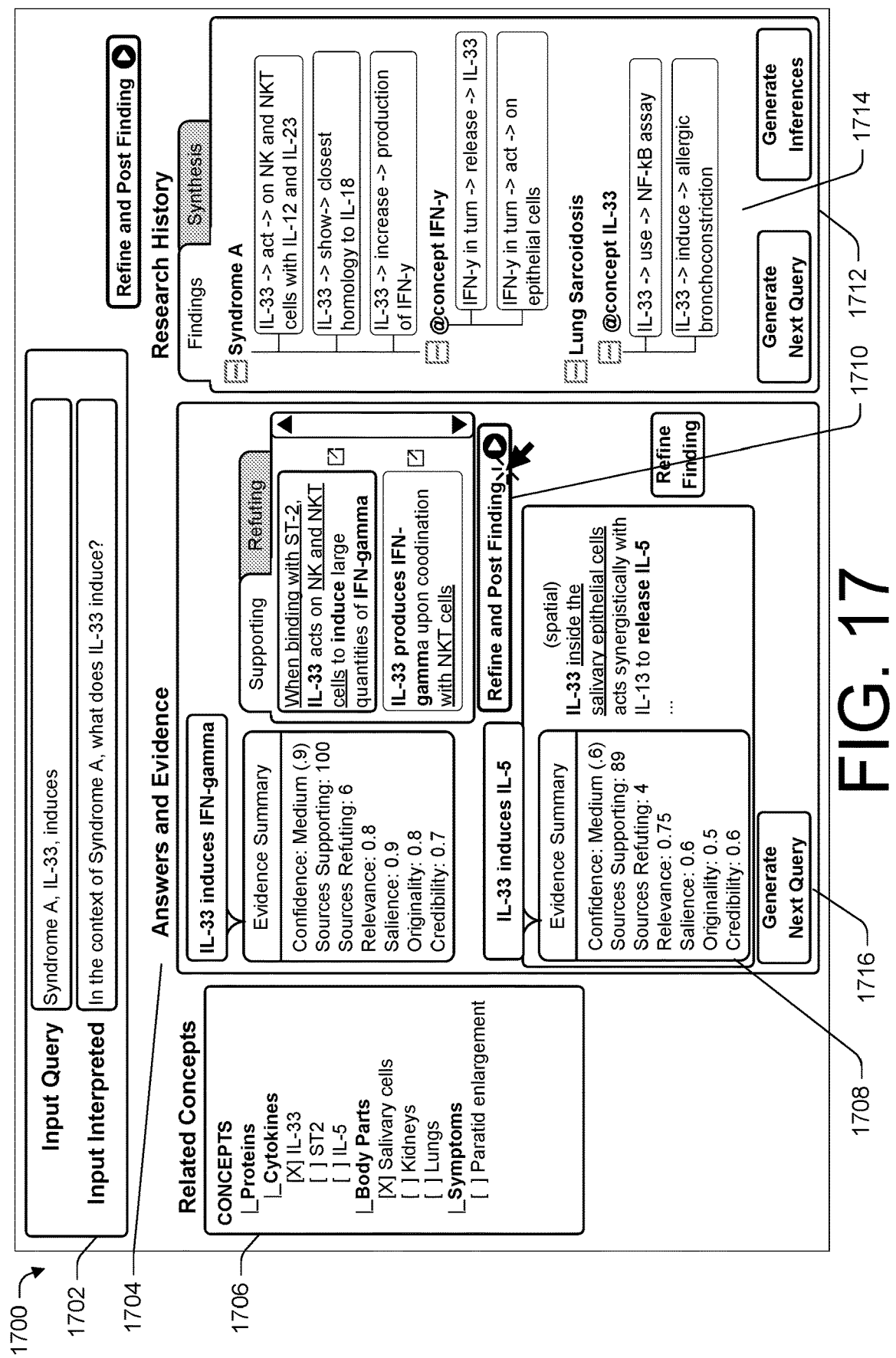
FIG. 17 illustrates an example user interface for performing research using the research assistant system, as discussed herein.

FIG. 17 illustrates an example user interface 1700 for performing research using the research assistant system, as discussed herein. In some instances, the example user interface 1700 may present example user interface elements 1702, 1704, 1706, 1708, 1710, 1712, 1714, and 1716.

The research assistant UI component 208 may generate a user interface to guide user input for an input query and exploration of evidence findings, as described herein.

In a non-limiting example, the research assistant UI component 208 may generate the example user interface element 1702 to guide user input for entering an input query. As depicted in the present example, the example user interface element 1702 may receive the input query as a structured query and present the interpreted input as a natural language question. In some examples, the query component 210 may receive the input query as a natural language question and present the interpreted structure in the input query.

The research assistant UI component 208 may generate the example user interface element 1704 to display a ranked list of answers in response to a query. As depicted in the example user interface element 1704, individual answers in the ranked list of answers include associated evidence and scores. The natural language understanding (NLU) engine 216 and the knowledge aggregation and synthesis engine 224 may determine scores for features, including but not limited to aggregation confidence, saliency, relevance, originality, author credibility, and the like.

The research assistant system 206 may generate example user interface element 1706 to include an aspect filter that, based on the input query, may discover and rank the top relevant related concepts and lists them within the interface element 1706. The aspect filter can be used to filter the search.

The research assistant system 206 may generate example user interface element 1708 to include the evidence. The natural language understanding (NLU) engine 216 may identify supporting or refuting evidence. The example user interface element 1708 may present the evidence with classification by supporting or refuting and with semantically annotated with contextual indicators, including, but not limited to, temporal, spatial, manner/instrument, cause/effect, purpose, extent, modal, and the like.

The research assistant system 206 may generate the example user interface element 1710 to include a prompt to refine the finding. The example user interface element 1710 can refine any discovered relationships and/or provide the option to add or edit argument concepts to create a finding of interest.

The research assistant system 206 may generate the example user interface element 1712 to present the research results in a "Findings" panel. User input may be received to move results from the example user interface element 1704 to the Findings panel. The example user interface element 1712 may include a prompt for user input to record the search history. User input received on any of the findings in this history view may also update the query and/or results views to restore the corresponding finding.

In some examples, the research assistant system 206 may receive user input on the example user interface element 1714 with a selection of a set of findings and a request to generate inferences. In response to the generate inferences request, the research assistant system 206 may use a domain theory and a symbolic reasoning engine 238 and/or a statistical and neural inference engine 240 to generate inferences.

In various examples, the research assistant system 206 may receive user input with a selection of a sub-span of texts and selection of the example user interface element 1716 to "Generate Next Query." In response to the generate next query request, the research assistant system 206 may analyze the selected text(s) based on the context and generate a structured query to execute next.

Figure 18:
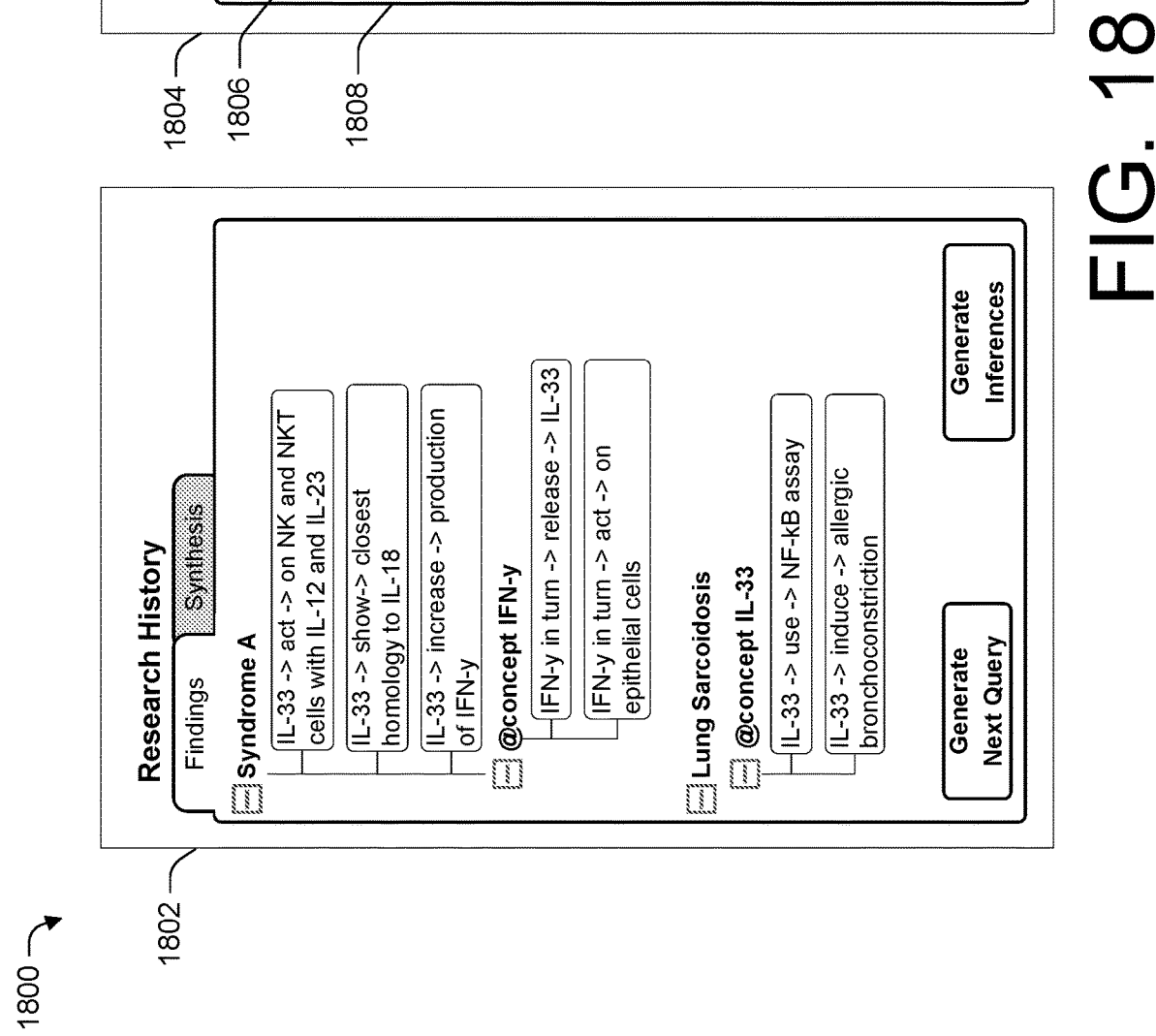
FIG. 18 illustrates an example user interface illustrating synthesized research findings to generate a research graph, as discussed herein.

FIG. 18 illustrates an example user interface 1800, including a research graph using the research assistant system, as discussed herein. In sonic instances, the example user interface 1800 may present example user interface elements 1802, 1804, 1806, and 1808.

The research assistant UI component 208 may generate a user interface to guide user input for exploration of evidence findings and synthesized findings, as described herein.

In a non-limiting example, the research assistant UI component 208 may generate the example user interface element 1802 as previously presented in FIG. 17. As depicted in the present example, the research assistant system 206 may logically organize the research data based on current "findings" state and may present the data in different layouts and/or different visualization, such as a graph, a timeline, a map, or a structured document. The example user interface element 1804 may be displayed in response to selecting the example user interface element 1806 to organize the research data in a "Graph" view. In some examples, the research assistant UI component 208 may generate the example user interface element 1808 to illustrate the query graph of the findings.

Figure 19:
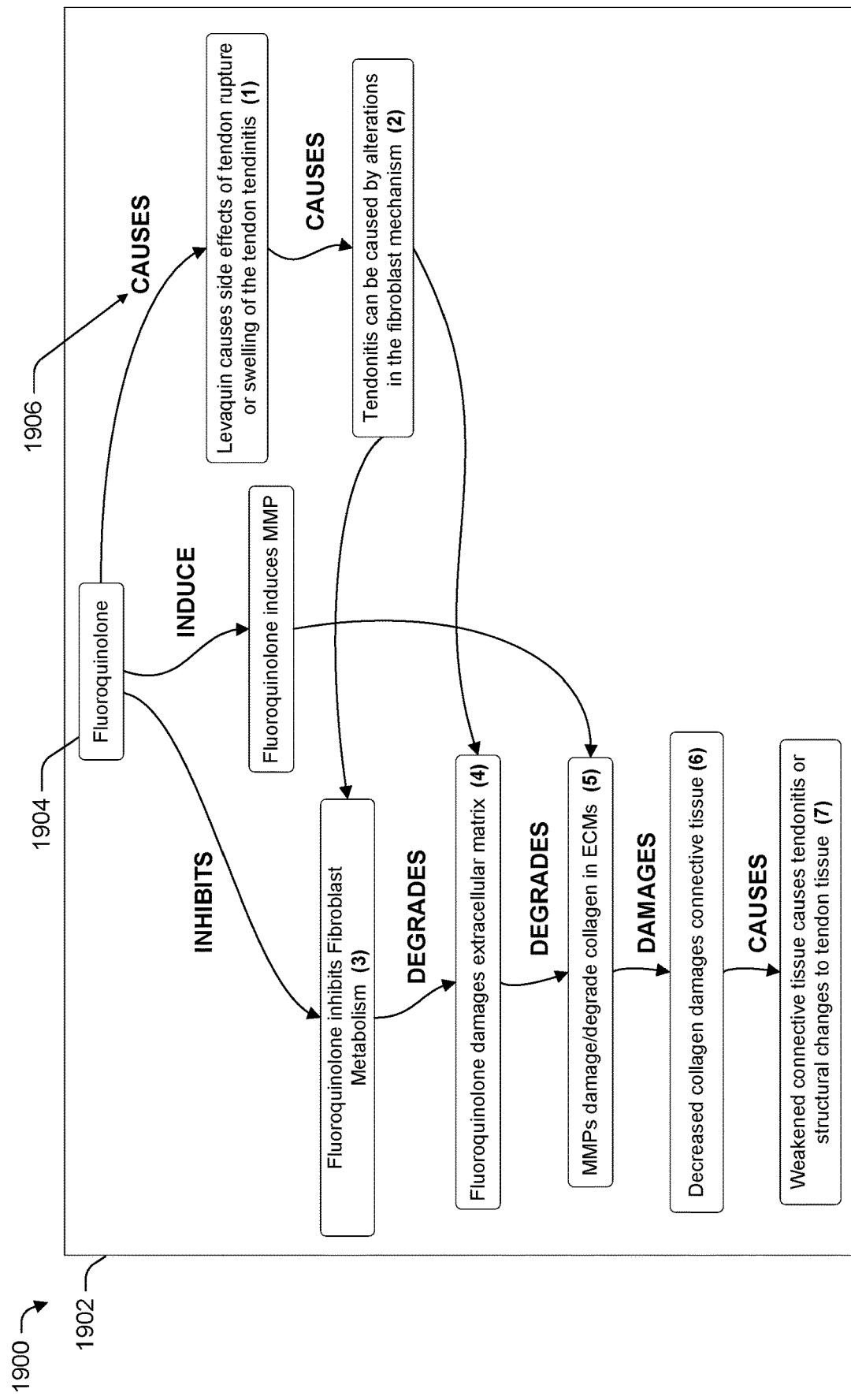
FIG. 19 illustrates an example user interface displaying a research graph generated by the research assistant system, as discussed herein.

FIG. 19 illustrates an example user interface 1900 for performing research using the research assistant system, as discussed herein. In some instances, the example user interface 1900 may present example user interface elements 1902, 1904, and 1906.

The research assistant UI component 208 may generate a user interface to guide user input for exploration of evidence findings and graph views, as described herein.

In a non-limiting example, the research assistant UI component 208 may generate the example user interface element 1902 as an example presentation of a query graph of the findings. As depicted in the present example, the example user interface element 1904 may display the source concept at the top of the query graph with connected evidence flowing from the source concept. In some examples, the research assistant UI component 208 may generate the query graph to illustrate a visual representation for the query graph and may indicate "concepts" as nodes and "relationships" as links or edges (e.g., the example user interface element 1906) that connects the concepts.

Figure 20:
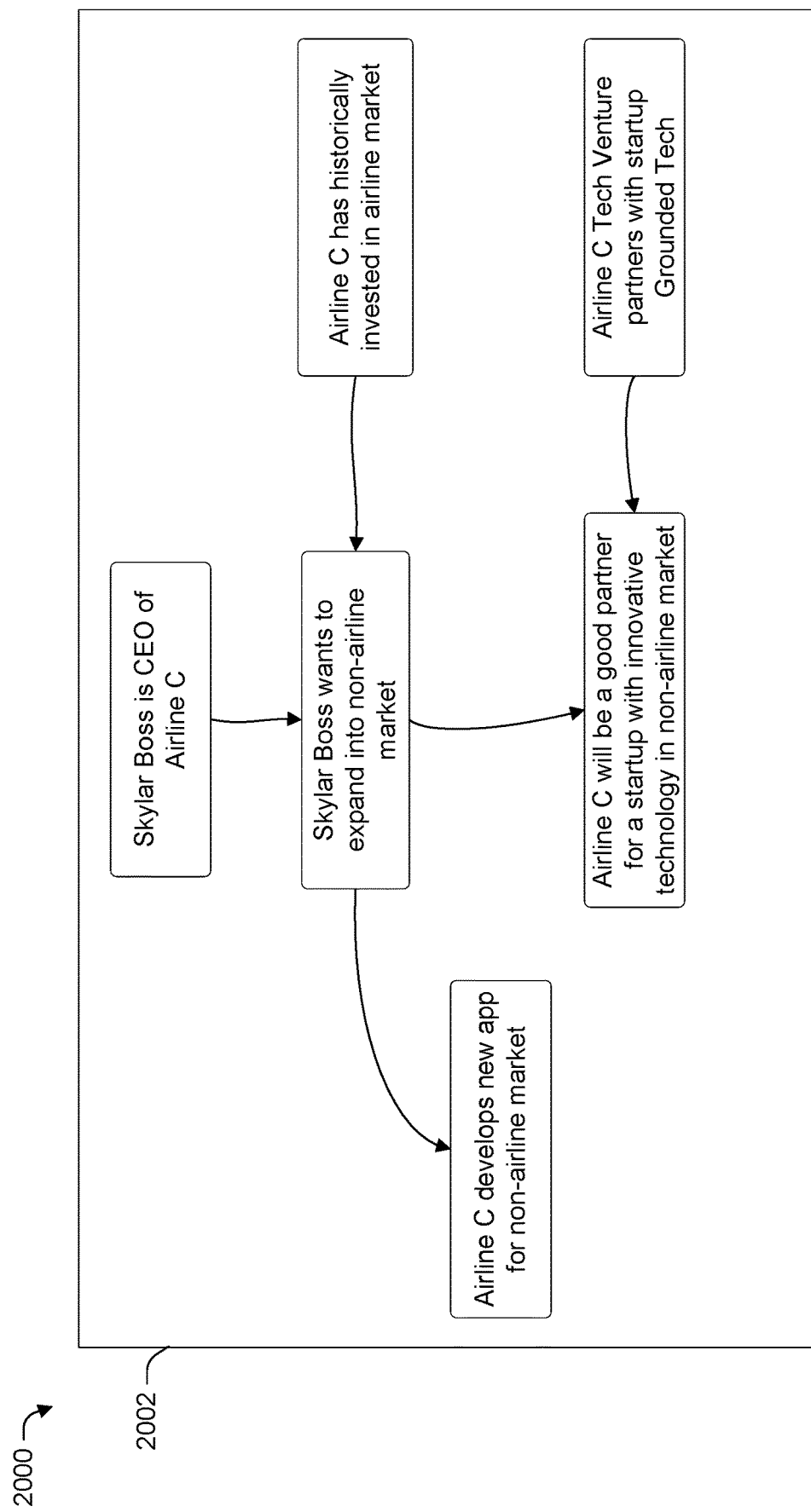
FIG. 20 illustrates an example user interface for performing market research using the research assistant system, as discussed herein.

FIG. 20 illustrates an example user interface 2000 for performing research using the research assistant system, as discussed herein. In some instances, the example user interface 2000 may present example user interface element 2002.

The research assistant Iii component 208 may generate a user interface to guide user input for exploration of evidence findings and graph views, as described herein.

In a non-limiting example, the research assistant UI component 208 may generate the example user interface element 2002 as an example presentation of a query graph of the research results in an airline and ground traveling domain. As described herein, the research assistant system 206 is configured to be used to assist with research across any domain. In particular, the use of the research assistant system 206 to generate the example user interface element 2002 is a non-limiting example of how the present system can be used to assist in conducting research.

As depicted, the example user interface element 2002 may display a query graph with marketing research for whether a particular airline company would be a good market partner based on evidence gathered from a public news source. For instance, the articles found may relate to: (1) "Skylar Boss is CEO of Airline C," (2) "Airline C has historically invested in airline market," (3) "Skylar Boss wants to expand into non-airline market," (4) "Airline C develops new app for non-airline market," and (5) "Airline C Tech Venture partners with startup Grounded Tech." By combining the articles, the system can determine the response as "Airline C will be a good partner for a startup with innovative technology in non-airline market."

FIGS. 21-28 are flow diagrams of illustrative processes. The example processes are described in the context of the environment of FIG. 2 but are not limited to that environment. The processes are illustrated as a collection of blocks in a logical flow graph, which represents a sequence of operations that can be implemented in hardware, software, or a combination thereof. In the context of software, the blocks represent computer-executable instructions stored on one or more computer-readable media 204 that, when executed by one or more processors 202, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes. The processes discussed below may be combined in any way to create derivative processes that are still within the scope of this disclosure.

FIG. 21 is a flow diagram of illustrative process 2100 for a research assistant tool to identify relationship links between concepts supported by evidence, as discussed herein. The process 2100 is described with reference to the system 100 and may be performed by one or more of the computing device(s) 102 and/or in cooperation with any one or more of the device(s) 106. Of course, the process 2100 (and other processes described herein) may be performed in other similar and/or different environments.

At operation 2102, the process may include receiving an input query that is associated with a research topic and that includes a first concept and a second concept, wherein the first concept and the second concept are used by a research assistant tool to determine relation links associated with the research topic. For instance, the computing device(s) 102 or the device(s) 106 may receive, via a graphical user interface (GUI) presented via a user device, an input query that is associated with a research topic and that includes a first concept and a second concept, wherein the first concept and the second concept are used by a research assistant tool to determine relation links associated with the research topic.

At operation 2104, the process may include identifying one or more evidence passages that include one or more semantic links between the first concept and the second concept. For instance, the computing device(s) 102 or the device(s) 106 may identify, by a query component associated with the research assistant tool, one or more evidence passages that include one or more semantic links between the first concept and the second concept, wherein at least one of the one or more semantic links is a structured relational representation that connects the first concept and the second concept, and wherein the one or more evidence passages include one or more portions of a knowledge data source.

At operation 2106, the process may include determining that the one or more semantic links include one or more relational representations connecting the first concept and the second concept. For instance, the computing device(s) 102 or the device(s) 106 may determine, by a natural language understanding engine associated with the research assistant tool, that the one or more semantic links include one or more relational representations connecting the first concept and the second concept.

At operation 2108, the process may include determining one or more relation clusters by aggregating the one or more relational representations based at least in part on a degree of semantic similarity between the one or more relational representations. For instance, the computing device(s) 102 or the device(s) 106 may determine, by a knowledge aggregation engine associated with the research assistant tool, one or more relation clusters by aggregating the one or more relational representations based at least in part on a degree of semantic similarity between the one or more relational representations.

At operation 2110, the process may include determining an aggregation confidence associated with a relation cluster of the one or more relation clusters, wherein the aggregation confidence is based at least in part on a reliability score of a portion of the one or more evidence passages. For instance, the computing device(s) 102 or the device(s) 106 may determine, by the knowledge aggregation engine, an aggregation confidence associated with a relation cluster of the one or more relation clusters, wherein the aggregation confidence is based at least in part on a reliability score of a portion of the one or more evidence passages.

At operation 2112, the process may include determining that a query result includes the relation cluster based at least in part on ranking of the one or more relation clusters, the relation cluster including a relation expression between the first concept and the second concept. For instance, the computing device(s) 102 or the device(s) 106 may determine that a query result includes the relation cluster based at least in part on ranking of the one or more relation clusters, the relation cluster including a relation expression between the first concept and the second concept.

Figure 22:
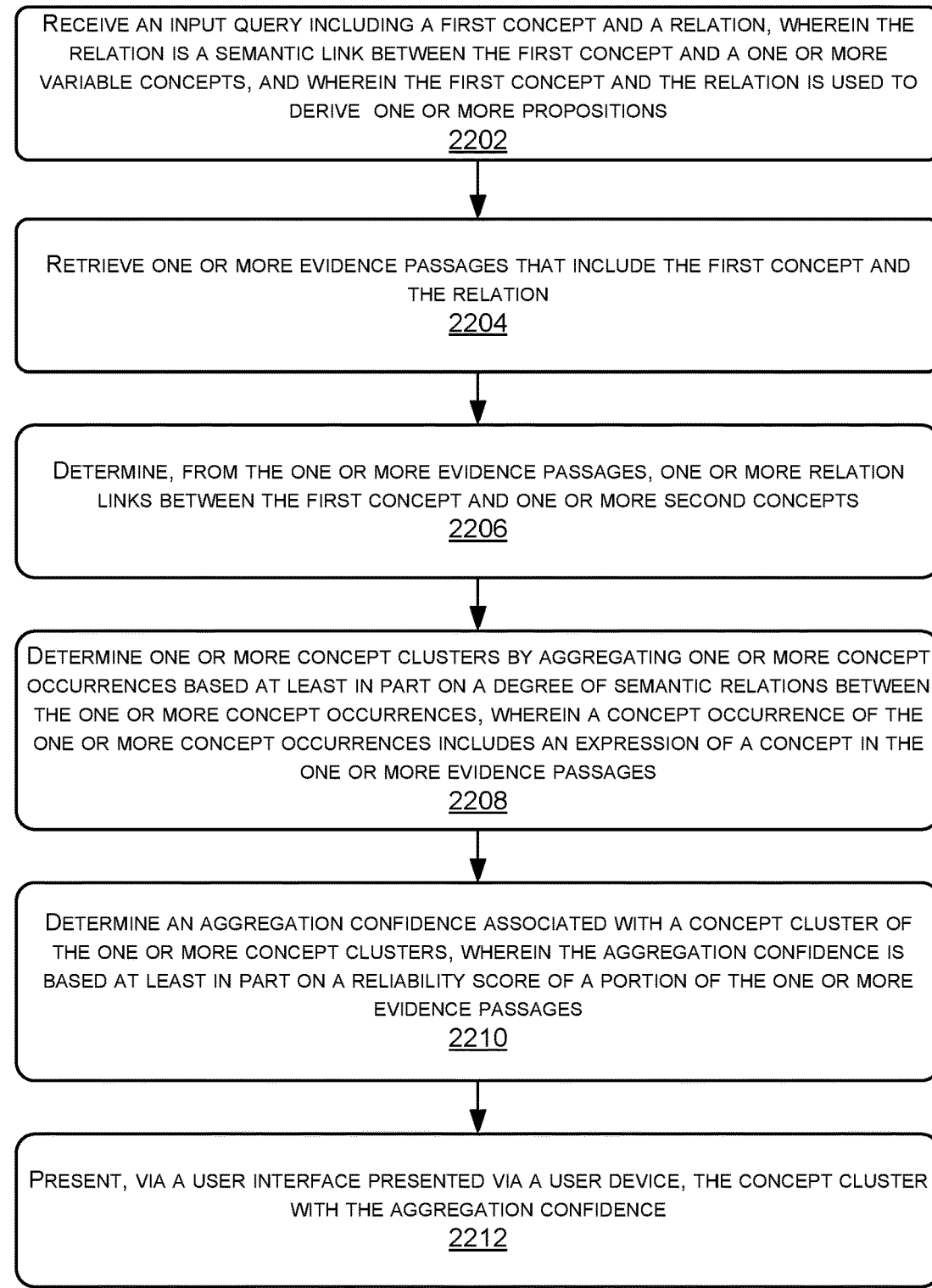
FIG. 22 illustrates an example process for a research assistant tool to identify generic concepts having a relation link to a source concept as supported by evidence, as discussed herein.

FIG. 22 is a flow diagram of illustrative process 2200 for a research assistant tool to identify concepts having a relation link to a source concept as supported by evidence, as discussed herein. The process 2200 is described with reference to the system 100 and may be performed by one or more of the computing devices) 102 and/or in cooperation with any one or more of the device(s) 106. Of course, the process 2200 (and other processes described herein) may be performed in other similar and/or different environments.

At operation 2202, the process may include receiving an input query including a first concept and a relation, wherein the relation is a semantic link between the first concept and a one or more variable concepts, and wherein the first concept and the relation is used to derive one or more propositions. For instance, the computing device(s) 102 or the device(s) 106 may receive an input query including a first concept and a relation, wherein the relation is a semantic link between the first concept and a one or more variable concepts, and wherein the first concept and the relation is used to derive one or more propositions, wherein the one or more propositions includes one or more statements indicating the semantic link.

At operation 2204, the process may include retrieving one or more evidence passages that include the first concept and the relation. For instance, the computing device(s) 102 or the device(s) 106 may At operation 2206, the process may include determining, from the one or more evidence passages, one or more relation links between the first concept and one or more second concepts. For instance, the computing device(s) 102 or the device(s) 106 may determine one or more concept clusters by aggregating one or more concept occurrences based at least in part on a degree of semantic relations between the one or more concept occurrences, wherein a concept occurrence of the one or more concept occurrences includes an expression of a concept in the one or more evidence passages.

At operation 2208, the process may include determining one or more concept clusters by aggregating one or more concept occurrences based at least in part on a degree of semantic relations between the one or more concept occurrences, wherein a concept occurrence of the one or more concept occurrences includes an expression of a concept in the one or more evidence passages. For instance, the computing device(s) 102 or the device(s) 106 may determine one or more concept clusters by aggregating one or more concept occurrences based at least in part on a degree of semantic relations between the one or more concept occurrences, wherein a concept occurrence of the one or more concept occurrences includes an expression of a concept in the one or more evidence passages.

At operation 2210, the process may include determining an aggregation confidence associated with a concept cluster of the one or more concept clusters, wherein the aggregation confidence is based at least in part on a reliability score of a portion of the one or more evidence passages. For instance, the computing device(s) 102 or the device(s) 106 may determine an aggregation confidence associated with a concept cluster of the one or more concept clusters, wherein the aggregation confidence is based at least in part on a reliability score of a portion of the one or more evidence passages.

At operation 2212, the process may include presenting, via a user interface presented via a user device, the concept cluster with the aggregation confidence. For instance, the computing device(s) 102 or the device(s) 106 may presenting, via a user interface presented via a user device, the concept cluster with the aggregation confidence.

Figure 23:
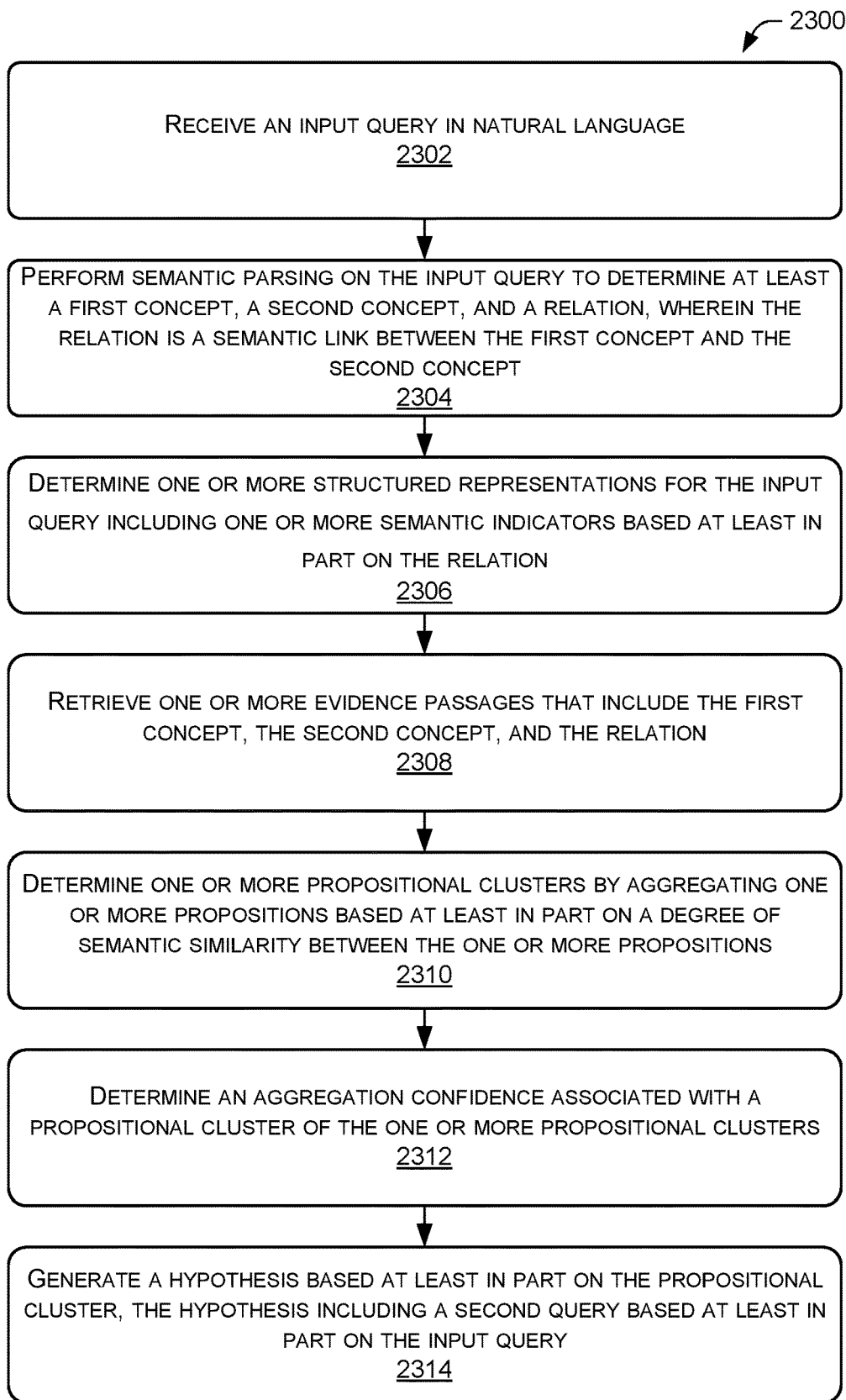
FIG. 23 illustrates an example process for a research assistant tool to determine a query result for a natural language question as supported by evidence, as discussed herein.

FIG. 23 is a flow diagram of illustrative process 2300 for a research assistant tool to determine a query result for a natural language question as supported by evidence, as discussed herein. The process 2300 is described with reference to the system 100 and may be performed by one or more of the computing device(s) 102 and/or in cooperation with any one or more of the device(s) 106. Of course, the process 2300 (and other processes described herein) may be performed in other similar and/or different environments.

At operation 2302, the process may include receiving an input query in natural language. For instance, the computing device(s) 102 or the device(s) 106 may receive an input query in natural language.

At operation 2304, the process may include performing semantic parsing on the input query to determine at least a first concept, a second concept, and a relation, wherein the relation is a semantic link between the first concept and the second concept. For instance, the computing device(s) 102 or the device(s) 106 may perform semantic parsing on the input query to determine at least a first concept, a second concept, and a relation, wherein the relation is a semantic link between the first concept and the second concept.

At operation 2306, the process may include determining one or more structured representations for the input query including one or more semantic indicators based at least in part on the relation. For instance, the computing device(s) 102 or the device(s) 106 may determine one or more structured representations for the input query including one or more semantic indicators based at least in part on the relation.

At operation 2308, the process may include retrieving one or more evidence passages that include the first concept, the second concept, and the relation. For instance, the computing device(s) 102 or the device(s) 106 may retrieve one or more evidence passages that include the first concept, the second concept, and the relation.

At operation 2310, the process may include determining one or more propositional clusters by aggregating one or more propositions based at least in part on a degree of semantic similarity between the one or more propositions. For instance, the computing device(s) 102 or the device(s) 106 may determine one or more propositional clusters by aggregating one or more propositions based at least in part on a degree of semantic similarity between the one or more propositions.

At operation 2312, the process may include determining an aggregation confidence associated with a propositional cluster of the one or more propositional clusters, wherein the aggregation confidence is based at least in part on a reliability score of a portion of the one or more evidence passages. For instance, the computing device(s) 102 or the device(s) 106 may determine an aggregation confidence associated with a propositional cluster of the one or more propositional clusters, wherein the aggregation confidence is based at least in part on a reliability score of a portion of the one or more evidence passages.

At operation 2314, the process may include generating a hypothesis based at least in part on the propositional cluster, the hypothesis including a second query based at least in part on the input query. For instance, the computing device(s) 102 or the device(s) 106 may generate a hypothesis based at least in part on the propositional cluster, the hypothesis including a second query based at least in part on the input query.

Figure 24:
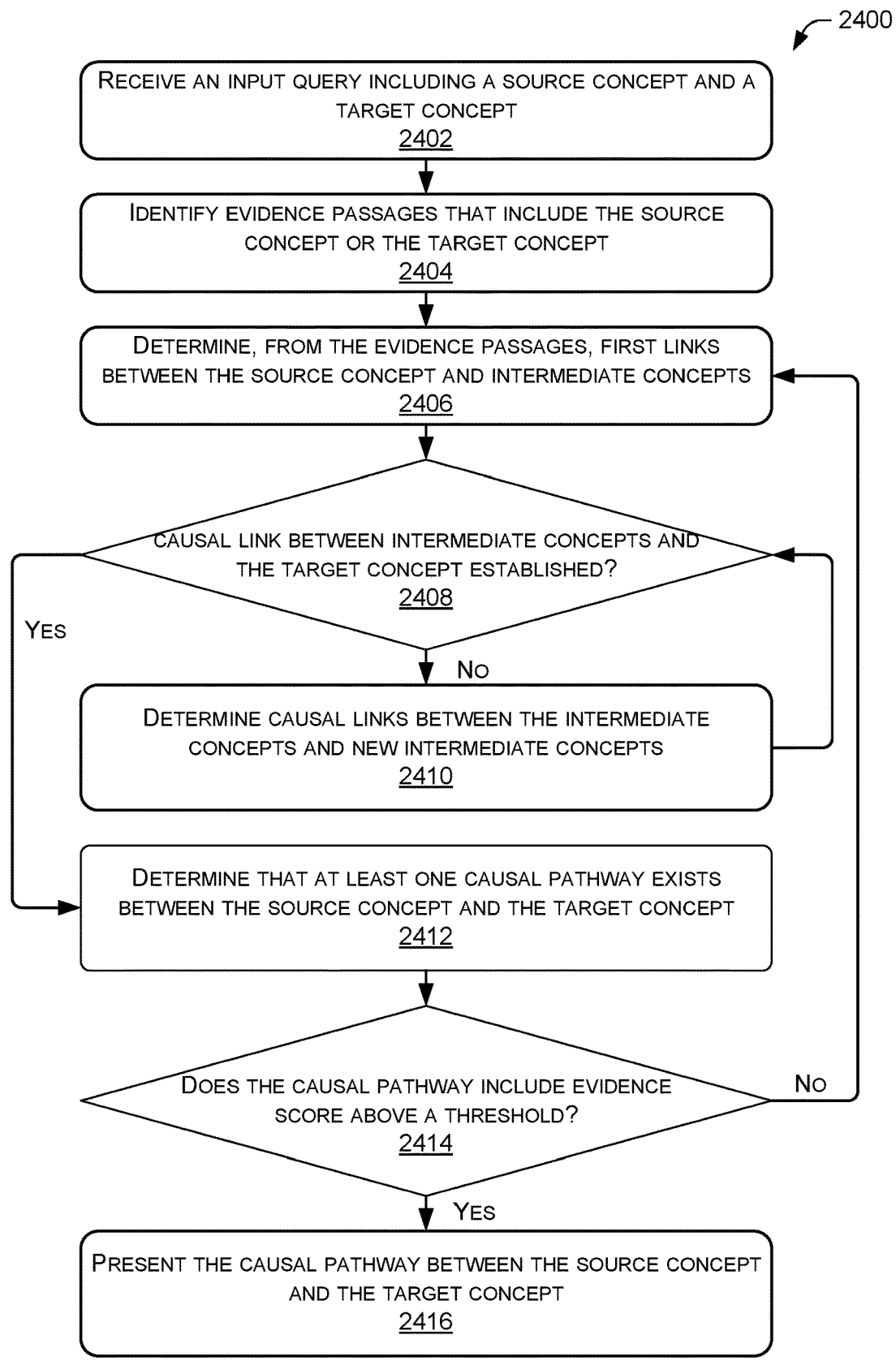
FIG. 24 illustrates an example process for a research assistant tool to determine a causal pathway between a source concept and a target concept as supported by evidence, as discussed herein.

FIG. 24 is a flow diagram of illustrative process 2400 for a research assistant tool to determine a causal pathway between a source concept and a target concept as supported by evidence, as discussed herein. The process 2400 is described with reference to the system 100 and may be performed by one or more of the computing device(s) 102 and/or in cooperation with any one or more of the device(s) 106. Of course, the process 2400 (and other processes described herein) may be performed in other similar and/or different environments.

At operation 2402, the process may include receiving an input query including a source concept and a target concept. For instance, the computing device(s) 102 or the device(s) 106 may receive, via a graphical user interface (GUI) presented via a user device, an input query including a search schema defining search parameters for a research topic, wherein the search parameters includes a source concept and a target concept associated with one or more causal pathways, and the search parameters are used by a research assistant tool to determine one or more concept links to establish the one or more causal pathways between the source concept and the target concept.

At operation 2404, the process may include identifying one or more evidence passages that reference the source concept or the target concept. For instance, the computing device(s) 102 or the device(s) 106 may identify one or more evidence passages that reference the source concept or the target concept.

At operation 2406, the process may include determining, from the one or more evidence passages, one or more first links between the source concept and one or more intermediate concepts. For instance, the computing device(s) 102 or the device(s) 106 may determine, from the one or more evidence passages, one or more first links between the source concept and one or more intermediate concepts.

At operation 2408, the process may include determining if a causal link between the one or more intermediate concepts and the target concept can be established. For instance, the computing device(s) 102 or the device(s) 106 may determine that a causal link between the one or more intermediate concepts and the target concept can be established, and the operations may continue to operations 2412. If the computing device(s) 102 or the device(s) 106 determines that a causal link between the one or more intermediate concepts and the target concept cannot be established, and the operations may continue to operations 2410.

At operation 2410, the process may include determining if a causal link between the intermediate concepts and new intermediate concepts can be established. For instance, the computing device(s) 102 or the device(s) 106 may determine if a causal link between the intermediate concepts and new intermediate concepts can be established, and the operations may return to operations 2408.

At operation 2412, the process may include determining that at least one or more causal pathways exists between the source concept and the target concept.

At operation 2414, the process may include determining whether the causal pathway includes evidence score above a threshold. For instance, the computing device(s) 102 or the device(s) 106 may determine that the causal pathway includes evidence score above a threshold, and the operations may continue to operations 2414. If the computing device(s) 102 or the device(s) 106 determines that the causal pathway includes evidence score below a threshold, and the operations may continue to operations 2406.

At operation 2416, the process may include presenting the causal pathway between the source concept and the target concept. For instance, the computing device(s) 102 or the device(s) 106 may present, via a user interface presented via a user device, the causal pathway including a portion of the one or more evidence passages.

Figure 25:
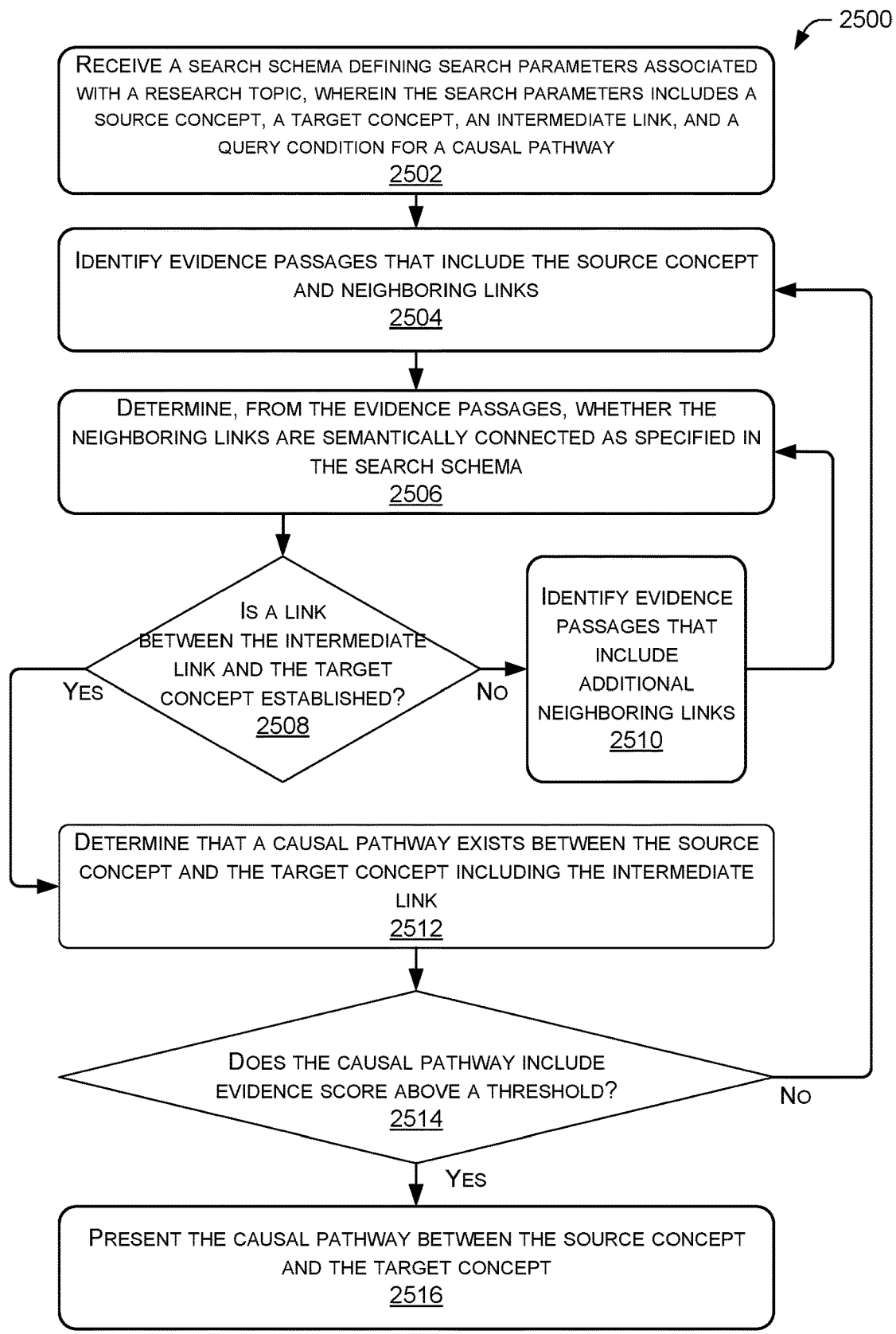
FIG. 25 illustrates an example process for a research assistant tool to determine a causal pathway based on a search schema supported by evidence, as discussed herein.

FIG. 25 is a flow diagram of illustrative process 2500 for a research assistant tool to determine a causal pathway based on a search schema as supported by evidence, as discussed herein. The process 2500 is described with reference to the system 100 and may be performed by one or more of the computing device(s) 102 and/or in cooperation with any one or more of the device(s) 106. Of course, the process 2500 (and other processes described herein) may be performed in other similar and/or different environments.

At operation 2502, the process may include receiving a search schema defining search parameters associated with a research topic, wherein the search parameters includes a source concept, a target concept, an intermediate link, and a query condition for a causal pathway. For instance, the computing device(s) 102 or the device(s) 106 may receive, via a graphical user interface (GUI) presented via a user device, a search schema defining search parameters associated with a research topic, wherein the search parameters includes a source concept, a target concept, an intermediate link, and a query condition for a causal pathway, wherein the intermediate link includes a semantic concept or a semantic relation, wherein the search parameters are used by a research assistant tool to determine one or more evidence links to establish the causal pathway between the source concept and the target concept.

At operation 2504, the process may include identifying one or more evidence passages that reference the source concept and neighboring links. For instance, the computing device(s) 102 or the device(s) 106 may identify one or more evidence passages that reference the source concept and one or more first neighboring links, the one or more first neighboring links establishing a semantic connection between the source concept and one or more intermediate link.

At operation 2506, the process may include determining, from the evidence passages, whether the neighboring links are semantically connect as specified by the search schema. For instance, the computing device(s) 102 or the device( ) 106 may determine, from the one or more evidence passages, whether the one or more first neighboring links are semantically connected and satisfy the query condition.

At operation 2508, the process may include determining if there is a link between the one or more intermediate concepts and the target concept can be established. For instance, the computing device(s) 102 or the device(s) 106 may determine that a causal link between the one or more intermediate concepts and the target concept can be established, and the operations may continue to operations 2512. If the computing device(s) 102 or the device(s) 106 determines that a causal link between the one or more intermediate concepts and the target concept cannot be established, and the operations may continue to operations 2510.

At operation 2510, the process may include identifying evidence passages that includes additional neighboring links. For instance, the computing device(s) 102 or the device(s) 106 may identify one or more evidence passages that includes additional neighboring links, and the operations may return to operations 2506.

At operation 2512, the process may include determining that at least one or more causal pathways exists between the source concept and the target concept. For instance, the computing device(s) 102 or the device(s) 106 may determine that at least one or more causal pathways exists between the source concept and the target concept.

At operation 2514, the process may include determining whether the causal pathway includes evidence score above a threshold. For instance, the computing device(s) 102 or the device(s) 106 may determine that the causal pathway includes evidence score above a threshold, and the operations may continue to operations 2516. If the computing device(s) 102 or the device(s) 106 determines that the causal pathway includes evidence score below a threshold, and the operations may return to operations 2504.

At operation 2516, the process may include presenting the causal pathway between the source concept and the target concept. For instance, the computing device(s) 102 or the device(s) 106 may present, via a user interface presented via a user device, the causal pathway including a portion of the one or more evidence passage.

Figure 26:
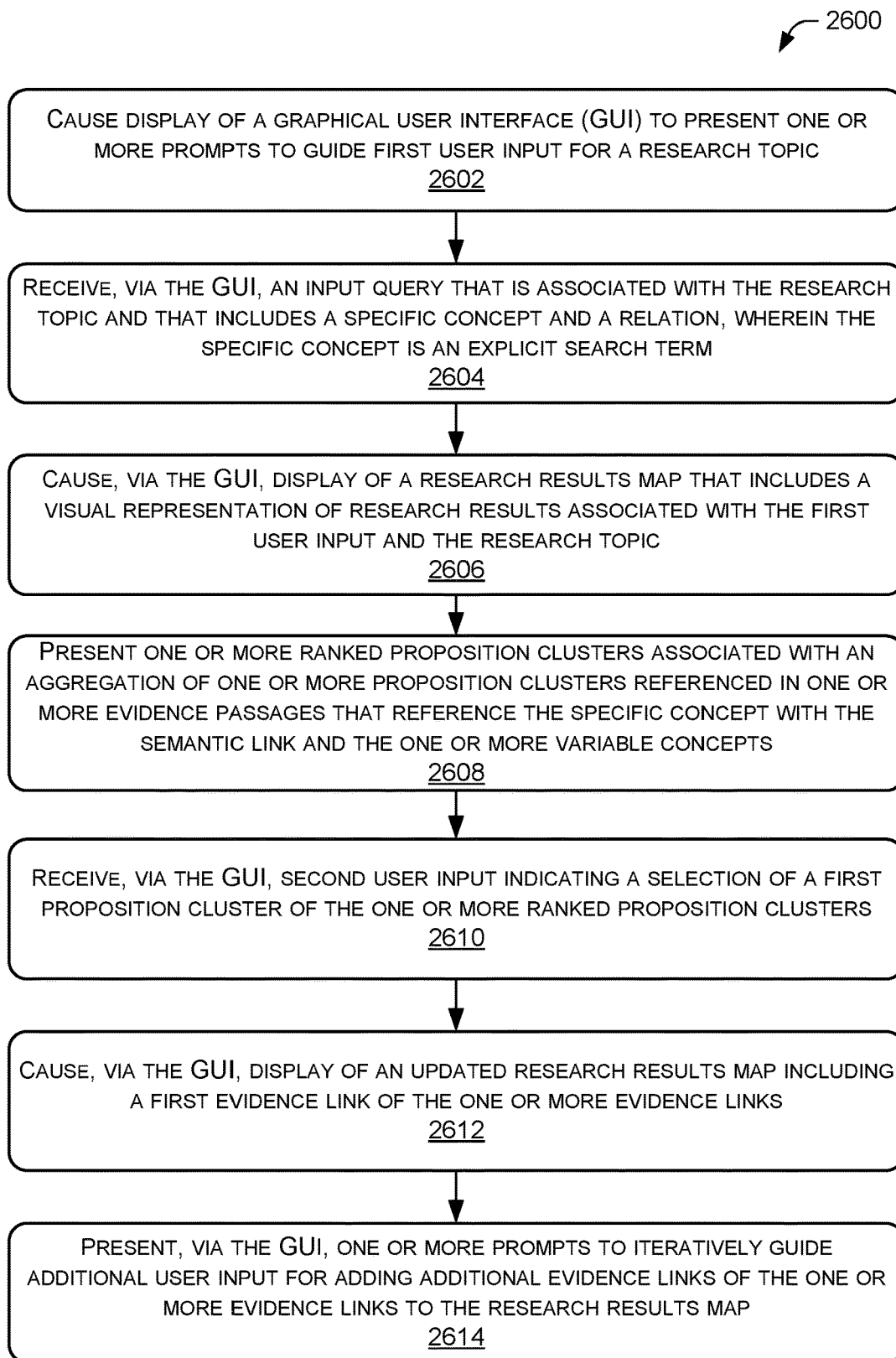
FIG. 26 illustrates an example process for a research assistant user interface to guide user input for exploring evidence chains in response to an input query, as discussed herein.

FIG. 26 is a flow diagram of illustrative process 2600 for a research assistant user interface to guide user input for exploring evidence chains in response to an input query, as discussed herein. The process 2600 is described with reference to the system 100 and may be performed by one or more of the computing device(s) 102 and/or in cooperation with any one or more of the device(s) 106. Of course, the process 2600 (and other processes described herein) may be performed in other similar and/or different environments.

At operation 2602, the process may include causing display of a graphical user interface (GUI) to present one or more prompts to guide first user input for a research topic. For instance, the computing device(s) 102 or the device(s) 106 may cause display of a graphical user interface (GUI) to present one or more prompts to guide first user input for a research topic.

At operation 2604, the process may include receiving, via the GUI presented via a user device, an input query that is associated with the research topic and that includes a specific concept and a relation, wherein the specific concept is an explicit search term. For instance, the computing device(s) 102 or the device(s) 106 may receive, via the GUI presented via a user device, an input query that is associated with the research topic and that includes a specific concept and a relation, wherein the specific concept is an explicit search term, wherein the relation is a semantic link between the specific concept and one or more variable concepts, and wherein the specific concept and the relation are used by a research assistant tool to determine one or more evidence links associated with the research topic.

At operation 2606, the process may include causing, via the GUI presented via the user device, display of a research results map that includes a visual representation of research results associated with the first user input and the research topic.

At operation 2608, the process may include presenting, via the GUI presented via the user device, one or more ranked proposition clusters associated with an aggregation of one or more proposition clusters referenced in one or more evidence passages that reference the specific concept with the semantic link and the one or more variable concepts.

At operation 2610, the process may include receiving, via the GUI presented via the user device, second user input indicating a selection of a first proposition cluster of the one or more ranked proposition clusters, wherein the first proposition cluster includes a statement associated with the semantic link between the specific concept and a first variable concept of the one or more variable concepts.

At operation 2612, the process may include causing, via the GUI presented via the user device, display of an updated research results map including a first evidence link of the one or more evidence links, wherein the first evidence link visually indicates that the specific concept is connected to the first variable concept by the relation.

At operation 2614, the process may include presenting, via the GUI presented via the user device, one or more prompts to iteratively guide additional user input for adding additional evidence links of the one or more evidence links to the research results map.

Figure 27:
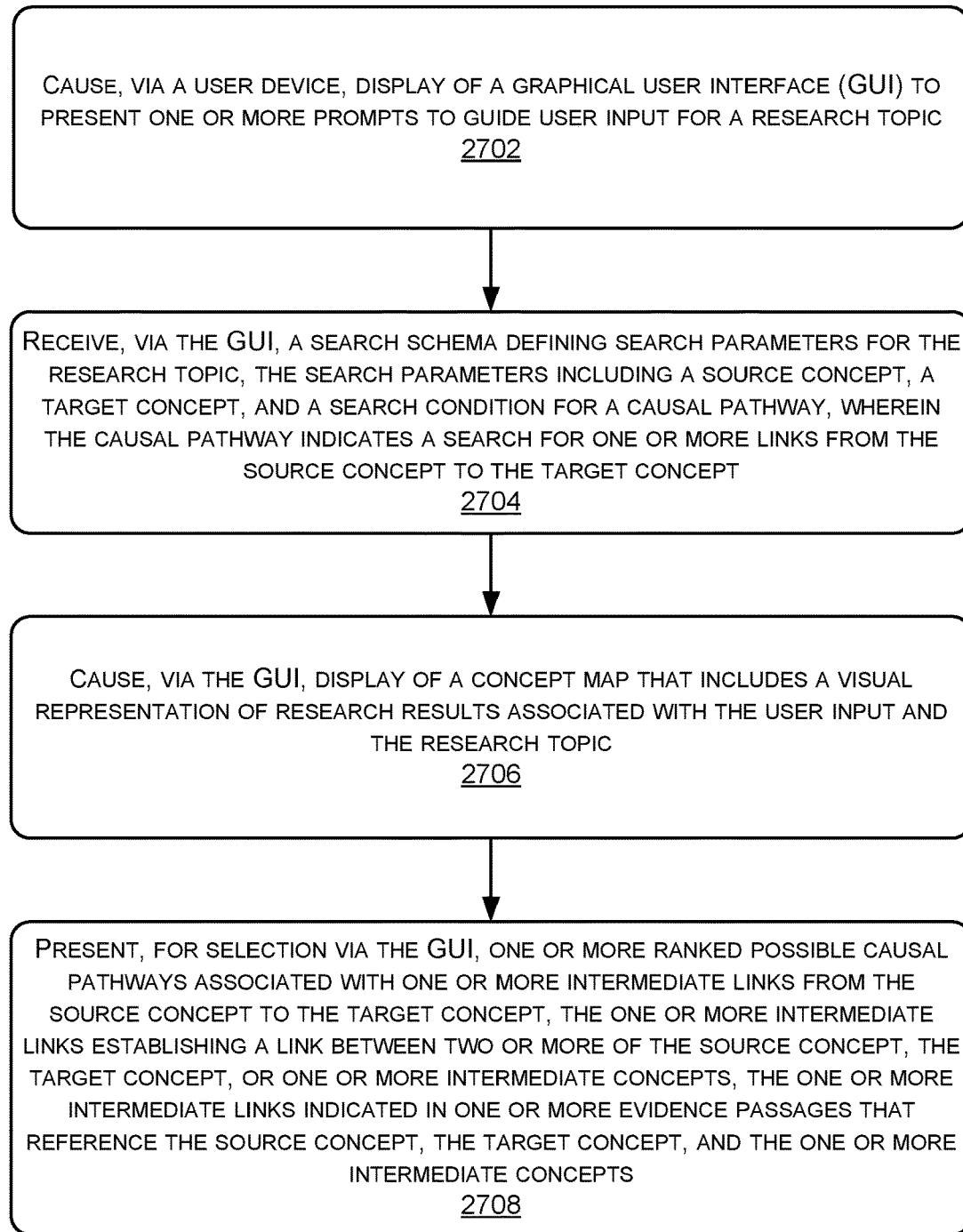
FIG. 27 illustrates an example process for a research assistant user interface to guide user input for exploring evidence chains in response to a search schema, as discussed herein.

FIG. 27 is a flow diagram of illustrative process 2700 for a research assistant user interface to guide user input for exploring evidence chains in response to a search schema, as discussed herein. The process 2700 is described with reference to the system 100 and may be performed by one or more of the computing device(s) 102 and/or in cooperation with any one or more of the device(s) 106. Of course, the process 2700 (and other processes described herein) may be performed in other similar and/or different environments.

At operation 2702, the process may include causing display of a graphical user interface (GUI) to present one or more prompts to guide user input for a research topic. For instance, the computing device(s) 102 or the device(s) 106 may cause display of a graphical user interface (GUI) to present one or more prompts to guide user input for a research topic.

At operation 2704, the process may include receiving, via the GUI presented via a user device, an input query including a search schema defining one or more search parameters for the research topic, the one or more search parameters including a first concept, a second concept, and a search condition, wherein the first concept and the second concept are search terms, wherein the search condition includes a filter for search results by a concept type or a semantic type, wherein the one or more search parameters are used by a research assistant tool to determine one or more evidence links associated with the research topic.

At operation 2706, the process may include causing, via the GUI presented via the user device, display of a research results map that includes a visual representation of research results associated with the user input and the research topic.

At operation 2708, the process may include presenting, for selection via the GUI presented via the user device, one or more ranked relation or proposition clusters associated with one or more semantic links between the first concept and the second concept, the one or more semantic links indicated in one or more evidence passages that reference the first concept and the second concept.

Figure 28:
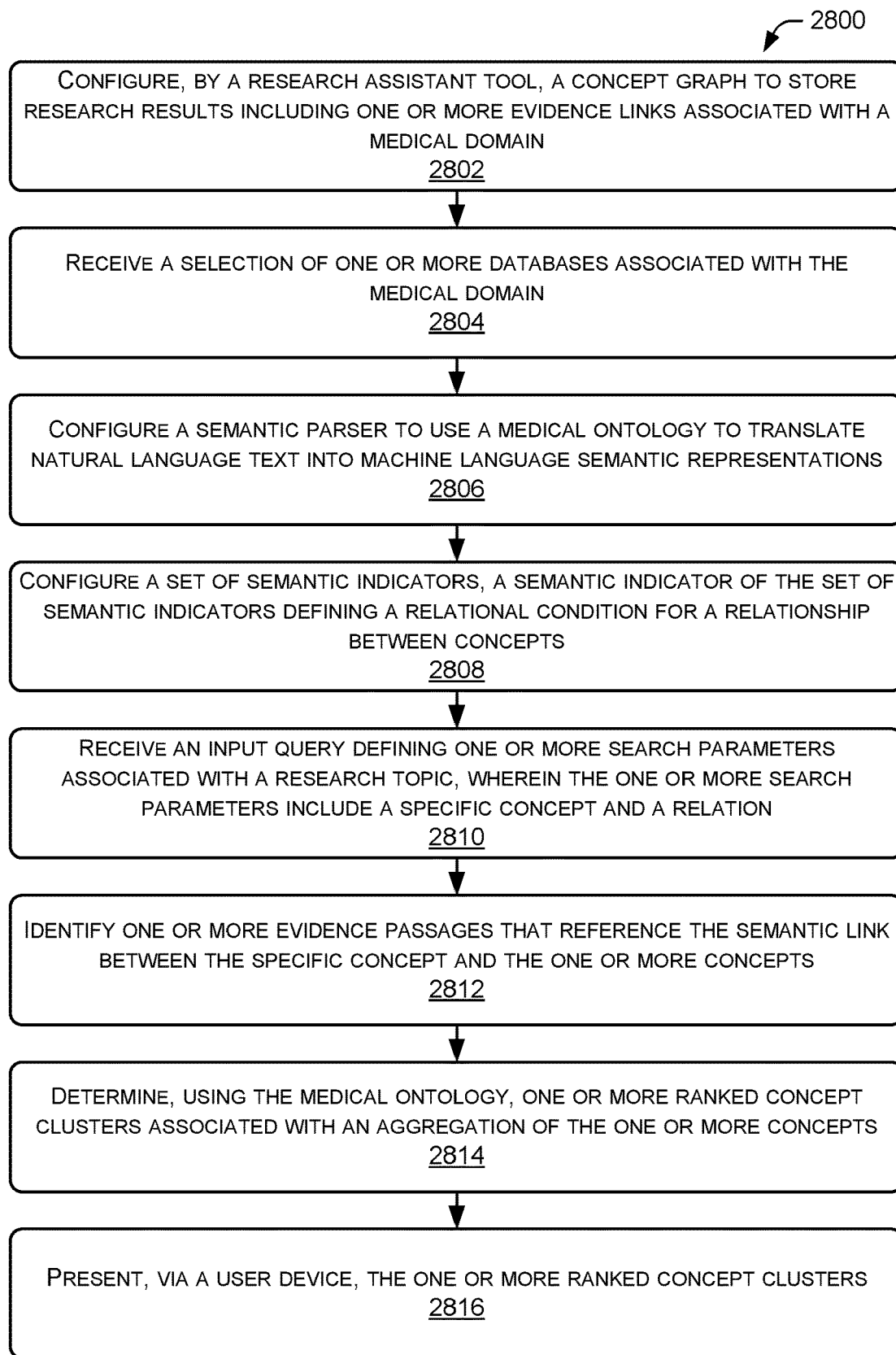
FIG. 28 illustrates an example process for a research assistant tool to identify a treatment result based on a search schema as supported by medical evidence, as discussed herein.

FIG. 28 is a flow diagram of illustrative process 2800 for a research assistant tool to identify a treatment result based on a search schema as supported by medical evidence, as discussed herein. The process 2800 is described with reference to the system 100 and may be performed by one or more of the computing device(s) 102 and/or in cooperation with any one or more of the device(s) 106. Of course, the process 2800 (and other processes described herein) may be performed in other similar and/or different environments.

At operation 2802, the process may include configuring, by a research assistant tool, a research graph to store research results including one or more evidence links associated with a medical domain. For instance, the computing device(s) 102 or the device(s) 106 may configure, by a research assistant tool, a research graph to store research results including one or more evidence links associated with a medical domain, wherein the medical domain is associated with a particular subject of knowledge At operation 2804, the process may include receiving, by a query component associated with the research assistant tool, a selection of one or more databases associated with the medical domain.

At operation 2806, the process may include configuring, by a natural language understanding (NLU) engine associated with the research assistant tool, a semantic parser to use a medical ontology to translate natural language text into machine language semantic representations, the medical ontology defining a set of concepts and classifications of the concepts that represent the medical domain.

At operation 2808, the process may include configuring, by the NLU engine, a set of semantic indicators, a semantic indicator of the set of semantic indicators defining a relational condition for a relationship between concepts to occur, wherein the relational condition is a criterion that is to occur in order for the relationship between concepts to occur.

At operation 2810, the process may include receiving an input query defining one or more search parameters associated with a research topic, wherein the one or more search parameters include a specific concept and a relation associated with the medical domain, wherein the specific concept is an explicit search term and includes a medical condition, wherein the relation is a semantic link between the specific concept and one or more concepts, wherein the input query is used by the research assistant tool to determine the one or more evidence links.

At operation 2812, the process may include identifying, by the query component from the selection of the one or more databases, one or more evidence passages that reference the semantic link between the specific concept and the one or more concepts.

At operation 2814, the process may include determining, using the medical ontology, one or more ranked concept clusters associated with an aggregation of the one or more concepts based at least in part on a degree of similarity between the one or more concepts referenced in the one or more evidence passages. For instance, the computing device(s) 102 or the device(s) 106 may determine, by the natural language understanding (NLU) engine using a semantic parser, one or more semantic interpretations for the one or more evidence passages, wherein the semantic parser translates natural language text from the one or more evidence passages into the one or more semantic interpretations with one or more semantic indicators of the set of semantic indicators. In some examples, the system may determine, using the medical ontology, one or more ranked concept clusters associated with an aggregation of the one or more concepts based at least in part on a degree of similarity between the one or more concepts referenced in the one or more evidence passages.

At operation 2816, the process may include presenting, via a user device, the one or more ranked concept or proposition clusters, wherein individual clusters of the one or more ranked concept or proposition clusters are presented with one or more interactable links to one or more associated portions of the one or more evidence passages.

FIG. 29 is a flow diagram of illustrative process 2900 for a research assistant tool to generate a medical hypothesis based on a search schema as supported by evidence, as discussed herein. The process 2900 is described with reference to the system 100 and may be performed by one or more of the computing device(s) 102 and/or in cooperation with any one or more of the device(s) 106. Of course, the process 2900 (and other processes described herein) may be performed in other similar and/or different environments.

At operation 2902, the process may include receiving a research graph including one or more evidence links associated with a research topic, wherein the one or more evidence links include a first evidence link indicating a first semantic link between a first concept and a second concept, and a second evidence link indicating a second semantic link between the second concept and a third concept, and wherein the one or more evidence links are associated with a knowledge representation associated with a knowledge domain. For instance, the computing device(s) 102 or the device(s) 106 may receive a research graph including one or more evidence links associated with a research topic, wherein the one or more evidence links include a first evidence link indicating a first semantic link between a first concept and a second concept, and a second evidence link indicating a second semantic link between the second concept and a third concept, and wherein the one or more evidence links are associated with a knowledge representation associated with a knowledge domain.

At operation 2904, the process may include causing display of a visual representation of the research graph, wherein the research graph visually indicates the first concept, the second concept, and the third concept as concept nodes, and the first semantic link and the second semantic link as relationship links, wherein the concept nodes are selectable to view of associated portions of one or more evidence passages. For instance, the computing device(s) 102 or the device(s) 106 may cause display of a visual representation of the research graph, wherein the research graph visually indicates the first concept, the second concept, and the third concept as concept nodes, and the first semantic link and the second semantic link as relationship links, wherein the concept nodes are selectable to view of associated portions of one or more evidence passages.

At operation 2906, the process may include causing display of one or more prompts to guide user input for the research topic. For instance, the computing device(s) 102 or the device(s) 106 may cause display of one or more prompts to guide user input for the research topic.

The methods described herein represent sequences of operations that can be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the processes. In some embodiments, one or more operations of the method may be omitted entirely. Moreover, the methods described herein can be combined in whole or in part with each other or with other methods.

The various techniques described herein may be implemented in the context of computer-executable instructions or software, such as program modules, that are stored in computer-readable storage and executed by the processor(s) of one or more computing devices such as those illustrated in the figures. Generally, program modules include routines, programs, objects, components, data structures, etc., and define operating logic for performing particular tasks or implementing particular abstract data types.

Other architectures may be used to implement the described functionality and are intended to be within the scope of this disclosure. Furthermore, although specific distributions of responsibilities are defined above for purposes of discussion, the various functions and responsibilities might be distributed and divided in different ways, depending on circumstances.

Similarly, the software may be stored and distributed in various ways and using different means, and the particular software storage and execution configurations described above may be varied in many different ways. Thus, software implementing the techniques described above may be distributed on various types of computer-readable media, not limited to the forms of memory that are specifically described.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:
1. A system comprising:
one or more processors; and
memory storing computer-executable instructions that, when executed, cause the one or more processors to perform operations comprising:
configuring, by a research assistant tool, a research graph to store research results including one or more evidence links associated with a medical domain, wherein the medical domain is associated with a particular subject of knowledge;
receiving, by a query component associated with the research assistant tool, a selection of one or more databases associated with the medical domain;
configuring, by a natural language understanding (NU) engine associated with the research assistant tool, a semantic parser to use a medical ontology to translate natural language text into machine language semantic representations, the medical ontology defining a set of concepts and classifications of the concepts that represent the medical domain;
configuring, by the NLU engine, a set of semantic indicators, a semantic indicator of the set of semantic indicators defining a relational condition for a relationship between concepts to occur, wherein the relational condition is a criterion that is to occur in order for the relationship between concepts to occur;
receiving an input query defining one or more search parameters associated with a research topic, wherein the one or more search parameters include a specific concept and a relation associated with the medical domain, wherein the specific concept is an explicit search term and includes a medical condition, wherein the relation is a semantic link between the specific concept and one or more concepts, wherein the input query is used by the research assistant tool to determine the one or more evidence links;
identifying, by the query component from the selection of the one or more databases, one or more evidence passages that reference the semantic link between the specific concept and the one or more concepts;
determining, by the natural language understanding (NIX) engine using a semantic parser, one or more semantic interpretations for the one or more evidence passages, wherein the semantic parser translates natural language text from the one or more evidence passages into the one or more semantic interpretations with one or more semantic indicators of the set of semantic indicators:
determining, using the medical ontology, one or more ranked concept clusters associated with an aggregation of the one or more concepts based at least in part on a degree of similarity between the one or more concepts referenced in the one or more evidence passages; and presenting, via a user device, the one or more ranked concept or proposition clusters, wherein individual clusters of the one or more ranked concept or proposition clusters are presented with one or more interactable links to one or more associated portions of the one or more evidence passages.

2. The system of claim 1, wherein the operations further comprise:

receiving second user input indicating a selection of a first concept or proposition cluster of the one or more ranked concept or proposition clusters;

determining that an evidence link of the one or more evidence links includes the semantic link between the medical condition and the first concept or proposition cluster and is supported by a portion of the one or more evidence passages associated with the first concept or proposition cluster;

storing the evidence link associated with the medical condition in a knowledge database; and causing, via the user device, display of one or more prompts to iteratively guide additional user input for adding additional evidence links of the one or more evidence links associated with the medical condition to the research graph.

3. The system of claim 1, wherein one or more databases includes one or more of academic paper databases, research paper databases, case report databases, review article databases, scientific journal databases, or digital libraries.

4. The system of claim 1, wherein the one or more interactable links are presented with evidence scores for the one or more associated portions of the one or more evidence passages, wherein an evidence score of the evidence scores is determined, by the research assistant tool, based at least in part on a redundancy score, wherein the redundancy score is based at in part on a count of repeat reference of an evidence passage in the one or more associated portions of the one or more evidence passages.

5. The system of claim 1, wherein the one or more interactable links are presented with evidence scores for the one or more associated portions of the one or more evidence passages, wherein an evidence score of the evidence scores is determined, by the research assistant tool, based at least in part on a reliability score, wherein the reliability score is based at least in part on one or more features including an age of the evidence passage, a knowledge source of the evidence passage, an authorship of the evidence passage, or a media source of the evidence passage.

6. The system of claim 1, wherein the one or more interactable links are presented with evidence scores for the one or more associated portions of the one or more evidence passages, wherein an evidence score of the evidence scores is determined, by the research assistant tool, based at least in part on an originality score, wherein the originality score is based at in part on determining a count of unique originating sources for the one or more associated portions of the one or more evidence passages.

7. A computer-implemented method comprising:

generating, by a research assistant tool, a research graph to store research results associated with a research topic in a domain;

configuring a set of semantic indicators, wherein a semantic indicator of the set of semantic indicators defines a relational condition for a relationship between concepts; wherein the relational condition is a criterion that is to occur in order for the relationship between concepts to occur;

receiving an input query including a search schema defining one or more search parameters for the research topic, wherein the one or more search parameters include a first concept, a second concept, and a search condition, wherein the first concept and the second concept are search terms, wherein the search condition includes a filter for search results by a concept type or a semantic type, wherein the one or more search parameters are used by the research assistant tool to determine one or more evidence links associated with the research topic;

causing display of one or more ranked relation clusters associated with one or more semantic links between the first concept and the second concept, wherein the one or more semantic links are referenced by one or more evidence passages that reference the first concept and the second concept;

receiving user input indicating a selection of a first relation cluster of the one or more ranked relation clusters, wherein the first relation cluster is associated with a first semantic link between the first concept and the second concept;

determining to add an evidence link to the research graph, wherein the evidence link includes the semantic link between the first concept and the second concept and is supported by a portion of the one or more evidence passages associated with the first relation cluster, wherein the evidence link includes a structured representation of the first semantic link between the first concept and the second concept, and a semantic indicator defining a condition for the first semantic link; and causing display of one or more prompts to iteratively guide additional user input for adding additional evidence links to the research graph.

8. The computer-implemented method of claim 7, further comprising:

receiving user feedback associated with the evidence link, wherein the user feedback indicates a positive association or a negative association of the portion of the one or more evidence passages supporting the evidence link; and storing, in a knowledge database, the evidence link in association with the portion of the one or more evidence passages associated with the user feedback.

9. The computer-implemented method of claim 7, further comprising:

ranking the portion of the one or more evidence passages based at least in part by evidence scores for the one or more evidence passages;

determining, using a semantic parser with the one or more semantic indicators, semantic interpretations for the one or more evidence passages, wherein the semantic parser translates natural language text from the one or more evidence passages into machine language representations; and generating one or more annotated evidence passages based at least in part on annotating individual passages of the one or more evidence passages with associated semantic interpretations of the semantic interpretations.

10. The computer-implemented method of claim 9, further comprising:

receiving a request to generate a document summary for the research results; and transmitting, to a user device, the research results with the document summary summarizing the one or more annotated evidence passages.

11. The computer-implemented method of claim 7, further comprising:
receiving a request to perform a second query associated with the second concept;
causing display of a prompt for the second query; and
receiving the second query including a second search schema defining one or more second search parameters including the second concept and a third concept.

12. The computer-implemented method of claim 11 further comprising:
retrieving one or more second evidence passages that reference the second concept or proposition and the third concept or proposition;
determining that a direct link between the second concept and the third concept cannot be established;
determining that a multilink between the second concept and the third concept can be established, wherein the multilink includes a first intermediate link between the second concept and an intermediate concept, and a second intermediate link between the intermediate concept and the third concept, wherein determining the multilink can be established includes determining that a first condition associated with a first semantic indicator for the first intermediate link can be met for the second intermediate link; and
causing display of the multilink including the first intermediate link and the second intermediate link.

13. The computer-implemented method of claim 12, further comprising:
receiving second user input to confirm the multilink; and
determining to add a second evidence link and a third evidence link to the research graph, wherein the second evidence link includes the first intermediate link between the second concept and the intermediate concept, and the third evidence link including the second intermediate link between the intermediate concept and the third concept and is supported by a portion of the one or more second evidence passages associated with the multilink.

14. The computer-implemented method of claim 13, further comprising:
receiving a second request to generate a hypothesis based at least in part on the research graph;
generating one or more hypotheses based at least in part on the first evidence link, the second evidence link, the third evidence link, the one or more evidence passages, and the one or more second evidence passages; and
causing display of the one or more hypotheses, wherein the one or more hypotheses include a clinical trial recommendation.

15. One or more non-transitory computer-readable media storing computer executable instructions that, when executed, cause one or more processors to perform operations comprising:
receiving a research graph including one or more evidence links associated with a research topic, wherein the one or more evidence links include a first evidence link indicating a first semantic link between a first concept and a second concept, and a second evidence link indicating a second semantic link between the second concept and a third concept, and wherein the one or more evidence links are associated with a knowledge representation associated with a knowledge domain;
causing display of a visual representation of the research graph, wherein the research graph visually indicates the first concept, the second concept, and the third concept as concept nodes, and the first semantic link and the second semantic link as relationship links, wherein the concept nodes are selectable to view of associated portions of one or more evidence passages; and
causing display of one or more prompts to guide user input for the research topic.

16. The one or more non-transitory computer-readable media of claim 15, the operations further comprise:
receiving a request to change a view of the visual representation of the research graph; and
based at least in part on the request, causing display of a second visual representation of the research graph, wherein the concept nodes included within the second visual representation of the research graph are annotated with summarized portions of the one or more evidence passages.

17. The one or more non-transitory computer-readable media of claim 15, the operations further comprise:
receiving a request to perform an input query associated with the third concept;
receiving the input query including a search schema defining a fourth concept; and
causing display of one or more second prompts to iteratively guide additional user input for determining a third evidence link of the one or more evidence links.

18. The one or more non-transitory computer-readable media of claim 17, the operations further comprising:
determining that the third evidence link includes a third semantic link between the third concept and the fourth concept, wherein the third evidence link is associated with one or more second evidence passages; and
updating the visual representation of the research graph to visually indicate that the third concept is connected to the fourth concept by the third semantic link.

19. The one or more non-transitory computer-readable media of claim 18, the operations further comprising:
receiving a second request to generate a hypothesis or proposition based at least in part on the first evidence link, the second evidence link, and the third evidence link;
generating the hypothesis based at least in part on the first evidence link, the second evidence link, the third evidence link, the one or more evidence passages, and the one or more second evidence passages; and
causing display of the hypothesis indicating an inferred relationship between the first concept and the fourth concept.

20. The one or more non-transitory computer-readably of claim 18, the operations further comprising:
receiving a second request to generate a document summary for the research graph, wherein the research graph includes the first evidence link, the second evidence link, and the third evidence link; and
causing, via a user device, display of the document summary summarizing the portion of the one or more evidence passages and the one or more second evidence passages including an associated reference citation to a knowledge database associated with the knowledge domain.

* * * * *